(12) United States Patent
Holden et al.

(10) Patent No.: US 12,256,863 B2
(45) Date of Patent: Mar. 25, 2025

(54) SENSING SYSTEM AND METHOD OF OPERATION

(71) Applicant: Oxford Nanopore Technologies PLC, Oxford (GB)

(72) Inventors: Matthew Holden, Cambridge, MA (US); Andrew John Heron, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 883 days.

(21) Appl. No.: 17/297,506

(22) PCT Filed: Nov. 28, 2019

(86) PCT No.: PCT/GB2019/053366
§ 371 (c)(1),
(2) Date: May 27, 2021

(87) PCT Pub. No.: WO2020/109800
PCT Pub. Date: Jun. 4, 2020

(65) Prior Publication Data
US 2022/0001386 A1 Jan. 6, 2022

Related U.S. Application Data

(60) Provisional application No. 62/772,331, filed on Nov. 28, 2018.

(51) Int. Cl.
*B01L 3/00* (2006.01)
*A47J 36/24* (2006.01)
(Continued)

(52) U.S. Cl.
CPC ....... *A47J 36/2488* (2013.01); *B01L 3/50273* (2013.01); *B01L 3/502784* (2013.01);
(Continued)

(58) Field of Classification Search
CPC .......... B01L 3/50273; B01L 3/502784; B01L 2300/0645; B01L 2200/0673;
(Continued)

(56) References Cited

U.S. PATENT DOCUMENTS 6,565,727 B1 * 5/2003 Shenderov ........ B01L 3/502746
204/600
6,911,132 B2 * 6/2005 Pamula ..................... C25B 9/00
204/600
(Continued)

FOREIGN PATENT DOCUMENTS

CN 107923912 A 4/2018
CN 107923927 A 4/2018
(Continued)

OTHER PUBLICATIONS

International Search Report and Written Opinion for Application No. PCT/GB2019/053366, mailed Mar. 4, 2020.
(Continued)

*Primary Examiner* — Shogo Sasaki
(74) *Attorney, Agent, or Firm* — Wolf, Greenfield & Sacks, P.C.

(57) ABSTRACT

The invention relates to a sensing system comprising an electrowetting device, which electrowetting device comprises an array of actuation electrodes, and a control system configures to perform droplet operations on a system of droplets present in the sensing system. The invention also relates to a method of operating the sensing system of the invention. The invention also provides novel droplet constructs which can be made and manipulated in the sensing system of the invention.

38 Claims, 13 Drawing Sheets

(51) Int. Cl.
*C12Q 1/6869* (2018.01)
*H05B 3/00* (2006.01)

(52) U.S. Cl.
CPC .... *C12Q 1/6869* (2013.01); *B01L 2200/0673* (2013.01); *B01L 2300/0645* (2013.01); *B01L 2300/161* (2013.01); *B01L 2400/0427* (2013.01); *H05B 3/0071* (2013.01)

(58) Field of Classification Search
CPC ....... B01L 2400/0427; B01L 2300/161; C12Q 1/6869; A47J 36/2488; H05B 3/0071
See application file for complete search history.

(56) References Cited

U.S. PATENT DOCUMENTS

| | | | |
|---|---|---|---|
| 6,916,488 | B1 | 7/2005 | Meier et al. |
| 7,163,612 | B2 * | 1/2007 | Sterling .............. B01L 3/50273 204/600 |
| 7,693,666 | B2 * | 4/2010 | Griffith ............. B01L 3/502784 702/22 |
| 8,192,701 | B2 * | 6/2012 | Ermakov ............... B82Y 30/00 422/537 |
| 8,653,832 | B2 | 2/2014 | Hadwen et al. |
| 9,782,775 | B2 * | 10/2017 | Akella .................. F04B 19/006 |
| 11,684,916 | B2 * | 6/2023 | Yao ................... B01L 3/502792 422/502 |
| 11,951,481 | B2 * | 4/2024 | Wu ............................ B01L 7/52 |
| 2004/0231987 | A1 | 11/2004 | Sterling et al. |
| 2010/0194408 | A1 | 8/2010 | Sturmer et al. |
| 2012/0007608 | A1 | 1/2012 | Hadwen et al. |
| 2012/0194492 | A1 | 8/2012 | Hadwen et al. |
| 2016/0301157 | A1 * | 10/2016 | Schwalbach ......... H04B 1/3833 |
| 2016/0305906 | A1 | 10/2016 | Amos et al. |
| 2017/0056887 | A1 * | 3/2017 | Hadwen ............... G01N 33/579 |
| 2017/0059523 | A1 * | 3/2017 | Hadwen ............. G01N 33/4905 |
| 2020/0055053 | A1 * | 2/2020 | Wu ............................ B01L 7/52 |

FOREIGN PATENT DOCUMENTS

| | | |
|---|---|---|
| CN | 111587150 A | 6/2019 |
| GB | 2533952 A | 7/2016 |
| JP | 4713306 B2 | 6/2011 |
| JP | 2012-018400 A | 1/2012 |
| JP | 2012-150098 A | 8/2012 |
| JP | 2012-163956 A | 8/2012 |
| JP | 2015-535179 A | 12/2015 |
| WO | WO 2010/086603 A1 | 8/2010 |
| WO | WO 2011/067559 A1 | 6/2011 |
| WO | WO 2012/107778 A2 | 8/2012 |
| WO | WO 2013/041878 A1 | 3/2013 |
| WO | WO 2013/083983 A1 | 6/2013 |
| WO | WO 2013/121224 A1 | 8/2013 |
| WO | WO 2013/153359 A1 | 10/2013 |
| WO | WO 2014/064443 A2 | 5/2014 |
| WO | WO 2014/064444 A1 | 5/2014 |
| WO | WO 2015/140535 A1 | 9/2015 |
| WO | WO 2016/034591 A2 | 3/2016 |
| WO | WO 2017/004504 A1 | 1/2017 |
| WO | WO 2017/149316 A1 | 9/2017 |
| WO | WO 2017/149317 A1 | 9/2017 |
| WO | WO 2017/149318 A1 | 9/2017 |
| WO | WO 2018/096348 A1 | 5/2018 |
| WO | WO 2019/126715 A1 | 6/2019 |
| WO | WO 2019/227013 A1 | 11/2019 |

OTHER PUBLICATIONS

International Preliminary Report on Patentability for Application No. PCT/GB2019/053366, mailed Jun. 10, 2021.
Bayley et al., Droplet interface bilayers. Mol Biosyst. Dec. 2008;4(12):1191-208. doi: 10.1039/b808893d. Epub Sep. 5, 2008. Author Manuscript.
Deamer et al., Nanopores and nucleic acids: prospects for ultrarapid sequencing. Trends Biotechnol. Apr. 2000;18(4):147-51. doi: 10.1016/s0167-7799(00)01426-8.
Dupin et al., Signalling and differentiation in emulsion-based multi-compartmentalized in vitro gene circuits. Nat Chem. Jan. 2019;11(1):32-39. doi: 10.1038/s41557-018-0174-9. Epub Nov. 26, 2018.
Martel et al., Handling of artificial membranes using electrowetting-actuated droplets on a microfluidic device combined with integrated pA-measurements. Biomicrofluidics. Mar. 2012;6(1):12813-128137. doi: 10.1063/1.3665719. Epub Mar. 15, 2012.
Trantidou et al., Engineering Compartmentalized Biomimetic Micro- and Nanocontainers. ACS Nano. Jul. 25, 2017;11(7):6549-6565. doi: 10.1021/acsnano.7b03245. Epub Jul. 5, 2017.
Wauer et al., Construction and manipulation of functional three-dimensional droplet networks. ACS Nano. Jan. 28, 2014;8(1):771-9. doi: 10.1021/nn405433y. Epub Jan. 6, 2014.
PCT/GB2019/053366, Mar. 4, 2020, International Search Report and Written Opinion.
PCT/GB2019/053366, Jun. 10, 2021, International Preliminary Report on Patentability.
Altschul SF. A protein alignment scoring system sensitive at all evolutionary distances. J Mol Evol. Mar. 1993;36(3):290-300. doi: 10.1007/BF00160485.
Boza et al., DeepNano: Deep recurrent neural networks for base calling in MinION nanopore reads. PLoS One. Jun. 5, 2017;12(6):e0178751. doi: 10.1371/journal.pone.0178751.
Devereux et al., A comprehensive set of sequence analysis programs for the VAX. Nucleic Acids Res. Jan. 11, 1984;12(1 Pt 1):387-95. doi: 10.1093/nar/12.1part1.387.
Holden et al., Functional bionetworks from nanoliter water droplets. J Am Chem Soc. Jul. 11, 2007;129(27):8650-5. doi: 10.1021/ja072292a. Epub Jun. 16, 2007.
Langecker et al., Synthetic lipid membrane channels formed by designed DNA nanostructures. Science. Nov. 16, 2012;338(6109):932-6. doi: 10.1126/science.1225624.
Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010. Author Manuscript, 21 pages.
Luan et al., Base-by-base ratcheting of single stranded DNA through a solid-state nanopore. Phys Rev Lett. Jun. 11, 2010;104(23):238103. doi: 10.1103/PhysRevLett.104.238103. Epub Jun. 10, 2010. Author Manuscript, 9 pages.
Sambrook, J. and Russell, D. Molecular Cloning: A Laboratory Manual. 3rd Edition. 2001; Cold Spring Harbor Laboratory Press, Cold Spring Harbor, NY.
Altschul et al., Basic local alignment search tool. J Mol Biol. Oct. 5, 1990;215(3):403-10. doi: 10.1016/S0022-2836(05)80360-2.

* cited by examiner

SENSING SYSTEM AND METHOD OF OPERATION

RELATED APPLICATIONS

This Application is a national stage filing under 35 U.S.C. § 371 of international PCT application PCT/GB2019/053366, filed Nov. 28, 2019, which claims priority under 35 U.S.C. § 119 (e) to U.S. provisional patent application Ser. No. 62/772,331, filed Nov. 28, 2018, the entire contents of each of which are incorporated herein by reference.

FIELD OF THE INVENTION

In some aspects, the invention relates to a method of operating a sensing system, which sensing system comprises an electrowetting device and a control system configured to provide a signal to the electrowetting device. In other aspects, the invention further relates to the sensing system itself, and to constructs comprising droplets of liquid medium which can be made or manipulated in the sensing system.

BACKGROUND TO THE INVENTION

There is considerable interest in the rapid detection, analysis and processing of chemical species, and systems which can enable such analysis.

Leading devices in this area are devices such as those described in WO 2014/064443. This device comprises an array of individual suspended membranes of amphipathic molecules containing respective transmembrane pores. Such membranes comprising transmembrane pores are described in, for instance, WO 2014/064444. The device also comprises an application-specific integrated circuit (ASIC) containing an array of sensing electrodes. In use, a sample is provided to the device. Any analyte present in the sample may interact with the array of transmembrane pores. Each transmembrane pore is associated with a sensing electrode within the electrode array, and the interaction of an analyte with the transmembrane pore creates a signal at the associated sensing electrode. Accordingly, analysis of the electrical signals obtained by the ASIC can provide information on the analyte(s) present.

Although such devices are highly advanced and useful systems, there remains room for improvement.

These devices currently do not permit the analysed sample to be easily recovered intact, because it is difficult to access the internal chambers of the device without causing damage to the device. It would therefore be desirable to provide a sensing system which is able to recover a sample provided to the system. Recovery of a sample is desirable for various reasons: for instance, once the identity of the sample is known it may be advantageous to subject it to a further experimental procedure that cannot be performed in devices such as those described in WO 2014/064443. Alternatively or additionally, it may be important to retain the sample for future reference. This is particularly important in cases where only a small quantity of sample is available.

Once the analyte(s) present in a sample have been identified, it is often desirable to perform further experimental procedures upon that sample. The particular experimental procedures that are of interest may not be known until the sample has been analysed. For instance, in the case of a sample containing DNA, once the DNA has been identified or partially identified it may be of interest to amplify the DNA by PCR to provide additional material for further experiments. It may also be of interest to modify the DNA. It would therefore be desirable to provide a system which is capable of performing a wide range of further experimental procedures upon a sample.

It would be particularly advantageous to provide a system which can perform such further procedures directly in situ, without removing the sample from the system, both for user convenience and to avoid contamination or degradation of the sample. It would also be advantageous to provide such a sensing system which is capable of performing the further experimental procedures rapidly, especially where a lifetime of the sample may be short or where the analysis performed is used to enable swift decisions to be taken in a medical context.

It would also be highly desirable to provide a device with an extended lifetime. The lifetime of currently available devices may be limited because the electron mediator contained in the device can become depleted over time. However, it is difficult to access the internal chambers of such devices to add more electron mediator without breaking the device.

It would also be highly desirable to provide a device having the ability to measure an analyte to an improved level of accuracy. For example, DNA as analyte can currently be sequenced by rapid-processing nanopore sequencing methods with a high degree of accuracy. However any improvements in accuracy are always desirable.

In the field of display technology, electro-wetting on dielectric (EWOD) devices are known for manipulating droplets of liquid in a fluid medium. In this field, electro-wetting on dielectric is a well-known technique for manipulating droplets of fluid by the application of an electric field, for example as disclosed in US2016/0305906. Example configurations and operation of EWOD devices are described in the following documents.

U.S. Pat. No. 6,911,132 discloses a two-dimensional EWOD array to control the position and movement of droplets in two dimensions. U.S. Pat. No. 6,565,727 discloses methods for other droplet operations including the splitting and merging of droplets, and the mixing together of droplets of different materials. U.S. Pat. No. 7,163,612 describes how an active matrix (AM) arrangement based on thin film electronics including thin-film transistors (TFT) may be used to control the addressing of voltage pulses to an EWOD device, using circuit arrangements similar to those employed in AM display technologies. Devices of this general type may be referred to as AM-EWOD devices.

SUMMARY OF THE INVENTION

The present inventors have realised that by utilising an EWOD device together with a control system, they can produce a sensing system capable of performing the functions of known sensing systems such as the nanopore array system described in WO 2014/064443 without requiring the complex physical structures needed to contain liquids such as quantities of sample or arrays of electrodes. Rather, manipulation of the electrical field provides the necessary containment of a liquid sample, and/or liquids comprising chemicals such as an electron mediator. Moreover, the inventors have understood that removing the walls of the sensing system in this way allows for improvements to the methods that may be performed with the sensing system. Additionally the absence of such complex physical structures provides greater flexibility in the types of analysis that may be performed that would otherwise be difficult to achieve.

By using a sensing system "without walls", liquids can be moved around the sensing system in a non-linear fashion. There is no need for the sample to be subjected to a specific set of processes determined by the structure of the sensing system. In the absence of fixed walls directing the flow of liquids through the sensing system, a sample may be moved to almost any point within the sensing system and thus may be exposed at will to a wide variety of environments, for example to a wide variety of different transmembrane pores. Equally, a wide variety of environments (particularly in the form of liquid droplets) may be brought to the sample.

The inventors have understood that this is particularly significant as it not only allows the sample to be sensed, but also allows experimental procedures to be performed upon the sample within the sensing system. The co-localisation of a sensing system with experimental facilities is particularly powerful as it allows an experiment or other procedure to be selected and performed based on a signal detected within the sensing system. That is, the system is flexible and can adjust its operation in response to an electrical signal detected by the sensing system.

Importantly, the process can be automated. This gives great advantages in speed compared to the operation of known systems, where a user must mentally select further experiments based on the output of a sensing system and then manually subject the sample to those further experiments.

Thus, in a first aspect, the invention provides a method of operating a sensing system, wherein the sensing system comprises:
  (i) an electrowetting device, which electrowetting device comprises:
    an array of actuation electrodes;
    an insulator layer covering the actuation electrodes and having an outermost hydrophobic surface;
    a first sensing electrode; and
    a second sensing electrode;
  (ii) disposed on the hydrophobic surface,
    a fluid medium and a first droplet and a second droplet each comprising liquid medium in the fluid medium, one of the liquid and the fluid medium being polar, and the other of the liquid and the fluid medium being apolar;
    wherein the first and/or the second droplet comprise a layer of amphipathic molecules at an interface between said first and/or second droplet and the fluid medium;
    the first droplet being in contact with the second droplet via a droplet interface; the droplet interface comprising a layer of amphipathic molecules and a first transmembrane pore; and
  (iii) a control system configured to obtain an electrical measurement from the first and second sensing electrodes, and to apply an actuation signal to the array of actuation electrodes;
wherein the method comprises
  a) obtaining an electrical measurement from the first and second sensing electrodes;
  b) analysing the electrical measurement and then selecting a droplet operation based on the electrical measurement according to one or more instructions stored in the control system; and
  a) applying an actuation signal to an actuation electrode to effect the droplet operation.

In particular, the inventors have appreciated the significant change in the scale upon which sample analysis may be performed according to the methods and using the sensing systems of the invention. The droplets of liquid which can be manipulated upon an EWOD device may be of the order of nanolitres or picolitres in size. These very small droplets can be moved rapidly around the sensing system and consequently may be analysed very rapidly. Moreover, a large number of droplets of sample may be processed at the same time in a small spatial area, meaning that the sensing system and method of the invention can provide a very large amount of data in a very short period.

In a further preferred embodiment, therefore, the invention provides a method of the invention as defined above wherein the sensing system comprises:
  disposed on the hydrophobic surface, the fluid medium and a first droplet system comprising the first droplet and the second droplet as defined herein; and
  also disposed on the hydrophobic surface, a second droplet system comprising another first droplet and another second droplet as defined herein;
wherein the method comprises performing steps (a), (b) and (c) simultaneously on the first droplet system and on the second droplet system.

The ability to manipulate droplets such as the ability to provide a third droplet, fuse a third droplet with either the second or first droplet of the droplet pair or replace a droplet with a new droplet provides a large amount of flexibility and enables species contained within the first and/or second droplets to be replaced, replenished, diluted, recovered and so on. Such species include analytes of interest, electron mediator, reaction substrates and so on.

In a further aspect, therefore, the invention provides a method wherein, disposed on the hydrophobic surface of the device are:
  an apolar fluid medium,
  a first, second and optionally a third droplet comprising a polar liquid in the fluid medium;
  the first and/or the second and/or where present the third droplet comprises a layer of amphipathic molecules at an interface between said first and/or second and/or third droplet and the fluid medium;
  the first droplet is in contact with the second droplet via a droplet interface, or the third and second droplets are each in contact with the first droplet via a droplet interface;
  the or each droplet interface comprises a layer of amphipathic molecules;
  at least one of the droplet interfaces comprises a transmembrane pore;
  the first droplet comprises an analyte;
  the second droplet comprises an electron mediator;
  the first or where present optionally the third droplet is in electrical contact with the first sensing electrode; and
  the second droplet is in electrical contact with the second sensing electrode;
the method comprising
  a) obtaining an electrical measurement from the first and second electrodes, and repeating this step a plurality of times to obtain a plurality of electrical measurements;
  b) comparing one or more of the electrical measurements with one or more of the other electrical measurements among the plurality of electrical measurements, determining an alteration in the electrical measurement detected over time that is attributable to a loss of electron mediator in the second droplet, and selecting a droplet operation to increase the concentration of electron mediator in the second droplet; and
  c) applying an actuation signal to an actuation electrode to effect the droplet operation.

The inventors have also appreciated that the flexibility permitted by the sensing system of the invention allows the same sample to be subjected to more than one sensing procedure. By way of example, an analyte present within a liquid droplet may be contacted with a first transmembrane pore and then subsequently with a second transmembrane pore, or with a first and a second transmembrane pore simultaneously. The sensing of a single sample by multiple sensing elements (e.g. transmembrane pores) can advantageously improve the accuracy with which the identity of the analyte in the sample can be determined.

Accordingly, in one aspect the invention provides a method as described herein where, disposed upon the hydrophobic surface of the EWOD device, are:
  an apolar fluid medium;
  a first, second and third droplet comprising a polar liquid medium;
  the first and/or the second and/or the third droplet comprise a layer of amphipathic molecules at an interface between said first and/or second and/or third droplet and the fluid medium;
  the first droplet being in contact with the second droplet via a droplet interface, said droplet interface comprising a layer of amphipathic molecules and a first transmembrane pore;
  the third droplet being in contact with the first or second droplet via another droplet interface, said another droplet interface comprising a layer of amphipathic molecules and a second transmembrane pore; and
  the first droplet comprising an analyte.

The invention further provides a sensing system by which the aforementioned methods may be described. Thus, the invention provides a sensing system comprising:
  an electrowetting device, which electrowetting device comprises:
    an array of actuation electrodes;
    an insulator layer covering the actuation electrodes and having an outermost hydrophobic surface;
    a first sensing electrode; and
    a second sensing electrode;
  and a control system configured to:
    obtain an electrical measurement from the first and second sensing electrodes;
    analyse the electrical measurement and then select a droplet operation based on the electrical measurement according to one or more instructions stored in the control system; and
    apply an actuation signal to an actuation electrode to effect the droplet operation.

Also provided are novel constructs of droplets of liquid medium which may be formed in and manipulated by the sensing system of the invention. The invention therefore provides a first droplet construct comprising a first, second and third droplets each comprising liquid medium, wherein:
  the first droplet comprises an analyte;
  the second and third droplets each comprise an electron mediator; and
  the first droplet contacts each of the second and third droplets via a droplet interface, wherein each droplet interface comprises a layer of amphipathic molecules.

The invention also provides a second droplet construct comprising a first, second and third droplets each comprising liquid medium, wherein:
  the first droplet contacts the second droplet via a droplet interface, which droplet interface comprises a layer of amphipathic molecules;
  the first droplet contacts the third droplet via a droplet interface, which droplet interface comprises a layer of amphipathic molecules; and
  the droplet interface between the first droplet and the second droplet, and/or the droplet interface between the first droplet and the third droplet comprises a plurality of ion channels.

The invention also provides a third droplet construct comprising a first, second and third droplets each comprising liquid medium, wherein:
  the first droplet contacts the second droplet via a droplet interface, which droplet interface comprises a layer of amphipathic molecules and a first transmembrane pore;
  the first droplet contacts the third droplet via a droplet interface, which droplet interface comprises a layer of amphipathic molecules and a second transmembrane pore; and
  the first transmembrane pore and the second transmembrane pore are different.

BRIEF DESCRIPTION OF THE FIGURES

FIG. 14 also shows that further droplets may be added to that initial system.

DETAILED DESCRIPTION OF THE INVENTION

Sensing System

Figure 1:
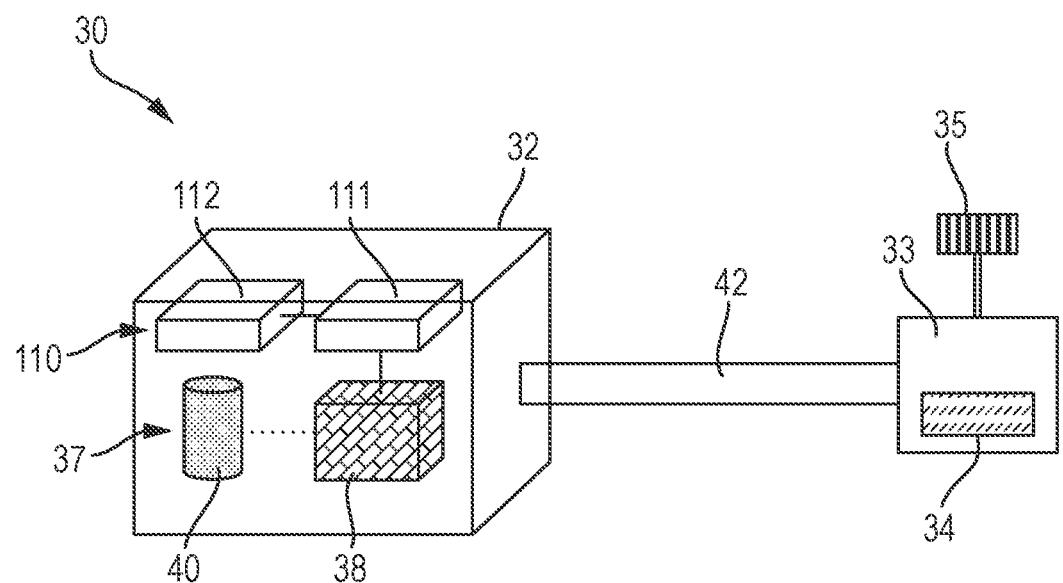
FIG. 1 is a schematic view of an apparatus including an AM-EWOD device.

The sensing system comprises an electrowetting device as described herein and a control system as defined herein. The sensing system optionally also comprises a fluid medium and a first droplet and a second droplet each comprising liquid medium. The sensing system typically comprises the fluid medium and droplets of liquid medium when the sensing system is in use.

It should be understood that the sensing system as described herein is both the sensing system of the invention and the sensing system used in the method of the invention. Accordingly, the features of the sensing system mentioned hereafter are applicable to the sensing system and the method of operating a sensing system according to the invention.

Electrowetting (EWOD) device Electrowetting is the phenomenon whereby the application of an electric field to a liquid on a surface modifies the wetting behaviour of the liquid on the surface. Electrowetting enables liquid droplets to be manipulated on a surface by the application of an electrical field, for example to be re-shaped or moved. The EWOD device of the invention makes use of this phenomenon to provide a versatile sensing system suitable for analysing droplets of liquid.

The EWOD device typically comprises an active matrix and may therefore be referred to as an AM-EWOD device.

The EWOD device comprises an array of actuation electrodes. The array of actuation electrodes comprises at least two electrodes, but typically comprises at least 10 electrodes, at least 100 electrodes, or at least 1,000 electrodes, at least 10,000 electrodes, at least 100,000 electrodes, or at least 1,000,000 electrodes. For example, the array of actuation electrodes typically contains in the region of 10 to 107 actuation electrodes, for instance from $10^2$ to $10^6$ actuation electrodes. The actuation may be arranged in any pattern but are typically arranged in an approximately rectangular arrangement, comprising parallel rows of actuation electrodes.

The actuation electrodes may be formed of any electrically conductive material, for example a metal or a transparent metal oxide, e.g. Indium tin oxide (ITO).

The actuation electrodes can be used to manipulate a droplet on the hydrophobic surface of the EWOD device, making use of the electrowetting phenomenon. When an actuation signal is applied to an actuation electrode among the array of actuation electrodes, the actuated electrode can attract a droplet of polar liquid or repel a droplet of apolar liquid. Thus, the actuation electrodes can be used, for example, to change a droplet's shape or to move a droplet. Such droplet operations are discussed in more detail below.

Accordingly, the actuation electrodes are configured to receive actuation signals for electro-wetting droplets. The control system controls the actuation signals applied to the actuation electrodes. The actuation electrodes can be individually controllable by the control system. Accordingly, the control system may apply an actuation signal to one or more electrodes within the electrode array.

The EWOD device may further comprise an active matrix arrangement connected to the actuation electrodes.

The array of actuation electrodes and where present the active matrix arrangement are typically supported by a first substrate. The material of the first substrate is not particularly insulating; its function is to provide a solid support to the device. Typically, the first substrate is made of an insulating material. In some embodiments, the EWOD device further comprises a layer of thin film electronics. The thin film electronics are capable of applying actuation signals to the actuation electrodes under the direction of the control system. The thin film electronics may therefore be regarded as part of the control system of the EWOD device. The thin film electronics may be disposed between the array of actuation electrodes and the first substrate in the EWOD device.

The actuation electrodes are connected to the control system in order that the control system may apply actuation signals to one or more electrodes in the array of actuation electrodes. The actuation electrodes may be connected to the control system via the thin film electronics.

The EWOD device comprises an insulator layer covering the array of actuation electrodes. By "covering" is meant that, in operation of the sensing system, the insulator layer is situated between the array of actuation electrodes and the fluid medium (and the first and second droplets of liquid medium also). The insulator layer is a layer of electrically insulating material. The thickness of the insulator layer is not particularly limited; typically, the insulator layer is 0.1 to 500 microns thick.

The insulator layer does not prevent the application of an electric field across the insulator layer into the fluid medium (where present). However, the insulator layer usually prevents electrical contact between the actuation electrodes and the fluid and liquid media.

Typically, the insulator layer comprises a layer of electrically insulating material coated by a hydrophobic material that forms said hydrophobic surface. By "outermost hydrophobic surface" is meant that the hydrophobic surface is capable of directly contacting fluid and liquid media when they are placed in the sensing system. The hydrophobic surface may be formed of any hydrophobic material.

Thus, the EWOD device typically comprises, in order: a first substrate; thin film electronics; an array of actuation electrodes; an insulator layer and an outermost hydrophobic surface. The EWOD device may of course comprise further layers and components interspersed between those components.

The EWOD device further comprises at least two sensing electrodes. These electrodes are configured to make electrical contact with the first droplet and/or the second droplet and/or where present the third droplet. By "configured to make electrical contact" is meant that the at least two sensing electrodes may directly contact the aforementioned droplets, or that the at least two sensing electrodes may contact the aforementioned droplets via an electrically conducting material.

In a preferred embodiment, the electrowetting device further comprises a second substrate facing the hydrophobic surface of the insulator layer, wherein the second substrate is coated by a hydrophobic material forming a further hydrophobic surface facing the hydrophobic surface of the insulator layer. In this embodiment, the droplets may be disposed on the further hydrophobic surface of the hydrophobic layer as well as the hydrophobic surface of the insulator layer. In this manner, the droplets are sandwiched between the two substrates, which constrains the shape of the droplets. This improves the degree of control of the shape of the droplets between the energised state and lower energy state, which in turn improves the reliability of the formation of droplet interfaces.

In a further preferred aspect of this embodiment, the second substrate may support the first and the second sensing electrode. For example, the second substrate may support one or more arrays of sensor electrodes (including the first and second sensing electrodes) that are configured to make an electrical connection with the droplets between which a droplet interface is formed. An array of sensor electrodes comprises at least the first and second sensing electrodes. This embodiment is advantageous as it does not require the actuation electrodes to perform a second function: that of detecting electrical signals.

In this aspect, the first and second sensing electrodes (e.g. an array of sensing electrodes comprising the first and second sensing electrodes) are provided on a second substrate facing the hydrophobic surface of the insulator layer that covers the actuation electrodes. This provides a convenient and reliable way to make electrical connections to the droplets.

The second substrate may be coated by a hydrophobic material forming a further hydrophobic surface facing the hydrophobic surface of the insulator layer. By "coated" is meant that the hydrophobic material is disposed on second substrate; however, there may be intervening species, for instance the sensing electrodes may be disposed between the second substrate and the said hydrophobic material coating the second substrate. In that case, the electro-wetting device may be arranged to receive the fluid medium and the droplets disposed on the further hydrophobic surface of the hydrophobic layer as well as the hydrophobic surface of the insulator layer. In this manner, the droplets are sandwiched between the two substrates, which constrains the shape of the droplets. As explained above, this improves the degree of control of the droplets by actuation signals applied to the actuation electrodes.

Where the second substrate is coated by a hydrophobic material and the sensing electrodes are disposed on the second substrate, then the hydrophobic material coating the second substrate may have apertures exposing at least part of the first and second sensing electrodes. This improves the electrical connection between the sensing electrodes and the droplets. The hydrophobic material coating the second substrate may be referred to as a second outermost hydrophobic surface.

Thus, in a preferred embodiment, the EWOD device comprises, in order: a first substrate; thin film electronics; an array of actuation electrodes; an insulator layer; an outermost hydrophobic surface; a spacer; a hydrophobic material; a first and second sensing electrode; and a second substrate. The EWOD device may of course comprise further layers and components interspersed between those components. In this embodiment the spacer provides a cavity between the two hydrophobic material layers in which fluid medium and liquid medium may be received.

The second substrate may also support at least one further electrode, for example for receiving a reference signal while actuation signals are applied to the actuation electrodes for manipulating the droplets. The sensing electrodes and the further electrodes, where provided, may be deposited on a surface of the second substrate facing the first substrate. In that case, the further electrodes, where provided, may extend around the sensing electrodes.

The EWOD device may further include a droplet preparation system configured to form droplets disposed on the hydrophobic surface of the electro-wetting device in the fluid medium. In this case, the control system may be configured to control the droplet preparation system to form the droplets. This increases the experimental power of the apparatus as it allows droplets containing appropriate reagents to be formed for experimental purposes.

An exemplary overall apparatus is illustrated in FIG. 1 and described below.

Figure 2:
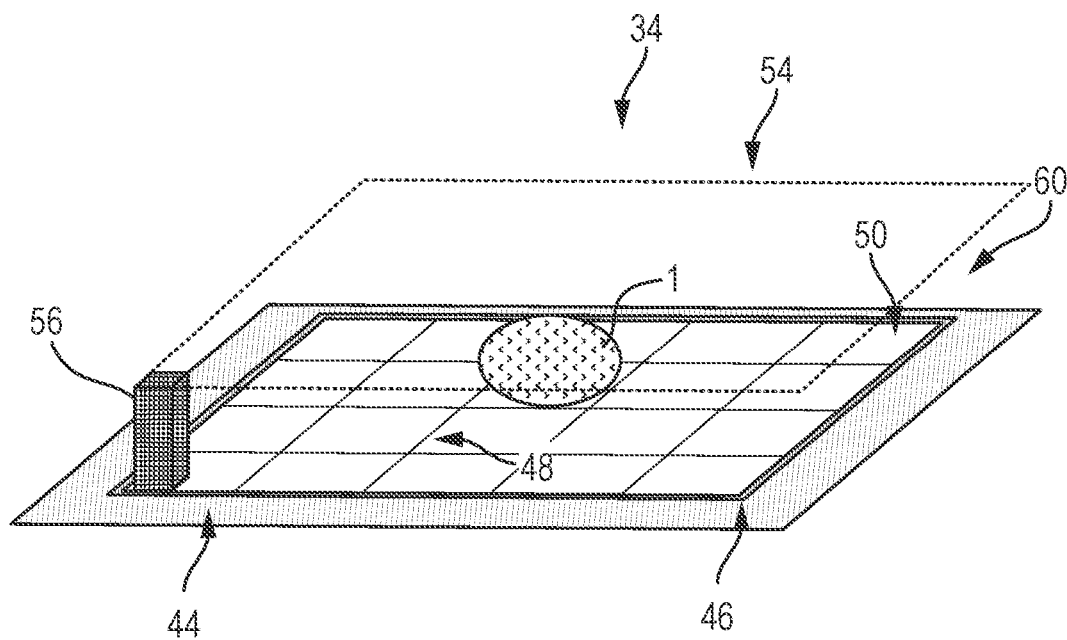
FIG. 2 is a schematic perspective view of the AM-EWOD device.

FIG. 1 illustrates an apparatus 30 containing the sensing system of the invention. The apparatus 30 includes a reader 32 and a cartridge 33 that may be inserted into the reader 32. The cartridge 33 contains an AM-EWOD device 34 which is an example of an electro-wetting device. The AM-EWOD device 34 is shown in FIG. 2 and described further below.

The reader 32 and cartridge 33 may be electrically connected together while in use, for example by a cable of connecting wires 42, although various other methods (e.g. wireless connection) of providing electrical communication may be used.

The reader 32 also comprises a droplet preparation system 35 configured to form droplets 1 comprising liquid in a fluid medium 60 in the AM-EWOD device 34 when the cartridge 33 is inserted. Suitable material properties for the droplets 1 and the fluid medium 60 are discussed herein. The droplet preparation system 35 may also be able to carry sample preparations to prepare an analyte to be measured, alternatively sample preparation may be carried out in the AM-EWOD device 34. The samples may be compartmentalised for a library preparation or for sequencing.

The droplet preparation system 35 may comprise fluid input ports that perform the function of inputting liquid into the AM-EWOD device 34 from one or more reservoirs and thereby generating droplets within AM-EWOD device 34. The droplet preparation system 35 may be formed by conventional fluidics elements, for example controlling flow of liquid by electro-wetting. The droplet preparation system 35 desirably has the ability to accurately control the volumes of created droplets 1, typically accurate to 2-3%.

The apparatus 30 further includes a control system 37 provided in the reader 32. In this example, the control system 37 includes control electronics 38 and a storage device 40 that may store any application software any data associated with the system. The control electronics 38 may include suitable circuitry and/or processing devices that are configured to carry out various control operations relating to control of the AM-EWOD device 34, such as a CPU, microcontroller or microprocessor.

Among their functions, to implement the features of the present invention, the control electronics 38 may comprise a part of the overall control system 37 that may execute program code embodied as a control application within the storage device 40. The storage device 40 may be configured as a non-transitory computer readable medium, such as random access memory (RAM), a read-only memory (ROM), an erasable programmable read-only memory (EPROM or Flash memory), or any other suitable medium. Also, while the code may be executed by control electronics 38 in accordance with an exemplary embodiment, such control system functionality could also be carried out via dedicated hardware, firmware, software, or combinations thereof.

As described in more detail below, the control system 37 is configured to perform control of various elements of the sensing system. This optionally includes control of the droplet preparation system 35 where present, to form the droplets 1. The control system is also connected to the sensing electrodes, and is configured to operate the sensing electrodes to take electrical measurements and to process the electrical measurements. The control system is further configured to select a droplet operation and to control the application of actuation signals for manipulating droplets. In particular, the control system 37 is configured to manipulate droplets in the sensing system in response to the electrical measurements, for instance the control system is capable of forming one or more systems of a first droplet and a second droplet connected via a droplet interface. The control system 37 may also provide a graphical user interface (GUI) to a user which provides for the user to input of program commands. Exemplary commands include, for instance, whether or not to proceed with a suggested droplet operation, or the selection of an assay to be performed. The GUI also provides for displaying the results of such operations to the user.

Figure 3:
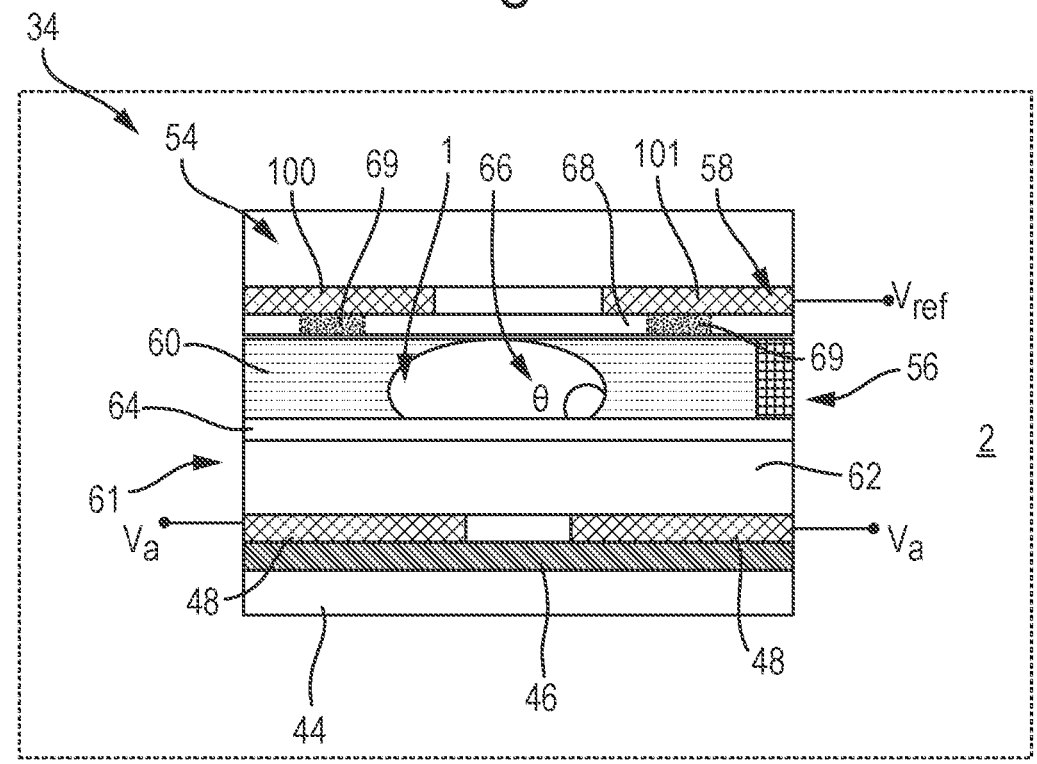
FIG. 3 is a cross-sectional side view of a portion of the AM-EWOD device.

FIG. 2 and FIG. 3 illustrate the AM-EWOD device 34. FIG. 3 relates to the preferred embodiment wherein the EWOD device comprises a second substrate, and the first and second sensing electrodes are disposed on the second substrate.

As seen in FIG. 2, the AM-EWOD device 34 has a first substrate 44 (which is the lowermost substrate in FIGS. 2 and 3) with thin film electronics 46 disposed upon the first substrate 44. An array 50 of actuation electrodes 48 are supported by the first substrate 46 on top of the thin film electronics 46. The thin film electronics 46 are arranged to drive the actuation electrodes 48.

The array 50 of actuation electrodes 48 may be an X by Y rectangular array, where X and Y are any integers. The actuation electrodes 48 may be formed, for example, from indium tin oxide (ITO) or another transparent metal oxide, or a metal, or any other electrically conductive material.

The AM-EWOD device 34 also includes a second substrate 54 (which is the uppermost substrate in FIGS. 2 and 3) separated by a spacer 56 from the first substrate 44. As described further below, the first and second droplets are disposed between the first substrate 44 and a second substrate 54. A single droplet, 1, is shown in FIGS. 2 and 3 but at least a first and second droplets are present during operation of the sensing system according to the method of the invention.

The layered structure of the AM-EWOD device 34 is best seen in FIG. 3 which illustrates a portion thereof including two actuation electrodes 48 supported by the first substrate 44. The actuation electrodes 48 may be formed from a patterned layer of conductive material. An insulator layer 61 comprising a layer 62 of electrically insulating material coated by a hydrophobic material 64 is disposed on the first substrate 44, covering the actuation electrodes 48. The hydrophobic material 64 forms an outermost hydrophobic surface of the insulator layer 61.

The second substrate 54 faces the hydrophobic surface of the insulator layer 61. The second substrate 54 supports a layer 58 of conductive material that is deposited on the surface of the second substrate 54 facing the insulator layer 61. The layer 58 of conductive material is patterned to form more electrodes. The second substrate 54 is coated by a hydrophobic material 68 that covers the layer 58 of conductive material and forms a further hydrophobic surface facing the hydrophobic surface of the insulator layer 61 The hydrophobic materials 64 and 68 may be formed by any suitable materials (which may be the same or different), for example a fluoropolymer.

The sensing system of the invention is shown comprising a droplet 1 in the AM-EWOD device 34, disposed within a fluid medium 60. The droplets 1 and the fluid medium 60 are disposed on the hydrophobic surface of the insulator layer 61 and on the further hydrophobic surface of the hydrophobic material 68 that coats the second substrate 54. In this manner, the droplets 1 are sandwiched between the first and second substrates 44 and 54, which constrain the shape of the droplets 1. This improves the degree of control of the droplets 1 by the actuation signals applied to the actuation electrodes 48 in the manner described below.

The droplets 1 have a contact angle 66 with the hydrophobic surface of the insulator layer 61. The contact angle 66 is determined by the balancing of the surface tension components (1) from the hydrophobic surface to the liquid of the droplets 1 ($\Gamma_{SL}$) interface, (2) from the liquid of the droplets 1 to the surrounding fluid medium 60 ($\Gamma_{LG}$) interface, and (3) from the hydrophobic surface to the surrounding fluid medium 60 ($\Gamma_{SG}$) interface. Where no voltages are applied, the contact angle 66 satisfies Young's law, and is of size $\theta$ given by the equation $$\cos\theta = ((\Gamma_{SG} - \Gamma_{SL})/\Gamma_{LG}).$$

Accordingly, the actuation electrodes 48 are capable of electro-wetting the droplets 1 when actuation signals are applied to the actuation electrodes 48. When an actuation signal is applied to a droplet, it may be referred to as an actuated droplet. The actuation signals create electrical forces that effectively control the hydrophobicity of the hydrophobic surface of the insulating layer 61, and thereby energise the droplet 1. In such an energised state, the droplets 1 will have a shape that is modified compared to when the droplets 1 are in a lower energy state, i.e. a state in which the actuation signals provide less or no energy to the droplets 1.

Such references to the shape being modified may refer to the shape in the plane of the AM-EWOD device 34, i.e. parallel to the hydrophobic surface of the insulator layer 61. Although energy supplied by the actuation signals will modify the three-dimensional shape of the droplets 1, the shape is most greatly affected in the plane of the AM-EWOD device 34, being the direction in which the actuation electrodes 48 are arrayed.

By selective control of the pattern of actuation signals applied to one or more selected actuation electrodes 48 among the array of actuation electrodes, the droplets 1 may be manipulated and moved in the lateral plane between the first and second substrates 44 and 54. In general terms, such manipulation of droplets 1 in this manner may apply techniques known for EWOD devices.

The actuation signals may take any form suitable for electro-wetting the droplets 1. Typically, the actuation signals may be AC actuation signals, but in general they could also be DC voltage potentials with respect to a reference voltage. While applying the actuation signals, a reference signal is applied to a reference electrode 59 elsewhere in the AM-EWOD device, as described further below.

The reference signal may take any suitable form. In one example, the reference signal may be a fixed reference voltage. In another example where the actuation signals are AC actuation signals, the reference signal may be an AC reference signal which is in anti-phase with the AC actuation signals. In this example, the magnitude of the potential difference between the actuation electrodes 48 and the reference electrode 59 is increased, for example being doubled when the AC actuation signals and the AC reference signal are of equal magnitude, compared to a reference signal that is a fixed reference voltage.

Figure 4A:
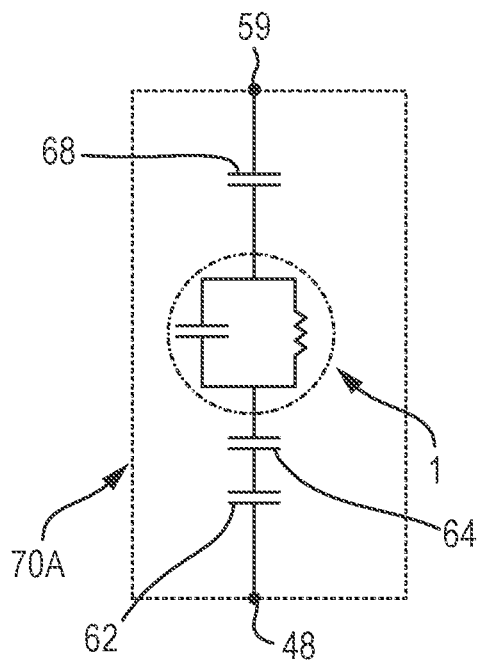
FIGS. 4A and 4B are diagrams of a circuit representation of the electrical load presented at the actuation electrode when a liquid droplet is present and not present, respectively.
Figure 4B:
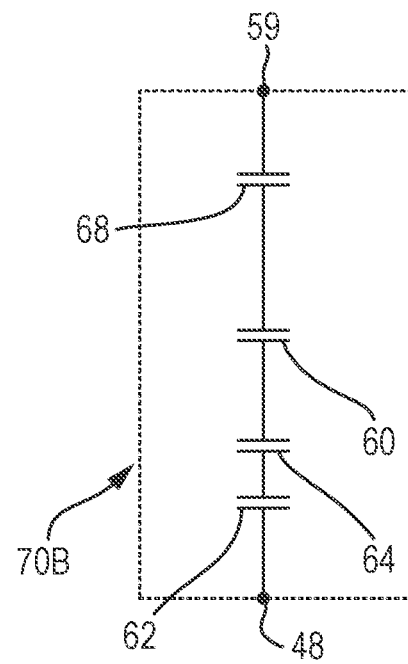
Figure 5:
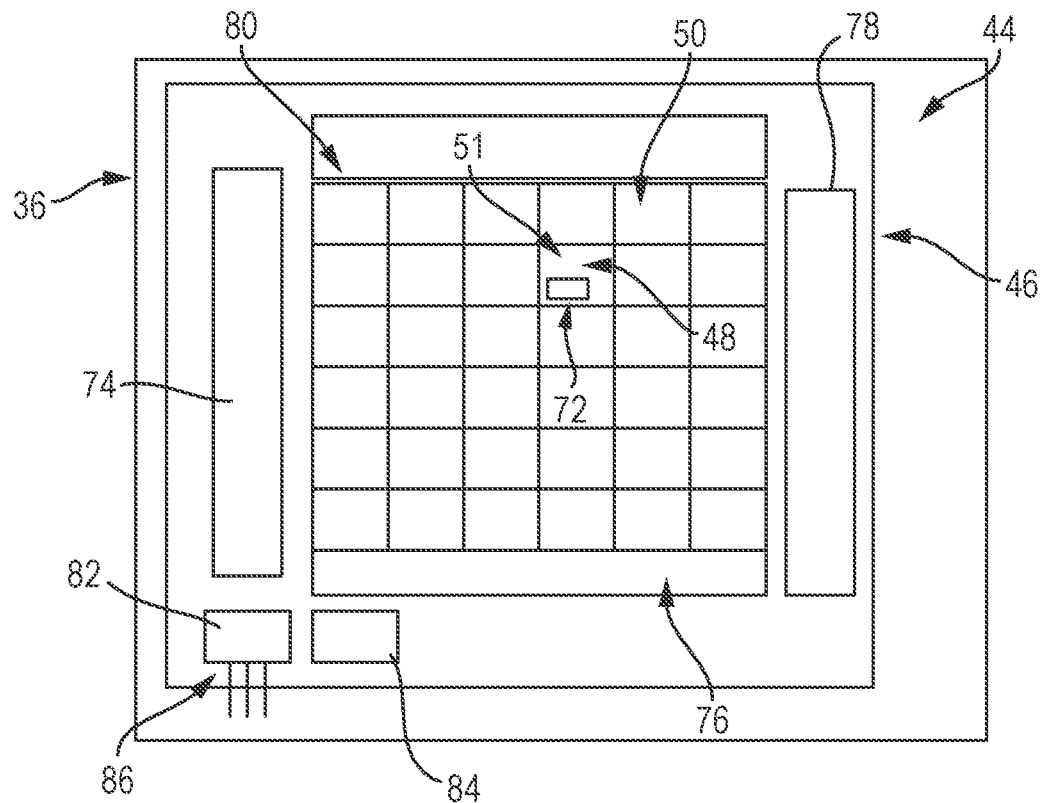
FIG. 5 is a plan view of thin film electronics in the AM-EWOD device.
Figure 6:
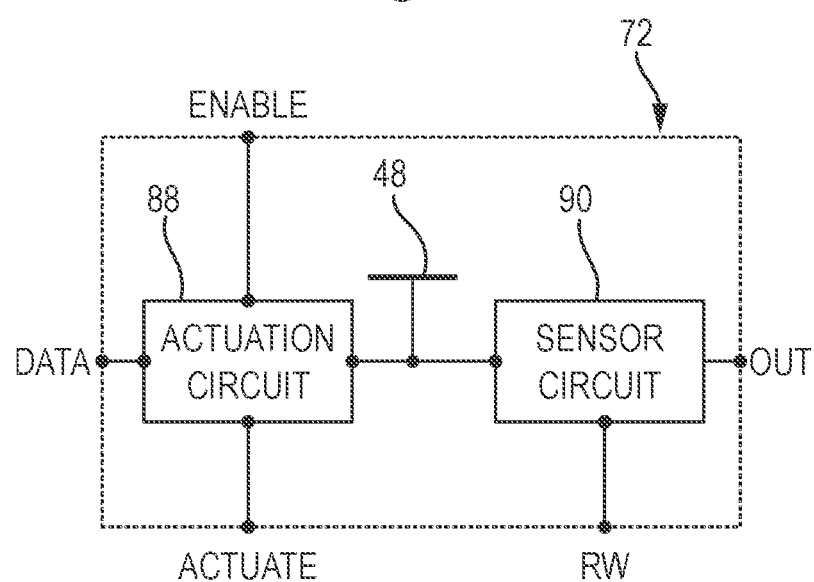
FIG. 6 is a diagram of an array element circuit of the AM-EWOD device.

The operation of the electrodes of the electrowetting device is illustrated in FIGS. 4 to 6.

FIG. 4A shows a simplified circuit representation of the electrical load 70A between the actuation electrode 48 and a reference electrode 59 in the case where a droplet 1 is present. The droplet 1 can usually be modelled as a resistor and capacitor in parallel. Typically, the resistance of the droplet 1 will be relatively low (e.g. if the droplet contains ions) and the capacitance of the droplet will be relatively high (e.g. because the relative permittivity of polar liquids is relatively high, e.g. ~80 if the droplet 1 is aqueous). In many situations the droplet resistance is relatively small, such that at the frequencies of interest for electro-wetting, the droplet 1 may function effectively as an electrical short circuit. The hydrophobic materials 64 and 68 have electrical characteristics that may be modelled as capacitors, and the insulating material of the layer 62 may also be modelled as a capacitor. The overall impedance between the actuation electrode 48 and the reference electrode 59 may be approximated by a capacitor whose value is typically dominated by the contribution of the insulating material of the layer 62 and hydrophobic materials 64 and 68 contributions, and which for typical layer thicknesses and materials may be on the order of a pico-Farad in value.

FIG. 4B shows a circuit representation of the electrical load 70B between the actuation electrode 48 and the reference electrode 59 in the case where no droplet 1 is present. In this case the droplet components are replaced by a capacitor representing the capacitance of the non-polar fluid 60 which occupies the space between the top and first substrates. In this case the overall impedance between the actuation electrode 48 and the reference electrode 59 may be approximated by a capacitor whose value is dominated by the capacitance of the non-polar fluid and which is typically small, of the order of femto-Farads.

For the purposes of driving and, where applicable, sensing the actuation electrodes 48, the electrical loads 70A and 70B overall function in effect as a capacitor, whose value depends on whether a droplet 1 is present or not at a given actuation electrode 48. In the case where a droplet is present, the capacitance is relatively high (typically of order pico-Farads), whereas if there is no droplet 1 present the capacitance is low (typically of order femto-Farads). If a droplet partially covers a given electrode 48 then the capacitance may approximately represent the extent of coverage of the actuation electrode 48 by the droplet 1.

FIG. 5 illustrates the arrangement of the thin film electronics 46 in the AM-EWOD device 34. The thin film electronics 46 is located on the first substrate 44 and comprises an active matrix arrangement of array elements 51 each comprising an array element circuit 72 for controlling the electrode potential of a corresponding actuation electrode 48. Integrated row driver 74 and column driver 76 circuits are also implemented in thin film electronics 46 to supply control signals to the array element circuit 72. In this manner, the array element circuit 72 may perform a function of selectively, under the control of the control system 37, actuating the actuation electrode 48 to apply an actuation signal to the actuation electrode 48. Thus, the control system 37 controls the actuation signals applied to the actuation electrodes 48, such as required voltage and timing signals to perform droplet manipulation operations.

FIG. 6 illustrates the arrangement of the array element circuit 72 present in each array element 51. The array element circuit 72 contains an actuation circuit 88, having inputs ENABLE, DATA and ACTUATE, and an output which is connected to an actuation electrode 48. A serial interface 82 may also be provided to process a serial input data stream and facilitate the programming of the required voltages to the actuation electrodes 48 in the array 50. A voltage supply interface 84 provides the corresponding supply voltages, second substrate drive voltages, and other requisite voltage inputs. A number of connecting wires 86 between the first substrate 44 and external control electronics, power supplies and any other components can be made relatively few, even for large array sizes. Optionally, the serial data input may be partially parallelized. For example, if two data input lines are used the first may supply data for columns 1 to X/2, and the second for columns (1+X/2) to M with minor modifications to the column driver circuits 76. In this way the rate at which data can be programmed to the array elements 51 is increased, which is a standard technique used in Liquid Crystal Display driving circuitry.

Figure 7:
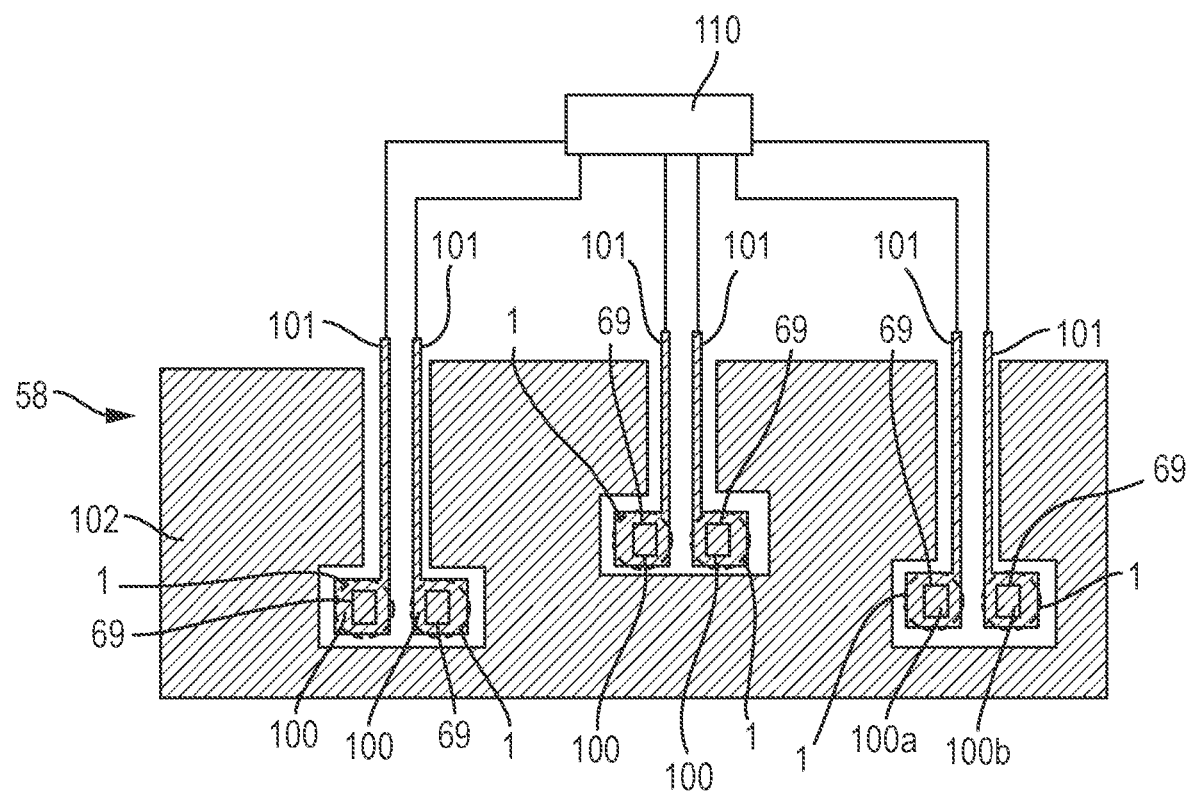
FIG. 7 is a plan view of a layer of conductive material formed on a second substrate of the AM-EWOD device.

FIG. 7 shows an exemplary aspect of the preferred embodiment of the invention wherein the first and second sensing electrodes are not among the array of actuation electrodes but are supported on a second substrate. In this embodiment, FIG. 7 shows how the layer 58 of conductive material may be patterned to form sensor electrodes 100, conductive tracks 101, and further electrodes 102 which are deposited on the second substrate 54 and supported thereby.

The sensor electrodes 100 are arranged to make an electrical connection with respective droplets 1. The provision of the sensing electrodes 100 is a convenient and reliable way to make electrical connections to the droplets 1. In contrast, such a type of electrical connection is not possible from the actuation electrodes 58 due to the presence of the insulating layer 61 including layer 62 of electrically insulating material between the actuation electrodes 48 and the droplets 1.

The hydrophobic material 68 that covers the layer 58 of conductive material coating the second substrate 54 is provided with apertures 69 that expose part of the sensing electrodes 100, although more generally the apertures may be larger and expose the entirety of the sensing electrodes 100. The apertures 69 in the hydrophobic material 68 assist in making an electrical contact between the sensing electrodes 100 and the droplets 1. The fluid medium 60 and/or the liquid of the droplets 1 can flow into apertures 69, and have a lower electrical impedance than the hydrophobic material 68, thereby providing a conductive path. Such apertures 69 may have the additional advantage of acting as a hydrophilic patch which helps to pin droplets 1 in position if the electrodes are de-actuated or the device is de-powered. Such apertures 69 may be created by selective removal of the hydrophobic material 68, for example by means of a dry etch process or lift off process.

However, the apertures 69 are not essential and instead an electrical connection between the sensing electrodes 100 and the droplets 1 can be made through the hydrophobic material 68, which may be of sufficiently low impedance (either real or imaginary parts) that an electrical measurement can still be taken through it. In that case, the thickness and material properties of the hydrophobic material 68 are chosen accordingly.

The EWOD device comprises a first sensing electrode and a second sensing electrode. Typically, the EWOD device comprises an array of sensing electrodes comprising a plurality of sensing electrodes, arranged in sets of two. The sensing electrodes 100 shown in FIG. 7 are arranged in sets, each set comprising a first electrode and a second electrode. The first sensing electrode and the second sensing electrode respectively are indicated as 100a and 100b, being any two of the array of sensing electrodes. The sensing electrodes 100 of each set may be sized and shaped to make an electrical connection with droplets 1 between which a droplet interface is formed. This may be achieved by the area of the first and second sensing electrodes being similar to the area enclosed by the droplets of interest (e.g. the first and second droplets) upon the hydrophobic surface of the second substrate. Additionally, the distance between the centres of the first and second sensing electrodes within a set of sensing electrodes 100 may be similar to the distance between the centres of the droplets 1 across which the electrical measurement is to be taken. This is shown in FIG. 7, wherein two droplets (1) are shown by dotted lines, their centres each arranged over the centre of a first and second sensing electrode respectively 100a, 100b within a set of two sensing electrodes 100. Thus, each set of sensor electrodes 100 may be aligned with a respective system of droplets 1 for making electrical connections to respective droplets 1 in that system of droplets 1.

FIG. 7 shows that, in operation, the sensing system may contain plural systems of two or more droplets 1, where each system of droplets 1 is aligned with a respective set of sensing electrodes 100. By way of illustration, FIG. 7 shows an array of sensing electrodes comprising three sets of two sensing electrodes 100; and three systems of two droplets 1 formed in alignment with the sensor electrodes 100 of the respective sets. However, in general, there could be any number of sets of sensing electrodes 100, and the sets could contain any number of sensing electrodes 100 in dependence in the number of droplets 1 to be included in each system. Typically, the array of sensing electrodes comprises at least 10, or at least 100, or at least 1,000, or at least 10,000, or at least 1,000,000 electrodes. In some embodiments, the array of sensing electrodes comprises in the region of 10 to 107 sensing electrodes, for example 100 to $10^6$ sensing electrodes.

As a result of this configuration, systems of two droplets such as a first droplet and a second droplet 1 may be formed in parallel and experiments may be performed thereon in parallel using the respective sets of sensing electrodes 100a, 100b. In general any number of systems of droplets 2 may be formed, for example two or more, up to large numbers of order tens of thousands.

The conductive tracks 101 are connected to the sensor electrodes 100 and extend to the edge of the layer 58 of conductive material where an electrical connection is made to the control system 37; specifically the droplet interface system sensor system 110. Thus, the conductive tracks 101 provide an electrical connection from the sensing electrodes 100 to the control system 37.

A further electrode 102 can extend around the sensing electrodes 100 and the conductive tracks 101. The further electrode 102 may function as the reference electrode 59 in the circuit representations shown in FIGS. 4A and 4B. In that case, the control system 37 is connected to the further electrode 102 and is arranged to apply a reference signal to the further electrode 102, while applying actuation signals to the actuation electrodes 48.

However, the further electrode 102 is not essential. When the further electrode 102 is absent, or even when the further electrode 102 is present, a different electrode(s) may function as the reference electrode 59. In one example, the sensing electrodes 100 may function as the reference electrode 59.

In another example, a reference electrode 59 may be provided elsewhere between the first and second substrates 44 and 54, for example as a separate element such as an in-plane reference electrode. In any such example, the control system 37 is connected to the reference electrode 59, e.g. the sensor electrodes 100, and is arranged to apply a reference signal to the reference electrode 59, while applying actuation signals to the actuation electrodes 48. In such an arrangement, unactuated actuation electrodes 48 on the first substrate 44 may operate as a reference and droplets 1 can be moved without needing a reference electrode on the second substrate 54.

The control system 37 in the reader 32 may further comprise a droplet interface sensor system 110 including a measurement unit 111 which is connected to the sensing electrodes 100 and takes electrical measurements between sensing electrodes 100 that are electrically connected to respective droplets 1, across droplet interfaces formed therebetween. The measurement unit 111 is typically controlled to take electrical measurements out while actuation signals are not applied to the actuation electrodes 48. This has the advantage of reducing the risk of the actuation signals affecting the electrical measurements, for example by physically affecting or damaging the system of droplets being measured or by causing electrical interference with the measurement unit 111.

The elements of the thin film electronics 46 are electrically isolated from the sensor electrodes 100 and the measurement unit 111, so do not participate in taking of the electrical measurements.

The control system 37 (for instance the droplet interface sensor system 110 within the control system) may further comprise an analysis system 112 configured to process the electrical measurements that are dependent on an analyte that interacts with a transmembrane pore, in order to analyse the analyte. For example, where the analyte is a polymer comprising polymer units, the analysis system may be configured to process the electrical measurements to derive estimated identities of the polymer units of the polymer. The analysis system 112 may process the electrical measurements using any suitable known technique.

The analysis system 112 may be formed by an appropriate combination of (1) a hardware stage, for example a field programmable gate array (FPGA), to pre-process the electrical measurements supplied as a signal from the measurement unit 111, and (2) a processor for processing the signals supplied from the hardware stage. The processor may be any suitable form of processing device. The processor may be implemented within the reader 32 as shown in FIG. 1, and may execute software which may be stored in the storage device 40. As an alternative, the processor could be implemented by a processing device, for example a conventional computer apparatus, external to the reader 32.

By way of example, the measurement unit 111 and the analysis system 112 may have the same construction as the signal processing function described in WO-2011/067559.

The droplet interface sensor system 110 may be combined with other types of measurement system to take measurements, for example capacitance measurements from the actuation electrodes, and/or measurements from additional electrodes (not shown).

The array element circuit 72 also may contain a droplet sensor circuit 90, which is in electrical communication with the actuation electrode 48. The droplet sensor circuit 90 provides a sensing capability for detecting the presence or absence of a droplet 1 in the location of each actuation electrode 48. In this manner, the array element circuit 72 may also perform a function of sensing the presence or absence of a droplet 1 at the location of the array element 51 during manipulation of the droplets 1. However, due to the presence of the insulating layer 61 including layer 62 of electrically insulating material between the actuation electrodes 48 and the droplets 1, it may be difficult or inconvenient to take electrical measurements suitable for studying a droplet interface or processes occurring at a droplet interface.

The droplet sensor circuit 90 may conveniently employ capacitive sensing using an impedance sensor circuit. The droplet sensor circuit 90 may include impedance sensor circuitry of the type known in the art, as described for example in U.S. Pat. No. 8,653,832 and GB-2,533,952. As described therein, droplets 1 may be actuated by means of electro-wetting and may be sensed by capacitive or impedance sensing means. Typically, capacitive and impedance sensing may be analogue and may be performed simultaneously, or near simultaneously, at every array element 51. By processing the returned information from such a sensor (for example in the application software in the storage device 40 of the reader 32), the control system 37 can determine in real-time, or almost real-time the position, size, centroid and perimeter of each droplet 1 present in the AM-EWOD device.

Alternatively, such sensing may be performed by some other means, for example optical or thermal means. An alternative to the droplet sensor circuit 90 is to provide an external sensor such as an optical sensor that can be used to sense droplet properties, as is known in the field of electro-wetting devices.

The control system 37 generates and outputs control signals for the droplet sensor circuit 90 to perform sensing operations during manipulation of the droplets 1. Integrated sensor row addressing 78 and column detection circuits 80 are implemented in the thin film electronics 46 for the addressing and readout of the droplet sensor circuit 90 in each array element circuit 72. Typically, the read-out of the droplet sensor circuit 90 may be controlled by one or more addressing lines (e.g. RW) that may be common to array elements 51 in the same row of the array 50, and may also have one or more outputs, e.g. OUT, which may be common to all array elements 50 in the same column of the array 50.

The control system 37 may use the output of the of the droplet sensor circuit 90 to control the timing of the application of actuation signals to the actuation electrodes 48 when manipulating droplets 1.

Control System

The control system performs a variety of functions. The control system operates the sensing electrodes to take electrical measurements, processes the electrical measurements taken and selects droplet operations, and operates the actuation electrodes to effect the droplet operations.

The control system is connected to the first and second sensing electrodes and is configured to take electrical measurements, for example including impedance measurements, between the first and second sensing electrodes. Where the sensing system comprises an array of sensing electrodes, the control system may be configured to take electrical measurements, for example impedence measurements, between any two sensing electrodes among the array of sensing electrodes. For instance, the control system may be configured to detect the location of the first droplet and/or the second droplet (and/or, where present, a third or further droplet) before selecting an appropriate pair of sensing electrodes among the array of sensing electrodes at which to perform an electrical measurement.

The control system is capable of taking electrical measurements between (i.e. obtaining electrical measurements from) sensing electrodes that are electrically connected to two droplets.

Figure 8:
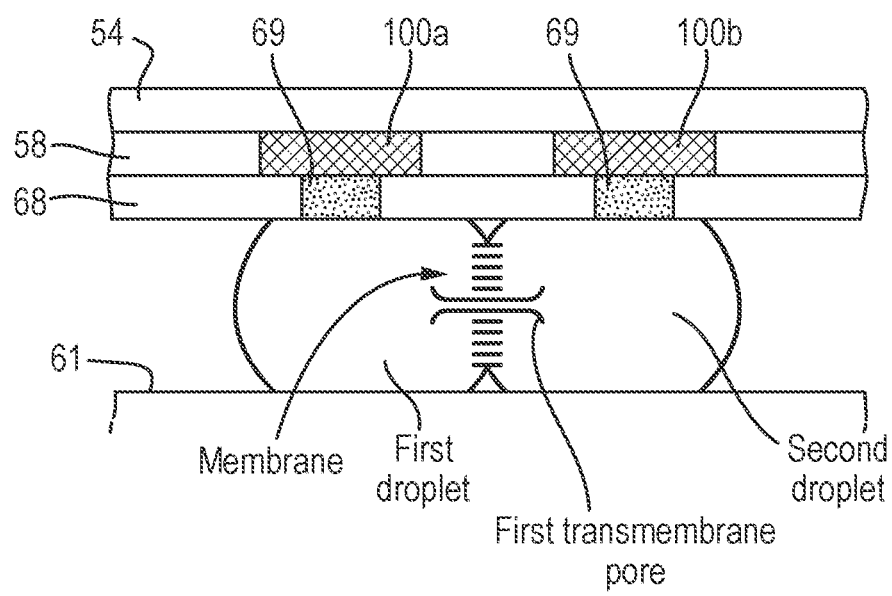
FIG. 8 is an illustration of a two-droplet construct in the sensing system of the invention.

The control system is configured to take electrical measurements between the first sensing electrode and the second sensing electrode. In one aspect, the control system is configured to take electrical measurements between the first and second sensing electrodes where the first and second sensing electrodes are each in electrical contact with a droplet. In one embodiment of this aspect, the control system is configured to take electrical measurements between the first and second sensing electrodes where the first and second sensing electrodes are each in contact with a droplet, and those droplets are connected by one or more droplet interfaces, each droplet interface comprising a layer of amphipathic molecules and a transmembrane pore. In a typical embodiment, the control system is configured to take electrical measurements between the first and second sensing electrodes where the first and second sensing electrodes are in contact with the first and second droplet respectively. This arrangement is shown in FIG. 8.

Having obtained an electrical measurement, the control system is configured to analyse the electrical measurement and then select a droplet operation based on the electrical measurement according to one or more droplets stored in the control system.

In one aspect the control system is configured to select a droplet operation to achieve an outcome specified by the user or stored within the control system. For example, the control system may be configured to select a droplet operation according to one or more instructions stored in the control system wherein said instructions are instructions for analysing an analyte; and/or performing an assay; and/or performing an experiment upon a sample in the system.

The steps occurring within the control system to allow the selection of a droplet operation according to the method of the invention are as described below. The control system typically comprises what may be referred to as an "operation system", wherein the operation system stores one or more instructions and optionally further information regarding the sensing system.

The operation system stores instructions concerning one or more processes that may be performed on the first and/or second droplets. The process concerned is highly variable because the sensing system of the invention is widely applicable: it may for instance be a process for preparing a sample; a process for analysing the content of a sample; a process for performing an assay on a sample; and so on. Each such process will have a variety of droplet operations associated with it. As will be discussed in more detail below, a droplet operation typically involves moving one or more droplets. To take a simple example, where the process is a process for analysing an analyte present in a droplet, the droplet operations that can be performed may involve:

bringing a droplet containing analyte into contact with another droplet to form a droplet interface comprising a transmembrane pore;

moving a droplet containing analyte away from another droplet to separate a droplet interface;

bringing in a new droplet of sample to the system if the previous droplet has degraded or is of low quality;

adding an additional droplet of analyte to a droplet containing analyte if the analyte has become depleted;

adding an additional droplet of electron mediator to a droplet if the electron mediator has become depleted;

removing a droplet of analyte from the system to be retained;

and so on. The operation system is configured to apply the stored instructions concerning one or more processes of interest and, based on information obtained from one or more electrical measurements, to select a droplet operation.

In some embodiments, the operation system is further configured to apply an actuation signal to one or more actuation electrodes to effect the droplet operation. In other embodiments, the operation system may be configured to provide an output to a GUI, for example to present the user with the option to decide whether the droplet operation should be performed. In an aspect of this embodiment, the operation system may be configured to select two or more droplet operations and to then provide an output to a GUI in order to allow the user to select one of those droplet operations to be performed.

In some aspects, in order to select a droplet operation to be performed, the operation system is configured to store information on the nature and location of a plurality of droplets within the sensing system. By "nature" of droplets means the composition of droplets within the sensing system, for instance the liquid medium comprised in the droplet may contain any species such as analyte, electron mediator, substrates for reactions and so on. The "nature" of a droplet may also mean the concentration of such species, and so on. By "location" is meant the location of the droplet within the sensing system.

This information may be held within the operation system on the basis of a pre-programmed configuration; that is, the operation system may be provided with information on the nature and location of droplets within the sensing system in an initial state of the sensing system. In that case, the operation system may establish the nature and location of a droplet within the system after one or more droplet operations have occurred by reference to those droplet operations and the initial state of the system. By way of example, if the operation system can access the information that (i) a droplet comprising analyte was initially present at position A and that (ii) a droplet operation has been performed moving a droplet from position A to position B, the operation system may store the information that a droplet comprising analyte is present at position B without performing any electrical measurement on the droplet at position B. The information on the nature and location of droplets within the sensing system in an initial state may be stored permanently or temporarily; for example, it may be overwritten as each droplet operation occurs.

On the other hand, the operation system may determine information on the nature and location of a droplet based on electrical or other measurements. For instance, the operation system may establish that a droplet is present at a location relative to sensor electrode based on an electrical measurement taken at that sensing electrode, and may further establish the nature of the analyte present in that droplet by performing an electrical measurement using a sensing electrode in contact with said droplet. Once established, this information may be stored temporarily (for example, until new such information is determined).

Further, the operation system may establish and/or store information on the nature and location of droplets within the system by a mixture of the two above-described methods.

In some aspects, therefore, the operation system is configured to select a droplet operation based on (i) the electrical measurement and (ii) one or more instructions and information concerning the nature and location of one or more droplets of liquid medium present in the sensing system stored in the control system (that is, the operation system within the control system).

The obtaining and storing of information within the control system as to the location of droplets and the nature of those droplets is particularly useful in embodiments of the invention where the method is performed on a plurality of droplet systems in parallel. The operation system provides great advantages in speed especially in those embodiments where the operation system is configured to perform step (c), i.e. to effect the droplet operation, automatically and without input from the user.

The control system may further comprise an analysis system configured to process the electrical measurements to analyse an analyte that interacts with the first transmembrane pore. For example, where the analyte is a polymer comprising polymer units, the analysis system may be configured to process the electrical measurements to derive estimated identities of the polymer units of the polymer. The analysis system may or may not be connected to the operation system. That is, output from the analysis system may or may not be input into the operation system to enable the operation system to select a droplet operation.

The control system is connected to the actuation electrodes and is configured to apply actuation signals to the actuation electrodes for manipulating received droplets.

The control system may be configured, while applying actuation signals to the actuation electrodes, to apply a reference signal to the first and second sensing electrodes (e.g. to an array of sensing electrodes) and/or to the further electrodes, where provided.

Advantageously, the control system may be arranged to apply actuation signals to the actuation electrodes selected to form plural systems of droplets in parallel. By a "system of droplets" is meant an arrangement comprising at least the first and second droplet as defined herein. This allows the apparatus to perform experiments on the plural systems in parallel with each other, thereby increasing the experimental throughput of the apparatus.

In terms of hardware, the control system typically comprises control electronics and a storage device that may store any application software any data associated with the control system. The control electronics may include suitable circuitry and/or processing devices that are configured to carry out various control operations relating to control of the EWOD device, such as a CPU, microcontroller or microprocessor.

Among their functions, to implement the features of the present invention, the control electronics may comprise a part of the overall control system that may execute program code embodied as a control application within the storage device. The storage device may be configured as a non-transitory computer readable medium, such as random access memory (RAM), a read-only memory (ROM), an erasable programmable read-only memory (EPROM or Flash memory), or any other suitable medium. Also, while the code may be executed by control electronics in accordance with an exemplary embodiment, such control system functionality could also be carried out via dedicated hardware, firmware, software, or combinations thereof.

The control system typically comprises a user interface such as a graphical user interface (GUI) to a user which provides for the user to input of program commands. For example, the GUI may permit the user to select the instructions employed by the operation system. However, this is unnecessary as the operation system may comprise a set of instructions according to which it operates the sensing and actuation electrodes without input from the user. Where the control system comprises a user interface, it may permit the user to, for instance, select an assay to be performed or to choose whether or not the sample is to be retained. The GUI may be used for displaying the results of the operation of the sensing system to the user.

A serial interface may also be provided to process a serial input data stream and facilitate the programming of the required voltages to the actuation electrodes in the array of actuation electrodes, and/or to the first and second sensing electrodes.

A voltage supply interface provides the requisite voltage inputs to the array of actuation electrodes and/or the sensing electrodes.

The control system may further comprise a droplet interface sensor system including a measurement unit which is connected to the sensing electrodes and takes electrical measurements between the first and second sensing electrodes. The measurement unit is typically controlled to take electrical measurements out while actuation signals are not applied to the actuation electrodes. This has the advantage of reducing the risk of the actuation signals affecting the electrical measurements, for example by physically affecting or damaging the system of droplets being measured or by causing electrical interference with the measurement unit. The measurement unit may be formed by suitable electronic components suitable for droplet interface experiments, for example including detection channels including amplifier arrangements. In one example, the measurement unit may comprise a patch clamp arrangement. In another example, the measurement unit may have the same construction as the signal processing function described in WO-2011/067559.

Droplets

During operation of the sensing system according to the method of the invention, the sensing system comprises a fluid medium and a first and second droplet of liquid medium. The first and second droplets are disposed on the hydrophobic surface of the EWOD device. The first and second droplets may also contact the second substrate of the EWOD device where present, or layers upon that second substrate. Generally, any part of the first and second droplets not in contact with the hydrophobic surface or the second substrate contacts the fluid medium.

In some embodiments, the sensing system comprises third or further droplets of liquid medium. Those droplets are disposed as the first and second droplets: on the hydrophobic surface, in the fluid medium.

In general, any liquid that forms a droplet in a fluid medium may be used as the first and second droplets in the fluid medium, but some possible materials are as follows.

The fluid medium may in principle be a gaseous medium, but is preferably a liquid medium.

One of the liquid and the fluid medium is polar, and the other of the liquid and the fluid medium is apolar. Preferably, the liquid of the droplets is polar, and the fluid medium is apolar. Typically, the liquid of the first, second and where present third droplets is polar and the fluid medium is apolar, with the result that the actuation electrodes to which actuation signals are applied are electro-wet. In other embodiments, the liquid of the first, second and where present third droplets is apolar and the fluid medium is polar; in that case, the actuation electrodes to which actuation signals are not applied attract the apolar droplets.

When one of the liquid and the fluid medium is polar, the polar medium is typically an aqueous liquid that comprises water. The aqueous liquid may further comprise one or more solutes. The aqueous liquid may for instance comprise a buffer in order to regulate the pH of the aqueous medium as appropriate, and it may comprise a supporting electrolyte. The aqueous medium may for instance comprise a redox couple, or a member of a redox couple which may be partially oxidised or reduced to provide the redox couple. The redox couple may chosen from those known in the art such as $Fe^{2+}/Fe^{3+}$, ferrocene/ferrocenium or $Ru^{2+}/Ru^{3+}$. Examples of such are ferro/ferricyanide, ruthenium hexamine and ferrocene carboxylic acid.

Alternatively, when one of the liquid and the fluid medium is polar, the polar medium may comprise a polar organic solvent. The polar organic solvent may for instance be a protic organic solvent, such as an alcohol, or it may be an aprotic polar organic solvent.

The liquid of the droplets may be any liquid suitable for performing experiments of the type described below. Different droplets may comprise different liquids.

Where the other of the liquid and the fluid medium is apolar, then the apolar medium may comprise an oil. The oil may be a single compound, or the oil may comprise a mixture of two or more compounds. In one example, the oil is pure alkane hydrocarbon.

The oil may for instance comprise silicone oil. Suitable silicone oils include, for instance, poly(phenyl methyl siloxane) and poly(dimethylsiloxane) (PDMS). The silicone oil may comprise a hydroxy-terminated silicone oil, for instance hydroxy terminated PDMS. Additionally or alternatively, the oil may comprise a hydrocarbon, for instance hexadecane, although any suitable hydrocarbon may be used. When the oil comprises a hydrocarbon it may comprise a single hydrocarbon compound, or a mixture of two or more hydrocarbons. When the oil comprises a hydrocarbon, the hydrocarbon may be branched or unbranched. The hydrocarbon may for instance be squalene, hexadecane or decane. In one embodiment it is hexadecane. However, in some embodiments the hydrocarbon may be substituted with a halogen atom, for instance bromine.

The oil may comprise a mixture of one or more silicone oils and one or more hydrocarbons. The silicone oil and hydrocarbon in the mixture may both be as further defined above. The silicone oil may for instance be poly(phenyl methyl siloxane) or PDMS.

Other types of oil are also possible. For example, the oil may be a fluorocarbon or a bromo-substituted $C_{10}$-$C_{30}$ alkane.

The sensing system may comprise one or more droplets comprising analyte. Typically, the first droplet comprises analyte. An analyte is usually any species that is capable of interaction with the first transmembrane pore, and can also referred to as a target analyte, the template analyte or the analyte of interest. For example, the analyte may be a polymer or a drug. Alternatively, the analyte may be a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant. Typically, the analyte is charged.

The analyte may be an amino acid, a peptide, a polypeptide and/or a protein. The amino acid, peptide, polypeptide or protein can be naturally-occurring or non-naturally-occurring. The polypeptide or protein can include within them synthetic or modified amino acids. A number of different types of modification to amino acids are known in the art. For the purposes of the invention, it is to be understood that the analyte can be modified by any method available in the art.

The analyte protein can be an enzyme, an antibody, a hormone, a growth factor or a growth regulatory protein, such as a cytokine. The cytokine may be selected from interleukins, preferably IFN-1, IL-1, IL-2, IL-4, IL-5, IL-6, IL-10, IL-12 and IL-13, interferons, preferably IL-$\gamma$, and other cytokines such as TNF-$\alpha$. The protein may be a bacterial protein, a fungal protein, a virus protein or a parasite-derived protein.

The analyte may be a nucleotide, an oligonucleotide or a polynucleotide. Nucleotides and polynucleotides are discussed below. Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed below, including the abasic, and modified, nucleotides.

At least a portion of the polynucleotide may be double stranded.

The polynucleotide can be a nucleic acid, such as deoxyribonucleic acid (DNA) or ribonucleic acid (RNA). The polynucleotide can comprise one strand of RNA hybridised to one strand of DNA.

The polynucleotide can be any length. For example, the polynucleotide can be at least 10, at least 50, at least 100, at least 500 nucleotides or nucleotide pairs in length. The polynucleotide can be 1000 or more, 10000 or more, 100000 or more, or 1000000 or more nucleotides or nucleotide pairs in length.

Any number of polynucleotides can be investigated. For instance, the method of the invention may concern characterising 2, 3, 4, 5, 6, 7, 8, 9, 10, 20, 30, 50, 100 or more polynucleotides. If two or more polynucleotides are characterised, they may be different polynucleotides or two instances of the same polynucleotide.

The polynucleotide can be naturally occurring or artificial.

Where the analyte is a polynucleotide comprising nucleotides and estimated identities of the polymer units are derived from the electrical measurements, then strand characterisation/sequencing or exonuclease characterisation/sequencing may be applied. In strand sequencing, the polynucleotide may be translocated through the nanopore either with or against an applied potential. In this case, the electrical measurements are indicative of one or more characteristics of multiple nucleotides.

One or more droplets, particularly a droplet containing analyte, may contain a polymer binding moiety such as an enzyme to control translocation of the polymer through the pore. The moiety can be a molecular motor using for example, in the case where the moiety is an enzyme, enzymatic activity, or as a molecular brake.

Where the polymer is a polynucleotide there are a number of methods proposed for controlling the rate of translocation including use of polynucleotide binding enzymes. Suitable enzymes for controlling the rate of translocation of polynucleotides include, but are not limited to, polymerases, helicases, exonucleases, single stranded and double stranded binding proteins, and topoisomerases, such as gyrases. For other polymer types, moieties that interact with that polymer type can be used. The polymer interacting moiety may be any disclosed in WO-2010/086603, WO-2012/107778, and Lieberman K R et al, J Am Chem Soc. 2010; 132(50):17961-72), and for voltage gated schemes (Luan B et al., Phys Rev Lett. 2010; 104(23):238103).

The polymer binding moiety can be used in a number of ways to control the polymer motion. The moiety can move the polymer through the transmembrane pore with or against the applied field. The moiety can be used as a molecular motor using for example, in the case where the moiety is an enzyme, enzymatic activity, or as a molecular brake. The translocation of the polymer may be controlled by a molecular ratchet that controls the movement of the polymer through the pore. The molecular ratchet may be a polymer binding protein. For polynucleotides, the polynucleotide binding protein is preferably a polynucleotide handling enzyme.

Preferred polynucleotide handling enzymes are polymerases, exonucleases, helicases and topoisomerases, such as gyrases. A polynucleotide handling enzyme may be for example one of the types of polynucleotide handling enzyme described in WO-2015/140535 or WO-2010/086603.

The volume of each droplet is not particularly limited. The first, second and (where present) third or further droplets may each have volumes which are the same or different.

The shape of a droplet is not particularly limited. While a droplet is in electrical contact with one or more actuation electrodes, and the actuation electrode(s) maintain the droplet in an energised state, the shape of a droplet is determined by the activation electrodes. The actuation electrodes can therefore not only manipulate the location of a droplet upon the hydrophobic surface but also its shape. A wide variety of shapes can be formed. For example, a droplet may be square, round, elongated, or ring-shaped in the plane parallel to the hydrophobic surface.

Where the droplet has been shaped by signals from the actuation array, when the droplet is permitted to relax to a lower energy state (for example when the actuation electrode is switched off), the droplet will relax. By this is meant that the shape of the droplet will become distorted from the shape adopted by the droplet while the actuation signal(s) forced the droplet to electrowet particular actuation electrodes.

In some embodiments, a droplet present in the sensing system is in electrical contact with at least two actuation electrodes, preferably at least 5 actuation electrodes, at least 10 actuation electrodes or at least 20 actuation electrodes. This is because the more actuation electrodes a droplet is in electrical contact with, the better the resolution of the control of the shape in the energised state of the droplet. That in turn allows the degree of movement of the surface of the at least one droplet to be increased, which assists in the control of droplet operations such as bringing one droplet into contact with another droplet.

Amphipathic Molecules

A droplet interface is the region of space in which one droplet contacts another. A droplet interface may comprise a layer of amphipathic molecules, such that one or both droplets which contact one another at the droplet interface are in contact with the layer of amphipathic molecules. In some embodiments, the droplet interface may comprise a bilayer of amphipathic molecules: that is, two adjacent monolayers of amphipathic molecules. In that case, the droplet interface comprising a bilayer may be referred to as a droplet interface bilayer (DIB). DIBs may be used for the study of transmembrane pores inserted therein. For example, Martel et al., Biomicrofluidics 6, 012813 (2012) discloses a microfluidic device for forming droplet interface bilayers into which a protein channel was inserted. Gold microwires were deposited onto the substrate including the actuation electrodes upon which Ag/AgCl pads were provided in order to make electrical contact with each droplet in order to carry out measurements of ion current flow through the membrane channel.

The first and second droplets contact one another via a droplet interface, which droplet interface comprises a layer of amphipathic molecules. The sensing system may comprise a plurality of other droplet interfaces, each comprising a layer of amphipathic molecules, as described herein. However, amphipathic molecules are not only present at droplet interfaces. The first droplet and/or the second droplet comprises a layer of amphipathic molecules at an interface between the said droplet and the fluid medium. For example, the layer of amphipathic molecules may be present at the entirety of the interface between said droplet and the fluid medium. In some embodiments, the first and the second droplet each comprises a layer of amphipathic molecules at the entirety of their respective interfaces with the fluid medium.

Where the sensing system comprises a third or further droplet of liquid medium, each such droplet may optionally comprise a layer of amphipathic molecules at an interface between said droplet and the fluid medium. The layer of amphipathic molecules may be present at the entirety of the interface between said droplet and the fluid medium.

Amphipathic molecules serve to stabilise a droplet in the fluid medium prior to formation of a droplet interface. Also, the amphipathic molecules may allow the droplet interface, when formed, to comprise a membrane of amphipathic molecules.

Numerous different types of amphipathic molecules may be used. Each droplet comprising a layer of amphipathic molecules may comprise one or more types of amphipathic molecules. Where the sensing system comprises two or more droplets each comprising amphipathic molecules (for instance in the form of a layer at an interface with the fluid medium), those droplet may comprise the same or different amphipathic molecules. Some non-limitative examples of types of amphipathic molecules that may be used are as follows.

In one example, the amphipathic molecules may comprise a lipid, which may have a single component or a mixture of components, as is conventional when forming lipid bilayers. Any lipids that form a membrane such as a lipid bilayer may be used. Phospholipids may be employed. The lipids are chosen such that a lipid bilayer having the required properties, such as surface charge, ability to support membrane proteins, packing density or mechanical properties, is formed. The lipids can comprise one or more different lipids. For instance, the lipids can contain up to 100 lipids. The lipids preferably contain 1 to 10 lipids. The lipids may comprise naturally-occurring lipids and/or artificial lipids. The lipids can also be chemically-modified.

A layer of amphipathic molecules at an interface between two droplets may be referred to as a membrane. Amphipathic polymer membranes are preferred over lipid membranes due to their ability to withstand higher voltages.

In another example, the amphipathic molecules may comprise an amphipathic compound comprising a first outer hydrophilic group, a hydrophobic core group, and a second outer hydrophilic group, wherein each of the first and second outer hydrophilic groups is linked to the hydrophobic core group. Some such amphipathic compounds are disclosed in WO 2014/064444, the entire contents of which are incorporated herein by reference. Other such amphipathic compounds are disclosed in U.S. Pat. No. 6,916,488 which is incorporated herein by reference and discloses a number of polymeric materials that can be employed in the apparatus 1 as planar amphipathic membranes. In particular triblock copolymers are disclosed, for example silicon triblock copolymer membranes such as poly(2-methyloxazoline)-block-poly(dimethylsiloxane)-block-poly(2-methyloxazoline) (PMOXA-PDMS-PMOXA). Examples of silicone triblock polymers that may be employed are 7-22-7 PMOXA-PDMS-PMOXA, 6-45-6 PMOXA-PE-PMOXA and 6-30-6 PMOXA-PDMS-PMOXA, where the nomenclature refers to the number of subunits. Such triblock copolymers may be provided in vesicle form in the droplets.

Depending on the nature of the amphipathic molecules, the membranes may be bilayers of the amphipathic molecules or may be monolayers of the amphipathic molecules. The amphipathic molecules may alternatively be replaced by another surfactant.

Different droplet interfaces may comprise membranes of different amphipathic molecules, for example membranes comprising a lipid bilayer and a polymer membrane such as a silicone triblock polymer membrane as described above, such as disclosed in WO2017/004504. The electrical measurements that are taken may be used to study the membrane of amphipathic molecules itself, or interactions thereof, for example to study drug-membrane permittivity.

Transmembrane Pore

The sensing system of the invention may comprise one or more transmembrane pores. In general any transmembrane pore may be used that is capable of inserting into a droplet interface. Different droplets may comprise the same or different transmembrane pore, so that when plural droplet interfaces are formed between different plural droplet pairs, the same or different transmembrane pore may insert into those droplet interfaces.

Some non-limitative examples of types of transmembrane pore that may be used are as follows.

A transmembrane pore is a channel structure that, when inserted in a membrane, allows communication between opposite sides of the membrane. Typically, a transmembrane pore is a channel structure that provides a pathway from one side of a membrane to the other through which ions may flow. In some embodiments, a transmembrane pore is a channel structure which allows an analyte to enter the channel at least partially. By "at least partially" is meant that the transmembrane pore may allow an analyte to enter the ion channel but not to pass through it from one side of a membrane to the other; in some embodiments, a transmembrane pore is permeable to analyte. The channel may vary in width along its length and typically has an inner diameter of between 0.5 nm and 10 nm.

Any suitable transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936). Suitable DNA origami pores are disclosed in WO2013/083983.

The transmembrane pore is preferably a transmembrane protein pore.

The transmembrane protein pore may be a monomer or an oligomer. The pore may be a hexameric, heptameric, octameric or nonameric pore. The pore may be a homo-oligomer or a hetero-oligomer.

The transmembrane protein pore may be derived from CsgG, such as from CsgG from *E. coli* Str. K-12 substr. MC4100. Examples of suitable CsgG pores are described in WO-2016/034591, WO-2017/149316, WO-2017/149317 and WO-2017/149318.

The transmembrane protein pore typically comprises a barrel or channel through which the ions may flow. The subunits of the pore typically surround a central axis and contribute strands to a transmembrane 3 barrel or channel or a transmembrane α-helix bundle or channel. The barrel or channel of the transmembrane protein pore comprises amino acids that facilitate interaction with an analyte, such as a nucleotide, polynucleotide or nucleic acid.

The pore may be modified by for example substitution or deletion of one of more amino acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores, such as lysenin. α-helix bundle pores comprise a barrel or channel that is formed from α-helices. Suitable α-helix bundle pores include, but are not limited to, inner membrane proteins and a outer membrane proteins, such as WZA and ClyA toxin.

The transmembrane pore may be derived from or based on Msp, α-hemolysin (α-HL), lysenin, CsgG, ClyA, Sp1 and haemolytic protein fragaceatoxin C (FraC). The transmembrane protein pore is preferably derived from CsgG, more preferably from CsgG from *E. coli* Str. K-12 substr. MC4100.

The transmembrane pore may be derived from lysenin. Suitable pores derived from lysenin are disclosed in WO 2013/153359.

The pore may be a variant of the above listed nanopores. The variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence.

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/). Similarity can be measured using pairwise identity or by applying a scoring matrix such as BLOSUM62 and converting to an equivalent identity. Since they represent functional rather than evolved changes, deliberately mutated positions would be masked when determining homology. Similarity may be determined more sensitively by the application of position-specific scoring matrices using, for example, PSIBLAST on a comprehensive database of protein sequences. A different scoring matrix could be used that reflect amino acid chemico-physical properties rather than frequency of substitution over evolutionary time scales (e.g. charge).

Amino acid substitutions may be made to the transmembrane protein, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Any of the proteins described herein, such as the transmembrane protein pores, may be made synthetically or by recombinant means. For example, the pore may be synthesised by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Electrical Measurement

Methods for performing electrical measurements upon droplets disposed on an EWOD device are known. US-2010/0,194,408 discloses a method, circuit and apparatus for detecting capacitance on a droplet actuator inter alia for determining the presence, partial presence or absence of a droplet at an actuation electrode. U.S. Pat. No. 8,653,832 describes how an impedance (or capacitance) sensing function can be incorporated into the array element circuit of each array element of an EWOD device, wherein the impedance sensor circuit may be used for determining the presence and size of droplets present at each electrode in the array. However, these approaches are limited by the need to obtain signals from the same electrodes to which the actuation signals are applied.

Martel et al., Biomicrofluidics 6, 012813 (2012) discloses a microfluidic device for forming droplet interface bilayers into which a protein channel was inserted, wherein gold microwires were deposited onto the substrate including the actuation electrodes upon which Ag/AgCl pads were provided in order to make electrical contact with each droplet in order to carry out measurements of ion current flowing through the membrane channel. However, this construction is inconvenient and difficult to manufacture, as well as limiting the reliability of taking measurements and limiting the scalability of the technique.

Any suitable electrical measurements may be taken, for example impedance, current or capacitance measurements. In one aspect, the electrical measurement may be taken by applying a voltage and measuring the current sourced through first and second sensing electrodes, whilst the other is grounded. The real and imaginary parts of the electrical impedance of a droplet interface across which the electrical measurement is taken may thus be determined.

The electrical measurement is typically an electrical measurement taken between a pair of droplets. Most usually, the electrical measurement is an electrical measurement taken across a droplet interface, wherein the droplet interface comprises a layer of amphipathic molecules and a transmembrane pore inserted therein. For example the electrical measurement may be an electrical measurement taken across the interface between the first droplet and the second droplet.

Figure 9:
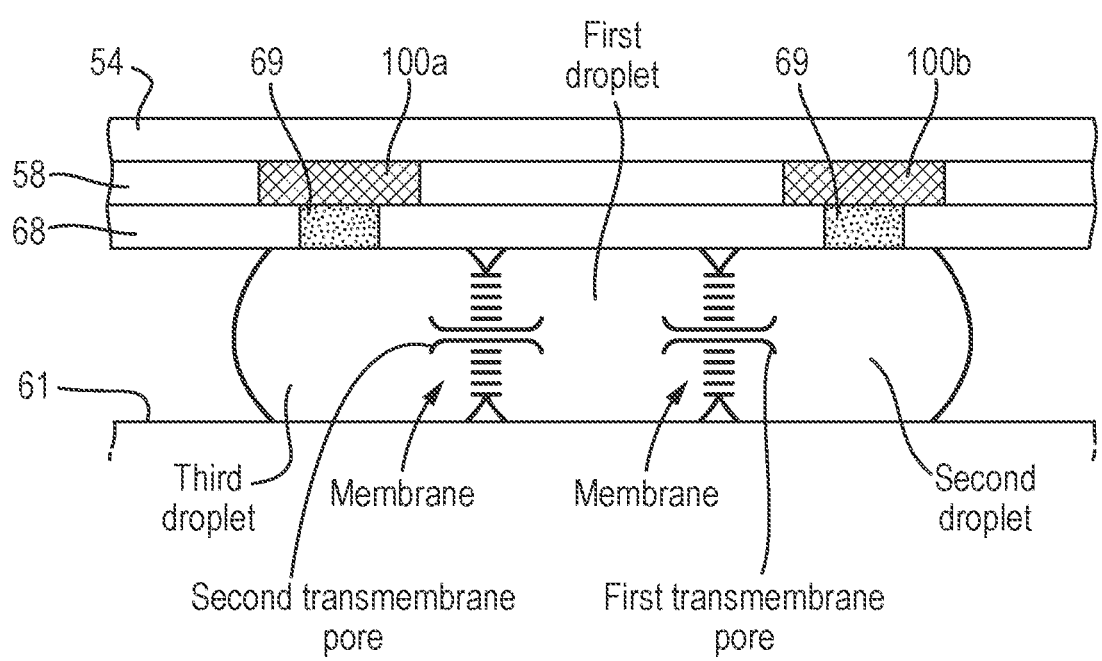
FIG. 9 is an illustration of a three-droplet construct in the sensing system of the invention.

In some embodiments, the electrical measurement may be an electrical measurement taken between a pair of droplets separated by more than one droplet interface. In these embodiments, typically each said interface comprises a layer of amphipathic molecules and a transmembrane pore. For example, where the sensing system comprises a third droplet in addition to the first and second droplets, and the third droplet is in contact with the first droplet via a droplet interface, which droplet interface comprises a layer of amphipathic molecules and a transmembrane pore, the electrical measurement may be an electrical measurement taken between the first sensing electrode in contact with the third droplet and the second sensing electrode in contact with the second droplet, as is shown in FIG. 9.

In one embodiment, the electrical measurement comprises determining whether a droplet (for example, the first, second or third droplet) is in electrical contact with a particular electrode. For instance, the electrical measurement may comprise determining the location of a droplet (for example the first, second or third droplet) within the sensing system.

An exemplary electrical measurement is the measurement of ion flow between droplets through a transmembrane pore. For instance, where the electrical measurement is an electrical measurement taken across the first and second droplets (as shown in FIG. 8, where the first and second sensing electrodes are in contact with the first and second droplets), the electrical measurement may be a measurement of the ion flow through the first transmembrane pore. In another example, where the electrical measurement is an electrical measurement across the setup shown in FIG. 9 where the first sensing electrode is in contact with a third droplet and the second sensing electrode is in contact with a second electrode; and where the first droplet forms a droplet interface with the second droplet comprising a first transmembrane pore, and the first droplet forms a droplet interface with the third droplet comprising a second transmembrane pore, then the electrical measurement may be a measurement of ion flow across the first and second transmembrane pores taken together.

Another exemplary electrical measurement is an electrical measurement which is dependent on the interaction of an analyte with a transmembrane pore. For instance, the electrical measurement may be taken between the first and second sensing electrodes in a system as shown in FIG. 8, and the electrical measurement may be an electrical signal indicating an interaction (or the absence of an interaction) with the first transmembrane pore. In another example, the electrical measurement may be taken between the first and second sensing electrodes in a system as shown in FIG. 9, and the electrical measurement may be an electrical signal indicating an interaction (or the absence of an interaction) with the first transmembrane pore, or the second transmembrane pore, or the first and second transmembrane pores together.

The electrical measurement which is dependent on the interaction of an analyte with a transmembrane pore may be a measurement of ion flow across the transmembrane pore. The interaction of an analyte with the transmembrane pore may appear as an alteration of the electrical signal which occurs when the analyte interacts with the pore, interrupting the ion flow.

Where the electrical measurements are dependent on the interaction of the analyte with the transmembrane pore, the analysis may determine the presence, absence or one or more characteristics of a target analyte. Where the analyte is a polymer comprising polymer units, in the analysis the electrical measurements may be processed to derive estimated identities of the polymer units, or to count polymer units or determine length of the polymer. Control experiments can be carried out in the presence of different analytes or polymer units, to determine how analytes affect the electrical measurements as the basis for the analysis.

The analysis may be performed using any suitable known technique, including techniques employing a Hidden Markov Model, for example as described in WO-2013/041878 or WO-2015/140535; techniques employing machine learning for example as described in Boza et al., "DeepNano: Deep recurrent neural networks for base calling in MinION nanopore reads", PLoS ONE 12(6): e0178751, 5 Jun. 2017; techniques employing comparison of feature vectors for example as described in WO-2013/121224; or any other suitable technique.

Interaction between a target analyte and a transmembrane pore may occur as an analyte moves with respect to, such as translocating through, the pore. In that case, the electrical measurements may be taken as the analyte moves with respect to the pore. Such movement may occur while a potential difference is applied between the droplets, i.e. across the transmembrane pore. The applied potential typically results in the formation of a complex between the pore and a polynucleotide binding protein. The applied potential difference may be a voltage potential. Alternatively, the applied potential difference may be a chemical potential. An example of this is using a salt gradient across an amphiphilic layer. A salt gradient is disclosed in Holden et al., J Am Chem Soc. 2007 Jul. 11; 129(27):8650-5.

The electrical measurement (for example a measurement of ion flow) optionally may be taken while applying a potential difference between the droplets. The potential difference may be applied using the first and second sensing electrodes. In one embodiment, therefore, the electrical measurement is taken while applying a potential difference across the first and second sensing electrodes.

The electrical measurements may be taken in a frequency range from a lower limit to an upper limit, wherein the lower limit is 1 Hz, 10 Hz or 100 Hz and the upper limit is 10 MHz, 100 KHz or 10 KHz, in any combination.

Initial Droplet Arrangements

Hereafter are described various typical aspects of the initial configuration of the first and second droplets (and, where present, the third and further droplets) within the sensing system, before the performance of steps (a), (b) and (c) in the method of the invention.

The method of the invention is performed upon a first and second droplet which are in contact via a droplet interface comprising layer of amphipathic molecules. A suitable method of providing such a droplet interface comprising a layer of amphipathic molecules is to provide either or both of the first and second droplets with an outer layer of amphipathic molecules. Amphipathic molecules may be provided in either the liquid medium comprised in the relevant droplet(s), or in the fluid medium. The outer layer of amphipathic molecules will typically form spontaneously, in order to place the hydrophobic moiety of the amphipathic molecule in contact with the apolar medium and the hydrophilic moiety in contact with the polar medium, as this is an energetically favourable arrangement. The first and second droplets may then be brought into contact by applying a suitable actuation signal to the array of actuation electrodes. Thus, either the first or the second droplet comprises a layer of amphipathic molecules at an interface between the said first and/or second droplet and the fluid medium. This layer of amphipathic molecules may cover all or part of the interface between the said first and/or second droplet and the fluid medium; typically the layer of amphipathic molecules covers the whole of said interface.

The presence of a layer of amphipathic molecules at the interface between the first or second droplet and the fluid medium stabilises the said first or second droplet. Accordingly, in a preferred embodiment, the first and the second droplet each comprise a layer of amphipathic molecules at an interface between the liquid medium and the fluid medium. The layer of amphipathic molecules may cover the entire interface between the liquid medium and the fluid medium.

The interface between the first and second droplets comprises a first transmembrane pore. The transmembrane pore typically inserts spontaneously into the layer or amphipathic molecules at the droplet interface, also called the membrane. Thus, the first transmembrane pore may initially be provided in either the first or the second droplet before they are brought into contact to form the initial state of the sensing system. Of course, the system is not limited to the presence of a single pore: the interface between the first and second droplets may comprise a plurality of transmembrane pores, each of which may be the same or different to one another. In certain embodiments, a droplet interface may comprise a single transmembrane pore.

The sensing system of the invention is advantageously versatile and permits a plurality of droplets to be brought into contact with one another, for example to expose an analyte contained within a droplet to a plurality of transmembrane pores. Thus, in a further preferred embodiment, the first droplet is in contact with a third droplet of liquid medium via a droplet interface, and the droplet interface between the first droplet and the third droplet comprises a layer of amphipathic molecules. In one aspect of this embodiment, the interface between the first droplet and the third droplet further comprises a transmembrane pore, which transmembrane pore may be the same or different to the first transmembrane pore.

Where the sensing system comprises a second and third droplets in contact with the first droplet, the three droplets may be arranged such that each droplet contacts the other. In this embodiment, the second droplet is also in contact with the third droplet via a droplet interface, and the droplet interface between the second droplet and the third droplet comprises a layer of amphipathic molecules. This interface between the second and third droplets may optionally comprise a transmembrane pore, which may be the same or different to the first transmembrane pore. In this embodiment, an analyte present in any of the first, second or droplets may move to either of the other two droplets present via a transmembrane pore.

On the other hand, where the sensing system comprises a second and third droplets in contact with the first droplet, the third droplet and the second droplet may not be in contact with each other. In this embodiment, an analyte present in the first droplet may move into the second or third droplets, but no analyte can move from the second to the third droplets.

A particular advantage of the present system is that it can provide very complex sensing systems (in very small volumes): a single droplet can for example contact more than two other droplets, in each case via a droplet interface comprising a membrane and a transmembrane pore. Such a system approaches the complexity of the MinION™ device (a current market leading device) on a very small scale. Accordingly, there is provided a method wherein the first droplet is also in contact with one or more further droplets of liquid medium each via a further droplet interface, and the each further droplet interface comprises a layer of amphipathic molecules. Each further droplet interface optionally comprises a transmembrane pore, which may be the same as or different to the first transmembrane pore. This set-up advantageously permits an analyte to be detected as it moves through each pore in turn, if induced to do so by applied potentials. Alternatively, of course, a similar result may be achieved by moving the first droplet into contact with a succession of further droplets in turn, at each instance forming a droplet interface comprising a membrane and a transmembrane pore.

The layer of amphipathic molecules provided at each of the aforementioned droplet interfaces may consist of a monolayer of amphipathic molecules. This may be the case where, for instance, the amphipathic molecules are triblock copolymers comprising two polar blocks and one apolar block, or two apolar blocks and one polar block. However, the layer of amphipathic molecules may comprise two layers, for example a bilayer, of amphipathic molecules. Bilayers are known to form where lipid molecules, e.g. phospholipid molecules, are used as the amphipathic molecules; bilayers can also form where triblock copolymers are used, as described in WO 2014/064444. Thus, in any of the preceding embodiments, the or each droplet interface comprises a bilayer of amphipathic molecules. In other embodiments the or each droplet interface may comprise a monolayer of amphipathic molecules, together with a transmembrane pore or pores. Where a plurality of membranes are present, some membranes may comprise bilayers while others may comprise monolayers of amphipathic molecules.

The membrane between the first and second droplets comprises a transmembrane pore. In a preferred embodiment, where the sensing system comprises further droplet interfaces comprising a membrane, one or more of the said further droplet interfaces comprises a transmembrane pore. Particularly preferably, each membrane present in the sensing system comprises a transmembrane pore. Each transmembrane pore may be the same or different.

It may be desirable to promote easy and rapid transfer of material across a membrane. In a particular example, it may be desirable to detect the interaction of an analyte in the first droplet with the first transmembrane pore, while preventing direct electrical contact between the analyte and a sensing electrode. In this case, the analyte may be contained in the first droplet, and the first droplet may be in contact with a second and third droplet via a membrane. Thus, the first and second sensing electrodes may contact the second and third droplets rather than the first and second droplets. However, in order to ascertain the interaction between the analyte and the first transmembrane pore, there must be transfer of electrical charge between the first and third droplets. In relation to the first and second droplets, ions can typically permeate the first transmembrane pore; that is, the first transmembrane pore typically acts as an ion channel. However, in relation to the first and third droplets, this may be achieved by providing a plurality (typically a high number, for instance at least ten or at least 100) of ion channels within the membrane between the first and third droplets. In this case, the plurality of ion channels act as a kind of frit, preventing transfer of analyte into the third droplet while permitting charge transfer and hence electrical interaction between the first and second electrodes. The high number of ion channels between a pair of droplets (e.g. the first and third droplets) reduces the electrical resistance at that point in the droplet network, enabling current to flow between the sensing electrodes to enable sensing (e.g. at the interface between the first and second droplets).

Where the interface between a pair of droplets in a three-droplet construct having two droplet interfaces comprises a plurality of ion channels present in the membrane at one droplet interface, the number of ion channels is typically high compared to the number of transmembrane pores present in the other interface. For instance, the number of ion channels may be at least 10 times, at least 100 times or at least 1000 times, for instance at least 10,000 times, or at least 100,000 times greater than the number of transmembrane pores in the other droplet interface. For instance, where a construct comprising a first, second and third droplets comprises a plurality of ion channels at a droplet interface between the third and first droplets, and one or more transmembrane pores at an interface between the first and second droplets, the number of ion channels in the interface between the first and third droplets may be at least 10 times, at least 100 times or at least 1000 times, for instance at least 10,000 times, or at least 100,000 times, greater than the number of transmembrane pores in the interface between the first and second droplets.

In a further aspect of this embodiment, it may be desired to separate the analyte entirely from the electron mediator used to permit charge transfer with the electrode. In that case, the droplet construct may be as described above except that the ion channels are impermeable to the electron mediator. For instance ion channels or nanopores that are too narrow to allow passage of the analyte and/or electron mediator may be employed between the first and third droplets, or ion channels or nanopores with negative charges in the central channel of the nanopore/channel. Moreover, the first transmembrane pore may not permit the analyte to penetrate out of the first droplet entirely into the second droplet; in that case, the analyte is retained entirely within the first droplet.

Thus, in one aspect of the invention, the sensing system comprises one or more droplet interfaces each comprising a plurality of ion channels, for example at least ten ion channels. In one aspect, this said droplet interface comprising a plurality of ion channels contacts the first droplet. In a further aspect of this embodiment, the said ion channels are impermeable to an electron mediator. For example, the droplet interface between the first droplet and the third droplet may comprise a plurality of ion channels.

In the foregoing embodiments, typically the first droplet comprises an analyte. The analyte may contain a single chemical species or a mixture of species.

Typically, the second droplet comprises an electron mediator. By "electron mediator", also referred to as a "mediator" is meant a species which regenerates a sensing electrode by supplying or removing charge and transporting it towards the other electrode in the pair of sensing electrodes. In the sensing system of the invention, a potential can be provided between the first and second sensing electrodes and ion flow takes place between these electrodes. This current flow is mediated by the electron mediator, which can be oxidised or reduced to release or absorb electrons. The net result of this, however, is the consumption of one or the other member of the redox couple of the mediator, depending upon the polarity of the potential applied. The rate of consumption of the redox member is dependent upon the magnitude of the ion flow.

For instance, application of a positive potential results in the oxidation of one member of the redox couple which ultimately will become depleted. Once depletion of a redox member of the electron mediator occurs, the reference potential will start to drift, which could limit the lifetime of the measurement unless more mediator is supplied.

A typical electron mediator is a redox couple, for example comprising an ion in two different oxidation states. Exemplary electron mediators are mediators comprising a transition metal in two different oxidation states, such as $Fe^{2+}$ and $Fe^{3+}$. Types of redox couples that may be employed are for example Fe(II)/Fe(III), Ru (III)/Ru (II) and ferrocene/ferrocinium. Specific examples of redox couples that may be employed are ferri/ferrocyanide, ruthenium hexamine and ferrocene monocarboxylic acid. Any suitable electron mediator may be used, for example $[Fe(CN)_6]^{3-/4-}$. Typically, each droplet initially in electrical contact with the first and second sensing electrodes comprises a mediator. For instance, where the second and third droplets are in contact with the first and second sensing electrodes, the second and third droplets comprise a mediator. However, where the first and second droplets are initially in contact with the first and second sensing electrodes, the first and second droplets may comprise a mediator. Thus, in some embodiments the first droplet comprises a mediator. In other embodiments, the system comprises a third droplet of liquid medium and the third droplet comprises a mediator.

As mentioned above, it may be preferred to avoid the presence of analyte in a droplet which is in contact with a sensing electrode. This may be particularly useful in embodiments where the method comprising moving a droplet comprising a sample around the EWOD device, and optionally also recovering the sample, while keeping the droplets of mediator stationary and in contact with the sensing electrodes. Thus, in some embodiments the second droplet and where present the third droplet are substantially free of analyte.

In some embodiments, where a droplet system comprises a first, second and third droplets, all three of the said droplets may be in electrical contact with a sensing electrode. Typically the first droplet is in electrical contact with the first sensing electrode, the second droplet is in electrical contact with the second sensing electrode and the third droplet is in electrical contact with a further sensing electrode. Each droplet within a droplet system may be connected with at least one other droplet in the droplet system via a droplet interface. More generally, where a droplet system comprises N droplets, each of the N droplets may be in contact with a respective sensing electrode. In one embodiment, "N" represents a number between 2 and 10, or a number between 2 and 100. The sensing system may therefore contain at least N sensing electrodes. This arrangement of course has the advantage that electrical measurements may be taken across any droplet interface in the system.

Similarly, where a droplet system comprises N droplets, each of the N droplets may be in contact with one or more actuation electrodes among the array of actuation electrodes, typically with two or more, five or more or ten or more actuation electrodes among the array of actuation electrodes. This enables precise control of the motion and electrowetting behaviour of the droplets.

As mentioned above, the size of the droplets utilised in the method of the invention is not particularly limited. The EWOD device is capable of manipulating droplets up to microliters in size. However, a particular advantage of this invention, which uses electric fields to control the wetting characteristics of the liquid droplets, is that very small droplets can be used. There is no need to employ the larger volumes required to fill microfluidic devices. The sensing system of the invention is perfectly capable of handling picolitre volumes of fluid, and indeed such volumes may be moved very rapidly. Thus, the invention provides a method wherein one or more of the first droplet, the second droplet and where present the third droplet has a volume of less than 1 nL. In some aspects, each of the first droplet, the second droplet and where present the third droplet has a volume of less than 1 nL. Where present, any further droplets may optionally all have volumes of less than 1 nL. In some embodiments, all droplets present within the sensing system have volumes of less than 1 nL. In other aspects, the first, second and where present third or further droplets each have volumes of up to 10 µL, for example from 0.001 nL to 10 µL.

The number of droplets present in the system is not particularly limited, except that the sensing system must comprise a first and a second droplet. Indeed, an advantage of the system is that it can include a large number of droplets. For example, the sensing system of the invention may comprise a system of N droplets where N is at least 10, or at least 100, or at least 1000, or at least 10000. The first, second and third droplets are among the N droplets. Some or all of the N droplets may be arranged in pairs, in contact with one another via a droplet interface comprising a layer of amphipathic molecules. The droplet system may be connected to an ASIC.

Step (a)

Step (a) of the method comprises obtaining an electrical measurement from the first and second sensing electrodes. It should be noted that step (a) is not necessarily the first step performed when operating the sensing system of the invention: additional steps may be performed before step (a) occurs. For example, after steps (a), (b) and (c) have been performed once, the method may be repeated. The method may be repeated a plurality of times. Upon each iteration of the method, the measurement taken in step (a) may be the same or different; and the droplet operation selected in step (b) and performed in step (c) may be the same or different.

Step (a) may comprise taking any electrical measurement from the first and second sensing electrodes, wherein the electrical measurement is as discussed above. Typically, the control system may select the electrical measurement to be taken, for example based on one or more instructions stored in the control system. For instance, in the typical operation of the sensing system of the invention, the control system may direct the performance of steps (a), (b) and (c) according to specified program, for example in order to execute an assay or an analysis of an analyte. However, alternatively, the electrical measurement to be taken may be manually specified by the user.

In order to obtain an electrical measurement, the sensing system must usually comprise some means of electrical contact between the first and second sensing electrodes. However, this is not necessary: for instance, where the electrical measurement determines that a droplet is absent from a particular position, either one or neither of the sensing electrodes is in contact with a droplet; or the first and second electrodes may be in contact with droplets that are not in electrical contact with one another such that no ions may flow between them.

Typically, during step (a), the first and second sensing electrodes are in electrical contact via two or more droplets, contacting one another via a droplet interface. Usually, each such droplet interface comprises at least one transmembrane pore, for example an ion channel. In one aspect, the first droplet (or where present optionally the third droplet) is in electrical contact with the first sensing electrode, and the second droplet is in electrical contact with the second sensing electrode. That is, in one embodiment, the first droplet is in electrical contact with the first sensing electrode and the second sensing electrode is in contact with the second sensing electrode. In another aspect, the sensing system comprises a third droplet and the first sensing electrode is in contact with the third droplet and the second sensing electrode is in contact with the second droplet, and the second and third droplets each contact the first droplet via a droplet interface comprising a transmembrane pore.

Where the first and second sensing electrodes are in contact via one or more droplet interfaces comprising a transmembrane pore, the transmembrane pore(s) typically permit ions to pass through, thus allowing electrical charge to flow between the electrodes and hence allowing a current to flow between the first and second sensing electrodes. In such cases, where an analyte is present and interacts with one of the transmembrane pores, the ion flow between the first and second sensing electrodes is interrupted. Thus, the current flowing between the electrodes can be altered. Thus, in some embodiments, step (a) comprises detecting the current flowing between the first and second sensing electrodes.

In the case where the first and second sensing electrodes are in electrical contact via one or more intervening transmembrane pores, including the first transmembrane pore, the electrical measurement taken between the first and second electrodes (for example a measurement of current flow) will differ depending on whether an analyte is interacting with an intervening transmembrane pore or not. In some embodiments, therefore, step (a) comprises detecting an interaction between the first transmembrane pore and an analyte.

The alteration in the electrical signal (for example the current flowing between the first and second electrodes) can provide more information than simply an indication of the presence of analyte. The value of the electrical signal may indicate which transmembrane pore(s) the analyte is interacting with, if there is more than one candidate. The electrical signal may also indicate the kind of analyte present; for instance, where the analyte is a polymeric species, the precise electrical signal may indicate the monomer unit passing through the pore.

The electrodes which act as the sensing electrodes can be the same as the electrodes forming the array of actuation electrodes. For instance, where two electrodes among the array of actuation electrodes are not applying an actuation signal, they may be employed as the first and second sensing electrodes. In some embodiments therefore the first and second sensing electrodes are electrodes among the array of actuation electrodes. However, as noted above, it may be advantageous to provide a set of sensing electrodes which are separate to the actuation electrodes. In this case, the first and second sensing electrodes are not among the array of actuation electrodes. This latter embodiment is preferred. Thus, in a preferred embodiment of the sensing system of the invention, the electrowetting device comprises:

a first substrate supporting the array of activation electrodes; and a second substrate facing the hydrophobic surface of the insulator layer and supporting the first and second sensing electrodes.

The electrical measurement of step (a) may be performed once or it may be repeated one or more times. Repetition of the electrical measurement is particularly important where the method involves monitoring an aspect of the sensing system. For instance, the method may involve monitoring the concentration of analyte or mediator in a droplet; or the method may comprise monitoring the interaction of an analyte with a transmembrane pore; or the method may comprise monitoring the progress of a reaction within a droplet. In such a case, repeated electrical measurements may be taken. For instance, repeated electrical measurements may be taken in order that the latest measurement may be compared with one or more preceding measurements to indicate a change. Variation in the electrical measurement over time may indicate a loss of analyte or mediator from a droplet; or the depletion of a reaction substrate during a reaction; or the progress of an analyte passing through a transmembrane pore.

In such cases, it will of course not be necessary to apply an actuation signal after each electrical measurement is taken; rather the electrical measurement should be repeated until the information provided by the electrical measurement indicates that action is needed.

Thus, in one important aspect, the invention provides a method as described herein wherein step (a) is repeated one or more times.

In some embodiments, step (a) may be repeated a plurality of times. For instance, step (a) may comprise detecting an interaction between the analyte and the first transmembrane pore by obtaining an electrical measurement. A determination may be performed by the control system to determine the presence, absence or one or more characteristics of the analyte. If the decision is taken to reject that analyte, step (a) may be repeated until a desired analyte is detected before (b) and (c) are performed.

Where an undesired analyte is detected in step (a), preferably where the analyte is a charged analyte, step (a) may further comprise applying a potential across the first and second target electrodes in order to force the analyte detected in step (a) back into the first droplet.

In general, the application of potentials between the first and second sensing electrodes, or any pair of sensing electrodes, which directs the translocation of an analyte may be controlled by stored instructions in the control system.

In some embodiments, step (a) comprises obtaining an electrical measurement indicating the presence of a target analyte. For example, step (a) may comprise obtaining an electrical measurement indicating that a target analyte has passed through the first transmembrane pore from the first droplet into the second droplet.

Step (b)

Step (b) of the method is the decision-making step. In step (b), the electrical measurement obtained by the control system is analysed and the control system determines a droplet operation that should be effected by the sensing system. Typically, the control system determines the next droplet operation that should be effected by the sensing system in order to achieve the outcome specified by the operation system (for example, an assay or an analysis procedure). Described below are various steps by which the control system may select a droplet operation to be performed.

In some embodiments, step (a) comprises detecting the interaction of an analyte with the first transmembrane pore, and step (b) comprises identifying the analyte in whole or in part. For example, where the analyte is a polynucleotide sequence (e.g. DNA or RNA), it may partially enter the transmembrane pore, or may pass entirely through the transmembrane pore. The electrical signals detected during interaction of the transmembrane pore and analyte will vary depending on the part of the sequence that is in contact with the pore. It may not be necessary to determine each component of the analyte before, for example, deciding whether to allow the analyte to pass through the pore entirely into another droplet, or whether to return the analyte to the initial droplet and either await a further interaction with a new analyte molecule to enable a new electrical measurement, or to move the droplet containing the analyte out of the system. Rather, a part of the sequence of the polynucleotide sequence may be enough to enable this decision. Thus, in some embodiments where the analyte comprises a polynucleotide, and step (b) comprises determining the identity of two or more nucleotides present in the polynucleotide sequence. For example, step (b) may comprise determining the identity and optionally also the order of at least two, at least ten, at least twenty, at least 100 or at least 1000 nucleotides in the polynucleotide sequence. In yet other embodiments, step (b) may comprise determining the identity of the whole polynucleotide sequence.

Determination of all or part of a polynucleotide sequence may enable a decision to be taken about whether to reject the sequence or indeed the droplet containing the analyte. For instance, where the purpose of the method of the invention is to identify whether a particular target analyte sequence is present in a sample, if the analyte detected does not correspond to that target analyte, the analyte and indeed the droplet containing it may be rejected. Alternatively, where the detected analyte does correspond to the target analyte, the droplet may be selected for further processing or the analyte itself may be translocated into another droplet and then that droplet may be selected for further processing In other examples, the determination of all or part of a sequence may enable a decision to be taken about whether to reject the analyte or droplet by for instance determining the length of the sequence. Where a long sequence has been fragmented for identification, if it is found that a particular fragment is too short, that fragment or indeed the whole droplet containing that fragment may be of too low quality to use and so may be rejected. It may also be determined that the sequence has been modified and the sequence may be accepted or rejected on that basis.

In some embodiments, step (b) comprises comparing the electrical measurement to a value stored by the control system. A comparison between a measured value and a stored value can indicate a droplet operation, e.g. by indicating that the electrical measurement has risen above or fallen below an expected value or range of values. For instance, where the electrical measurement in step (a) is a measurement of electrical resistance, an electrical resistance which is considerably higher than some reference value may indicate that the first and second sensing electrodes are not in electrical contact and hence may indicate that there is no droplet in contact with either the first or the second electrode. In consequence, the control system may select a droplet operation which brings a droplet into contact with the first or second electrode.

Embodiments where step (b) comprises determining whether a droplet is present at a particular location (in electrical contact with the first or second sensing electrodes) may be useful in controlling the motion of droplets around the sensing system during an assay or analysis sequence of droplet operations. For instance, where an actuation signal has previously been applied to one or more actuation electrodes in order to move a droplet into a position (for instance to move a droplet into contact with another droplet to form a membrane comprising a transmembrane pore), an electrical measurement which indicates whether a droplet is present or absent at the expected location is useful to determine whether or not the actuation signal has successfully moved the droplet into position. The system can thus provide a feedback system: if the droplet is detected at the expected position, step (b) may comprise determining that no further actuation signal is needed, as the assay or sequencing or other step set up by the original droplet movement can proceed. However, if the droplet is not detected at the expected position, step (b) may comprise selecting a droplet operation which would involve moving the droplet into the correct position in order to allow the next experimental step to occur. In this way, the control system can ensure that the sensing system is able to perform experiments on each droplet precisely, reducing the number of erroneous values due to errors such as failure to form contact between droplets.

In other examples, where the electrical measurement is taken between the first and second sensing electrodes, comparison of the measured value with a stored value may indicate whether a droplet interface comprising a transmembrane pore has successfully formed. If the droplet interface has not successfully formed (for example if the membrane has ruptured), or if a transmembrane pore has failed to insert into the membrane between two droplets between the first and second sensing electrodes, comparison of an electrical measurement taken across the sensing electrodes will indicate that. Accordingly, the comparison can indicate that two droplets have fused and should therefore be ejected from the system, or the comparison may indicate that a transmembrane pore has failed to insert and hence that the droplet containing the transmembrane pore may be faulty and should be ejected from the system. Step (b) comprises selecting a droplet operation accordingly, for example to eject the fused droplets or the droplet containing the faulty pore. Again, this process improves the functioning of the system by avoiding erroneous results.

In another example, where the electrical measurement is taken between the first and second sensing electrodes where those electrodes are in electrical communication across one or more droplet interfaces via one or more transmembrane pores, such comparison may indicate a loss of mediator. For example, where the current flowing between the electrodes in the absence of analyte is found to be particularly low compared to a stored or reference value, that may indicate that the amount of mediator in the droplets has fallen too low. Thus, a droplet operation may be selected which involves adding a droplet containing additional electron mediator to one or more of the droplets across which the electrical measurement was taken.

The control system typically stores instructions to enable the control system to select a suitable droplet operation based on the comparison. For example, the instructions stored in the control system may indicate that no droplet operation is required if the electrical measurement is within a particular tolerance of the stored value, and may indicate that a manipulation must be performed if the value is above or below that tolerance; and moreover may store sufficient information to select which droplet(s) must be actuated in order to achieve that outcome.

Thus, in a particular aspect of this embodiment, the method comprises comparing the electrical measurement of step (a) to a value stored by the control system and further comprises selecting a droplet operation based on the comparison between the electrical measurement and the stored value, according to one or more instructions stored in the control system.

In many embodiments, the electrical measurement is not compared to an absolute reference value permanently stored in the control system. Rather, the method comprises monitoring the electrical measurement for a change which may indicate that a droplet operation is required. For example, step (b) may comprise comparing the electrical measurement to a previous electrical measurement in order to determine whether the system has undergone a change and a droplet operation is required to address the change. Thus, in some embodiments step (a) is repeated one or more times to obtain a plurality of electrical measurements, and step (b) comprises comparing one or more electrical measurements among the plurality of electrical measurements with one or more other electrical measurements among the plurality of electrical measurements.

Typically, where the method comprises monitoring the electrical measurement, the method may involve determining a trend in the electrical measurement rather than comparing the electrical measurement to a single previous value, because individual electrical measurements can be subject to fluctuations. More usually, therefore, step (b) comprises comparing the electrical measurement to several previous electrical measurements taken during repetitions of step (a); e.g. step (b) may comprise comparing the electrical measurement to an average of several previous electrical measurement taken during repetitions of step (a). For instance, an average of several electrical measurements may be compared to an average of several previous electrical measurements obtained by repetition of step (a). This enables the control system to detect a trend in the electrical measurement over time.

Where a trend is detected, it may indicate a loss of electron mediator, a degradation of the analyte present; a loss of analyte, a loss of substrate during a reaction, or any other alteration in conditions within a droplet in electrical contact with the first or second sensing electrodes. The control system may in some embodiments then select a droplet operation to redress that change, for example by adding more electron mediator or analyte or substrate to the droplet concerned. Another exemplary droplet operation which could redress that change would be to replace one or more of the droplets concerned with a new droplet comprising, for instance, analyte, substrate or electron mediator. In yet other embodiments, the control system may select a droplet operation which terminates that particular process, for example by disposing of degraded analyte e.g. by removing a droplet comprising degraded analyte from the sensing system.

In some embodiments, therefore, step (a) is repeated a plurality of times to obtain a plurality of electrical measurements; and step (b) comprises:
  comparing one or more of the electrical measurements with one or more of the other electrical measurements among the plurality of electrical measurements;
  determining an alteration in the electrical measurement detected over time; and
  selecting a droplet operation to reverse the alteration in the electrical measurement.

In some aspects, step (b) comprises determining a physical or chemical property of the first droplet and/or the second droplet and/or, where present, the third droplet. The physical or chemical property may be monitored as described above. In one embodiment of this aspect, step (b) further comprises selecting a droplet operation in order to modify or maintain said physical or chemical property of the first droplet and/or the second droplet and/or, where present, the third droplet.

Exemplary physical properties that may be measured or monitored include conductivity. Exemplary chemical properties that may be measured or monitored include ion concentration. Thus, in a one aspect of the method of the invention, step (b) comprises determining the ion concentration of the first droplet and/or the second droplet and/or, where present, the third droplet. Typically, in this embodiment, step (b) comprises determining the ion concentration of the first or the second droplet.

In one embodiment, step (b) comprises selecting a droplet operation in order to increase or decrease the ion concentration of the first droplet and/or the second droplet and/or, where present, the third droplet. For example, the droplet operation may involve moving a further droplet having a higher ion concentration into contact with the first droplet or the second droplet or, where present, the third droplet in order to fuse the further droplet with said first or second or third droplet in order to increase its ion concentration.

In some embodiments, the said the ion concentration is the concentration of an electron mediator species. In other embodiments, the said ion concentration is the concentration of a charged analyte species. However, the precise ion concentration need not be determined; in some embodiments, step (b) comprises establishing whether an analyte is present. For example, step (b) may comprise determining whether an analyte is present in the first droplet and optionally determining the concentration of an analyte, in the first droplet. Step (b) may comprise selecting a droplet operation which involves ejecting the droplet (e.g. the first droplet) from the sensing system if it is found that it does not contain analyte or a sufficient concentration of analyte. Alternatively, in these circumstances, step (b) may comprise selecting a droplet operation to increase the concentration of analyte in the droplet (e.g. the first droplet).

In some embodiments, step (b) comprises determining the quality of an analyte present in the first droplet. By "determining the quality" means that it is determined whether the analyte is able to give a sufficiently good signal or not. For example, where the analyte is a polymer chain comprising multiple polymer units, step (b) may comprise determining the length of the polymer chain (e.g. the number of polymer units). This can be done by, for example, monitoring the electrical signal produced as the analyte passes from the first droplet to the second droplet via the first transmembrane pore: if the analyte comprises short chains, this will be evident from the short time over which each interaction with the first transmembrane pore is observed. Thus, in some embodiments, the step of analysing an electrical signal obtained in step (a) may comprise analysing a plurality of electrical measurements taken in step (a). If it is determined from such analysis that, for example, the analyte present in the first droplet is of insufficient quality (for instance, said analyte comprises insufficiently long polymer chains), the control system may select a droplet operation whereby the first droplet containing the analyte is removed from the sensing system.

In some embodiments, therefore, step (b) comprises deciding whether to keep or dispose of a droplet, usually the first droplet. By "keep" is meant "keep in the sensing system, for instance to perform further experiments or analysis upon". By "dispose of" is meant to remove the droplet from the sensing system, either to be collected and stored or simply to be thrown away. Where step (b) comprises deciding whether to keep or dispose of a droplet, step (b) further comprises selecting a droplet operation which maintains the droplet within the sensing system or removes it from the sensing system accordingly.

In some embodiments, the analysis performed on the electrical measurement in step (b) provides information which is used to determine a further experimental procedure that may be performed on the droplet, according to one or more instructions stored in the control system. For instance, the analysis of the electrical measurement or measurements may indicate that the droplet comprises analyte but that the analyte concentration is low. In that case, the control system may determine that a procedure to increase the concentration of analyte should be performed, and will select a droplet operation to increase the concentration of analyte in the droplet, for example by fusing it with a droplet containing additional analyte. In some embodiments, therefore, step (b) comprises selecting a further experimental procedure to perform on the first droplet; and selecting a droplet operation to bring the first droplet into contact with one or more droplets to enable that experiment to be performed.

In one embodiment, where step (a) comprises detecting an interaction between an analyte (typically a polymeric analyte such as a polynucleotide e.g. DNA or RNA), step (b) may comprise deciding (based on the measurement taken in a) whether to pass the polymeric analyte to a further droplet or to reject the analyte. Where step (b) comprises deciding to pass the polymeric analyte to a further droplet, that may be achieved by passing the analyte to the second droplet before or after connecting a further droplet to the second droplet. The further droplet can form a further droplet interface with the second droplet, comprising a second transmembrane pore, and can therefore receive the analyte from the second droplet.

On the other hand, where step (b) comprises deciding to reject the analyte, this can be achieved by reversing the potential across the droplet interface; for example across an interface between the first and second droplets. This allows the analyte (typically a charged analyte) to be prevented from translocating into the second droplet. A droplet operation may then be applied in step (c) to move the first droplet away from the second droplet, and optionally may comprise moving the first droplet out of the sensing system.

Where step (a) comprises detecting the presence of a target analyte (for example detecting the passage of the target analyte from the first to the second droplet) it may be desired to prevent the analyte from returning to the first droplet. In that case, the droplet operation selected in step (b) may comprise disconnecting the first and second droplets by moving either the first droplet or the second droplet such that the first and second droplets no longer contact one another. It may also be desired to bring the target analyte into contact with another transmembrane pore. Thus, the droplet operation selected in step (c) may further comprise placing the second droplet comprising the target analyte into contact with a further droplet to form a further droplet interface, which further droplet interface comprises a membrane and a second transmembrane pore.

Step (b) may comprise selecting two or more droplet operations. For example, step (b) may comprise selecting a droplet operation to place the second droplet, containing a target analyte, in contact with a further droplet. Step (b) may alternatively or additionally comprise selecting a droplet operation in order to place a new droplet in contact with the first droplet.

Step (c)

In step (c), a droplet operation is performed.

Step (c) may or may not be performed automatically following step (b). That is, in some embodiments, step (c) is not performed automatically following step (b), and a user input is required in order to proceed from step (b) to step (c). In other embodiments, A step (c) is performed automatically after step (b). That is, having selected a droplet operation in step (b), the droplet operation is then performed by the control system without requiring further user intervention.

This latter embodiment is preferred as it enables the sensing system to operate very rapidly.

It should firstly be noted that the droplet operation selected in step (b) and performed in step (c) may comprise doing nothing. For example, in particular embodiments where a property of a droplet (e.g. ion or analyte concentration) is monitored and is found, upon analysis during step (b), to be adequate then no adjustment of the system is required. In that case, the droplet operation selected may be a null droplet operation, and accordingly the actuation signal applied during step (b) is unchanged from any previous actuation signal applied to the actuation electrodes in electrical contact with the droplet system in question.

In other embodiments, a droplet operation comprises a manipulation of the droplet system, a droplet system comprising at least a first droplet and a second droplet.

The droplet operation may or may not involve moving a droplet. In some embodiments, the droplet operation does not involve moving any droplet. For example, the droplet operation may comprise applying an actuation signal to an actuation electrode simply in order to place a droplet in contact with the actuation electrode into an energised state. This may cause a droplet interface comprising a membrane to pull apart. In another example, the droplet operation may comprise lowering the energy of a droplet in contact with an actuation electrode to a lower-energy state than its previous state, thus allowing the droplet to relax and adopt the shape of its lower-energy state. This may cause a droplet interface to form, if the said droplet thus contacts another droplet via a droplet interface comprising a layer of amphipathic molecules.

In some aspects, step (c) comprises moving a droplet of liquid medium upon the hydrophobic surface (that is, the hydrophobic surface of the first substrate in the EWOD device). The droplet that is moved is referred to as an actuated droplet. Accordingly, in some aspects step (c) comprises moving an actuated droplet of liquid medium upon the hydrophobic surface. Typically, the actuated droplet is the first or the second or where present the third droplet; for example, the actuated droplet may be the first droplet. In other embodiments, the actuated droplet may be the second droplet. In yet other embodiments, step (c) comprises moving two or more droplets of liquid medium upon the hydrophobic surface. In such embodiments, the actuated droplets may include the first and/or the second and/or where present the third droplet; for example, the actuated droplets may include the first and second droplets.

Figure 10A:
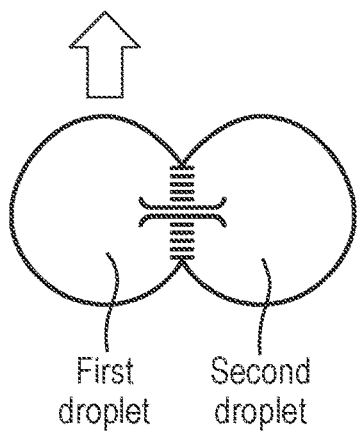
FIG. 10 is a diagram of exemplary droplet operations by which a first and second droplet may be separated.
Figure 10B:
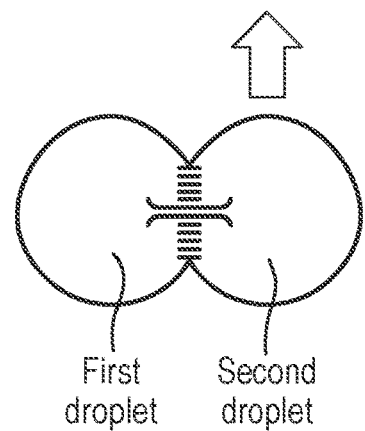
Figure 10C:
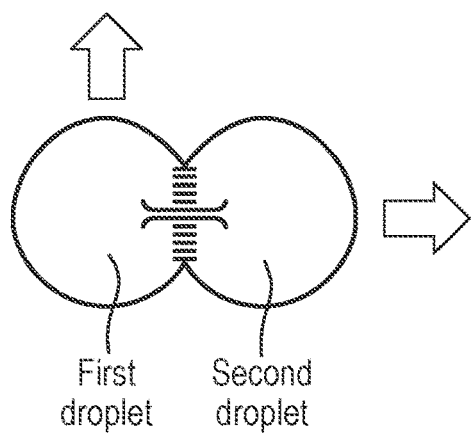

In some embodiments, the droplet operation performed in step (c) comprises separating the actuated droplet at a droplet interface from a further droplet of liquid medium, which further droplet may be the first, second or where present the third droplet. Said droplet interface comprises a layer of amphipathic molecules. Where the droplet interface comprises a transmembrane pore, the transmembrane pore may be destroyed during the separation of the droplet interface. During the separation of the droplet interface, the further droplet may or may not be moved by an actuation signal (i.e. the further droplet may or may not itself be an actuated droplet). In an example of this process, the droplet operation may comprise separating the first droplet from the second droplet, in which droplet operation an actuation signal is applied to move the first and/or the second droplets away from one another. The options are illustrated in FIGS. 10a to 10c. In these figures, the arrows indicate the motion of a droplet. In FIG. 10a, the first droplet is the actuated droplet and is moved away from the second droplet. In FIG. 10b, the second droplet is the actuated droplet and is moved away from the first droplet. In FIG. 10c, the first and second droplets are both actuated droplets and they are moved away from each other.

Figure 11A:
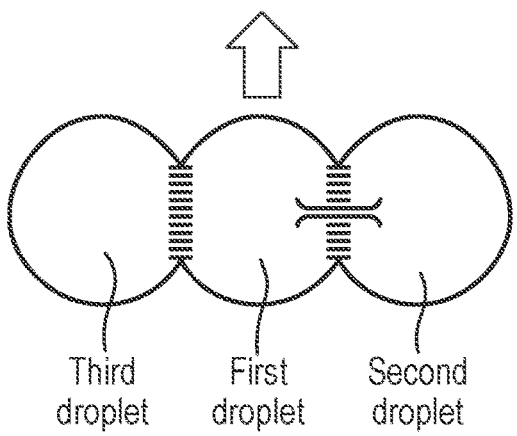
FIG. 11 is a diagram of exemplary droplet operations by which a first, second and third droplet may be separated.
Figure 11B:
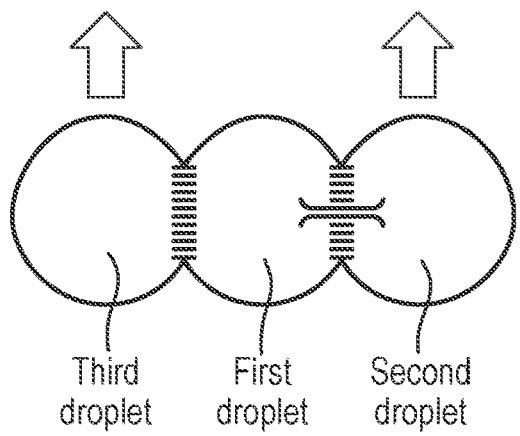

In one aspect, step (c) comprises separating the actuated droplet at a plurality of droplet interfaces from a plurality of further droplets of liquid medium, which further droplets may include the first, second or where present the third droplet, and each of said droplet interfaces comprises a layer of amphipathic molecules. Examples of such a process are illustrated in FIG. 11. These examples concern an initial construct wherein the first droplet contacts the second droplet and the third droplet via droplet interfaces, each comprising a layer of amphipathic molecules. In the first example, shown in FIG. 11a, the first droplet is separated from the second and third droplets at two interfaces by an actuation signal applied to move only the first droplet. In the second example, both the second and third droplets are actuated by the actuation signal and they move away from the first droplet.

In any of the above aspects, the said one or more droplet interfaces may each comprise a bilayer of amphipathic molecules, and step (c) comprises separating the said bilayer. Where a plurality of droplet interfaces are separated, each one may independently comprise a bilayer of amphipathic molecules.

Figure 12A:
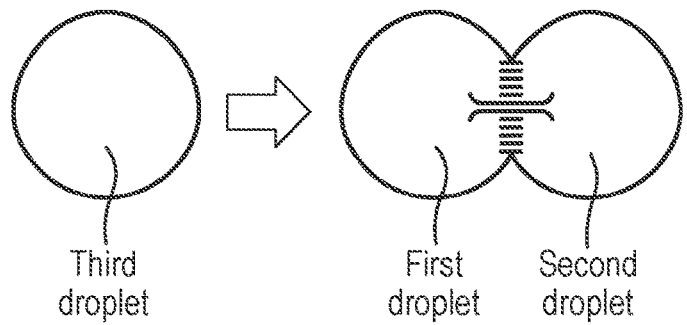
FIG. 12 is a diagram of exemplary droplet operations by which a plurality of bilayers may be formed.

In some embodiments, step (c) comprises bringing one or more droplets into contact. Thus, step (c) may comprise placing the actuated droplet in contact with a further droplet of liquid medium to form a droplet interface, which further droplet may be the first, second or where present the third droplet. The droplet interface formed in this embodiment comprises a layer of amphipathic molecules. In these embodiments, the further droplet may or may not be moved by an actuation signal (i.e. the further droplet may or may not be an actuated droplet also). Where one of the droplets that are brought into contact with another droplet comprises a transmembrane pore, the transmembrane pore may insert into the formed droplet interface during or after step (c). In one example of this process, step (c) comprises bringing a third droplet into contact with the first droplet, in which process an actuation signal is applied to the third droplet to move it towards the first droplet. This process is illustrated in FIG. 12a, where the arrow indicates the direction in which the actuated droplet is moved by the actuation signal.

Figure 12B:
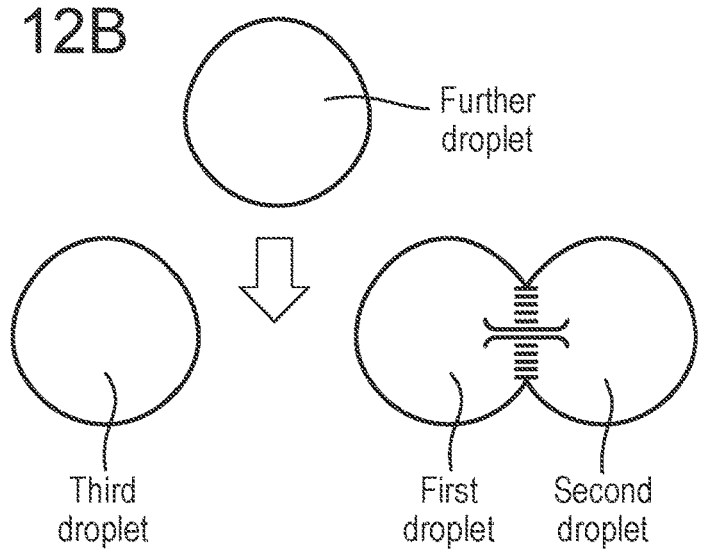
Figure 12C:
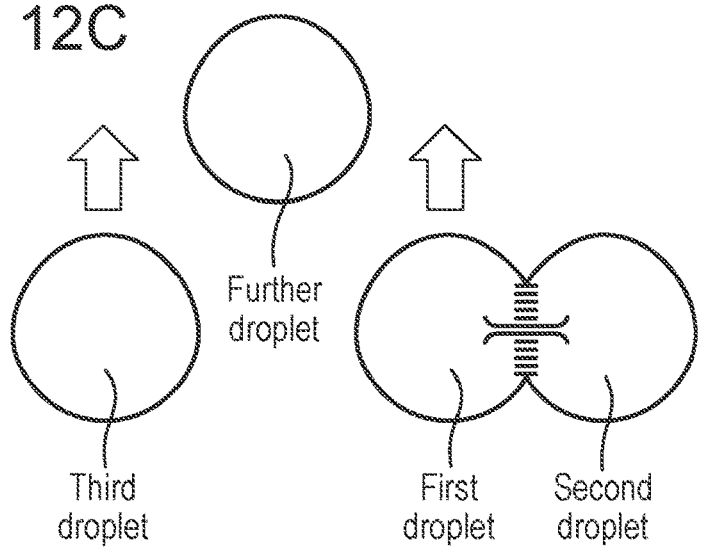

In a further aspect, step (c) may comprise placing the actuated droplet in contact with a plurality of further droplets of liquid medium to form a plurality of droplet interfaces, which further droplets may include the first, second or where present the third droplet. For example, step (c) may comprise moving a further droplet of liquid medium into contact with the first and the third droplets in order to form a first droplet interface between the first droplet and the further droplet, and a second droplet interface between the third droplet and the further droplet, wherein each interface comprises a layer of amphipathic molecules. In this case, an actuation signal may be applied to the further droplet, in order to move it into contact with the first and third droplets. This is illustrated in FIG. 12b. Alternatively or additionally, however, an actuation signal may be applied to the first and third droplets in order to bring them into contact with the further droplet; this is illustrated in FIG. 12c.

Typically, each droplet interface formed when a droplet of liquid medium is brought into contact with another droplet of liquid medium comprises a layer of amphipathic molecules. In one aspect, the droplet interface formed (or, where a plurality of droplet interfaces are formed, one or more of the droplet interfaces formed) in step (c) comprises a bilayer of amphipathic molecules, and step (c) comprises forming the said bilayer.

The actuation signals that are selected to energise the actuated droplet (and optionally any other droplet present in the sensing system) may be alternating (AC) actuation voltage signals. In general, the use of AC actuation signals in an electro-wetting device is known to be advantageous for manipulating droplets.

Where step (c) involves the formation of a droplet interface, potentials are applied to selected activation electrodes to bring the actuated droplet into contact with another droplet. In the simplest embodiment, this may be done simply by selecting the actuation potentials in order to move the actuated droplet. However, in this approach it can be difficult to maintain the interface between the droplets as the droplets can show a tendency to merge.

Accordingly, in a preferred aspect of the embodiment where step (c) comprises forming a droplet interface between the actuated droplet and another droplet, step (c) further comprises applying actuation signals to selected actuation electrodes among the array of activation electrodes to place the actuated droplet and/or the another droplet in an energised state such that the droplets do not contact each other, in which state the shape of said droplets is modified compared to when in a lower energy state; and step (c) further comprising changing the actuation signals applied to the actuation electrodes to lower the energy of said one or both droplets into the lower energy state so that said one or both droplets relax into a shape which differs from their shape in the energised state and thus the two droplets contact each other thereby forming a droplet interface. This embodiment of step (c) improves the reliability of formation of the droplet interface, compared to attempting to bring two droplets into contact directly by applying actuation signals that move the entire droplets towards one another.

When a droplet relaxes from its de-energised state, its centre of mass tends not to move. Rather, it is the edges of the droplet which relax and hence move, for instance towards another droplet. Typically, therefore, step (c) comprises placing the actuated droplet and/or the another droplet in an energised state sufficiently close together that when the energy of the actuated droplet and/or the another droplet is lowered, the droplets will contact one another. That is, in step (c) the distance apart at which the actuated droplet is placed to another droplet before the energy of the actuated droplet and/or the another droplet in an energised state is reduced is less than the combined radii of the droplets in their lower-energy states.

By way of background, it is noted that in a relaxed state of the droplets (i.e. where they are not electro-wet by the application of actuation signals to the actuation electrodes), each droplet would take the shape of lowest surface energy, which would generally be a circular shape where the hydrophobic surface of the insulator layer has uniform properties.

In this embodiment of step (c), a single one of the actuated droplet and the another droplet may be placed in an energised state. However, preferably both droplets are placed in the energised state. As a result, the surfaces of both droplets relax into the shapes they adopt in the lower-energy state and contact each other to form the droplet interface. In this manner, relaxation of both droplets is used to form the droplet interface, which further increases the reliability of formation.

The applied actuation signals may be changed in any manner to de-energise the droplet(s), including the actuated droplet. Where the actuation signals that are applied to electro-wet the actuation electrodes are AC actuation signals, then the change is desirably to replace the AC actuation signals which energised the actuated droplet or droplets by DC potentials, for example a ground potential, or by floating potentials. This has the benefit that AC signals are no longer applied to the actuation signals, which assists in forming of a droplet interface because the presence of AC electric fields resulting from AC signals increases the risk of the droplet interface rupturing and causing the droplets to fuse when the surfaces of the droplets come into contact.

Other changes which de-energise the actuated droplet or droplets may alternatively be made. An alternative is to remove all power from the array of actuation electrodes. However, it may be preferable to apply a DC potential to assist in shielding the droplet interface from unwanted environmental electro-magnetic interference.

The present inventors have appreciated that it is preferable not to de-actuate the droplets in the conventional way by applying AC voltage waveforms, since resultant perturbations may damage a droplet interface or may interfere with electrical measurements through the droplet interface.

Figure 13A:
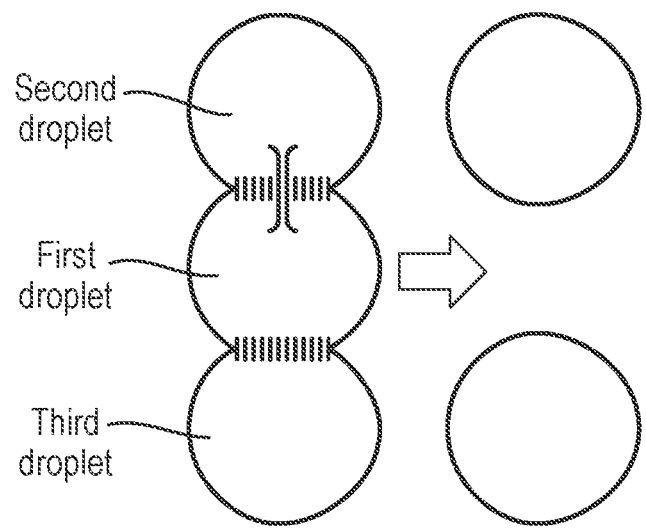
FIG. 13 is a diagram of exemplary droplet operations by which a plurality of bilayers may be formed and a plurality of bilayers broken.

The droplet operation may move one or more actuated droplets away from one or more droplets and into contact with one or more other droplets. Thus, in some embodiments, step (c) comprises separating the actuated droplet at a droplet interface as described above and placing the actuated droplet in contact with a further droplet of liquid medium as described above. For example, step (c) may comprise applying an actuation signal in order to move the first droplet away from the second droplet and separating the droplet interface formed between the first and second droplets, and moving the first droplet into contact with a third droplet, forming a droplet interface comprising a layer of amphipathic molecules between the first and the third droplets. More complex examples are illustrated in FIG. 13.

In some embodiments, step (c) comprises fusing two or more droplets together. By "fusing" is meant that the droplets are combined to form a single liquid droplet, that is, a droplet not separated into compartments by a layer or layers of amphipathic molecules. Where two or more droplets are fused, their contents mix. By contrast, when droplets are placed in contact via a droplet interface, the contents of the droplets does not mix unless a transmembrane pore inserts into the membrane and permits transport of matter across the membrane. In such embodiments, if fusion does not occur upon contact of the droplets and a droplet interface forms instead, a voltage may be applied across the said droplet interface to rupture the droplet interface and cause the droplets to fuse.

In some embodiments, therefore, step (c) comprises fusing the actuated droplet with a further droplet of liquid medium, which further droplet may be the first, second or where present the third droplet. For example, step (c) may comprise fusing the actuated droplet with the first droplet, where the actuated droplet comprises analyte, in order to add analyte to the first droplet. In another example, step (c) may comprise fusing the actuated droplet with the second droplet, where the actuated droplet comprises an electron mediator, in order to add electron mediator to the second droplet.

In order to fuse droplets, it is preferred that a layer of amphipathic molecules does not form between the actuated droplet and the droplet with which the actuated droplet is to be combined in step (c). Accordingly, where step (c) comprises fusing the actuated droplet with another droplet, the actuated droplet preferably does not comprise an external layer of amphipathic molecules. However, if the actuated droplet does comprise an external layer of amphipathic molecules and/or a layer of amphipathic molecules forms between the actuated droplet and another droplet, the actuated droplet may nonetheless be forced to fuse with the another droplet by applying an actuation signal which forces the actuated droplet and the another droplet together.

As explained above, the actuated droplet may comprise one or more of an electron mediator, an analyte and an experimental substrate (among other options). In one embodiment the actuated droplet comprises an electron mediator. In another embodiment, the actuated droplet comprises an analyte. In yet another embodiment, the actuated droplet comprises an experimental substrate. An "experimental substrate" may be, for instance, a nutrient to be provided to a cell population contained within a droplet or droplets. An experimental substrate may alternatively be a reagent required for an experimental procedure, for example a reagent required for a PCR procedure. Thus, the droplet operation performed in step (c) may allow a reaction to progress. Alternatively, the droplet operation performed in step (c) may halt a reaction for example where the reagent included in the actuated droplet is a reagent capable of quenching a reaction occurring in the another droplet. In yet another embodiment, the actuated droplet that is to be fused with another droplet may comprise only additional liquid medium; this may be useful in washing the contents of the another droplet, or diluting the another droplet if required.

In a further embodiment, the droplet operation performed in step (c) may comprise splitting a droplet into two or more parts. For example, step (c) may comprise splitting the first droplet or the second droplet or where present the third droplet into two or more parts. In one embodiment, step (c) comprises splitting the first droplet or the second droplet or where present the third droplet into two parts. This may be useful where a large droplet of analyte has formed, and the droplet can be split into two or more smaller droplets to enable the analyte to be analysed using two or more different procedures at the same time.

In some embodiments, the first droplet is not moved during step (c). The first droplet is typically the droplet comprising analyte. That is, in some embodiments the method of the invention involves keeping the analyte stationary and moving other droplets which may comprise transmembrane pores capable of interacting with and hence analysing the analyte to the analyte. This represents a reversal in the approach employed in devices such as described in WO 2014/064443: rather than providing the sample to an array of transmembrane pores, the transmembrane pores are brought to the analyte. One advantage of this approach is that the speed of the analysis procedure can be optimised. Where a large droplet of sample is employed, a plurality of small droplets may conveniently and quickly be brought to the sample in order to analyse it. However, if small droplets of sample are employed, they may more conveniently be manoeuvred around the sensing system by droplet operations.

In some embodiments, step (c) comprises separating the first droplet from the second droplet, wherein the second droplet comprises a target analyte. This may be achieved by applying an actuation signal to move the first and/or the second droplet.

In some embodiments, step (c) comprises bringing the second droplet into contact with a further droplet, wherein the second droplet comprises a target analyte. In these embodiments, a droplet interface comprising a membrane and typically also a second transmembrane pore forms between the second droplet and the further droplet. This may allow the target analyte to move through the second transmembrane pore.

Where two or more droplet operations were selected in step (b), step (c) may comprise applying an actuation signal to the array of actuation electrodes to effect the two or ore droplet operations.

In some embodiments, where step (c) comprises connecting a further droplet with any of a first, second or third droplet within a droplet system via a droplet interface, the further droplet may have a different osmotic potential to the said first, second or third droplet to which it is connected. In some embodiments, the further droplet may have a higher osmotic potential (i.e. a higher ion concentration) than the said first, second or third droplet to which it is connected. In other embodiments, the further droplet may have a lower osmotic potential (i.e. a lower ion concentration) than the said first, second or third droplet to which it is connected. Thus, water may pass from or to the further droplet depending on the osmotic potential difference across the droplet interface. In this case, a droplet operation can achieve dilution or concentration of a droplet within the system.

Exemplary Method 1: Recovery of Analyte

A particular advantage of the invention is that the droplets comprising analyte are not enclosed, meaning that they can be recovered after operation of the system. Moreover, the droplets comprising analyte need not be the same droplets as the droplets which are in electrical contact with the first and second sensing electrode. Instead, the droplet comprising analyte may be connected to the first and second electrodes via further droplets. The droplet comprising analyte is typically the first droplet, and it contacts the second and third droplets (which are respectively in contact with the first and second electrodes) via membranes.

In this embodiment, the fluid medium may be polar and the droplets of liquid medium apolar, but more typically the fluid medium is apolar and liquid medium is the polar medium.

Accordingly, in a preferred aspect, the invention provides a method of operating a sensing system according to any preceding claim, wherein the sensing system comprises:
(i) an electrowetting device, which electrowetting device comprises:
an array of actuation electrodes,
an insulator layer covering the actuation electrodes and having an outermost hydrophobic surface;
a first sensing electrode; and
a second sensing electrode;
(ii) disposed on the hydrophobic surface,
an apolar fluid medium,
a first, second and third droplet comprising a polar liquid medium,
wherein the first and/or the second and/or the third droplet comprises a layer of amphipathic molecules at an interface between said first and/or second and/or third droplet and the fluid medium;
the first droplet is in contact with the second droplet via a droplet interface and with the third droplet via a droplet interface;
each droplet interface comprises a layer of amphipathic molecules;
at least the interface between the first droplet and the second droplet comprises a transmembrane pore;
the first droplet comprises an analyte;
the second and third droplets comprise an electron mediator; and the second and third droplets are in electrical contact with the second sensing electrode and the first sensing electrode respectively;
  (iii) a control system configured to obtain an electrical measurement from the first and second sensing electrodes, and to apply an actuation signal to the array of actuation electrodes;
wherein the method comprises
  a) obtaining an electrical measurement from the first and second sensing electrodes;
  b) analysing the electrical measurement and then selecting a droplet operation based on the electrical measurement according to one or more instructions stored in the control system; and
  c) applying an actuation signal to an actuation electrode to effect the droplet operation.

Thus, the initial droplet arrangement corresponds to that shown in FIG. 11. Generally, though, the droplet interface between the first droplet and the third droplet also comprises a further transmembrane pore. Typically, the further transmembrane pore is an ion channel. In a preferred aspect, the interface between the first droplet and the third droplet comprises a plurality of ion channels, for example at least 10 ion channels. The number of these ion channels is typically high, for example at least ten times or at least 100 times or 1000 times or 10,000 times the number of transmembrane pores present in the interface between the first and second droplets.

In some embodiments, the said ion channels are not permeable to the electron mediator. Ion channels may be impermeable to the electron mediator because, for example, the channels are too narrow or they comprise an electrostatically charged region which discourages passage of the electron mediator.

In this preferred aspect, the first droplet comprising analyte can be moved without interfering with the droplets in contact with the electrodes. Thus, in one aspect the droplet operation selected in step (b) and performed in step (c) comprises moving the first droplet and separating the first droplet from the second and/or third droplets. This is shown in FIG. 11a. The removed first droplet comprising analyte may be replaced with another droplet, which may also comprise analyte. Thus, the method may further comprise moving a further droplet comprising an analyte into contact with the second and third droplets to form a droplet interface between each of the second and third droplets and the further droplet, wherein each droplet interface comprises a layer of amphipathic molecules.

Figure 13B:
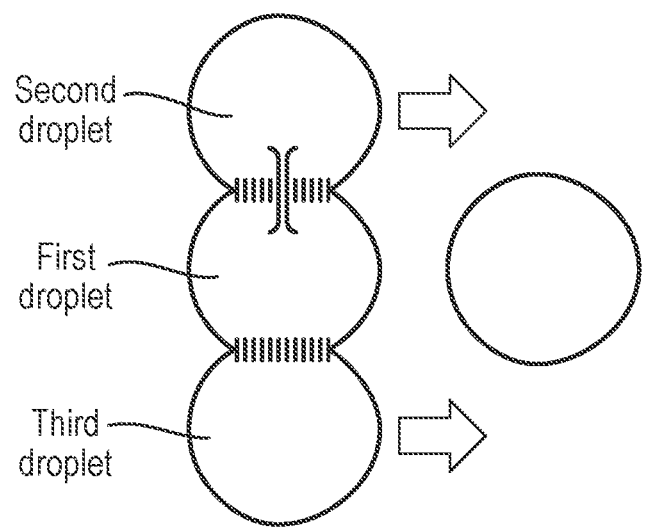

Alternatively, the first droplet comprising analyte can be kept stationary while the second and third droplets comprising electron mediator are moved. Thus, in one aspect the droplet operation selected in step (b) and performed in step (c) comprises moving the second and/or third droplets to separate the second and/or third droplets from the first droplet. This is shown in Figure (b). The second and third droplets may be moved into contact with another droplet comprising analyte, to enable that droplet to be sensed. Thus, in some embodiments, the droplet operation further comprises moving the second and/or third droplets into contact with a further droplet comprising analyte to form a droplet interface between the second and/or third droplet and the further droplet, wherein the interface(s) comprise a layer of amphipathic molecules. This is shown in FIG. 13b.

Not only may the initial second and third droplets be moved away from the first (stationary) droplet comprising analyte, but another pair of droplets containing electron mediator may be moved into position to sense the first droplet. Thus, in some embodiment, the method further comprises moving a fourth and optionally also a fifth droplet into contact with the first droplet to form a droplet interface between the fourth and where present the fifth droplet and the first droplet, wherein the droplet interface or droplet interfaces comprise a layer of amphipathic molecules. In this case, usually the fourth and where present optionally also the fifth droplets comprise an electron mediator.

A useful aspect of this embodiment is that the droplets comprising analyte are not sequestered within a chamber; they can be manipulated to an edge of the EWOD devices where they can be stored or removed and kept. Thus, in a preferred aspect, the method of the invention may comprise recovering the first droplet. By "recovering" such a droplet is meant that the first droplet is not disposed of once the method is finished. Rather, the first droplet is stored, optionally in the sensing system; alternatively the droplet is removed from the sensing system for storage elsewhere.

In a particularly preferred embodiment, the method of the invention comprises recovering substantially all droplets comprising an analyte. This is useful where the analyte is scarce or valuable, or must be retained for future analysis.

Exemplary Method 2: Regeneration of Electrode

As has been explained above, a particular advantage of the invention is that the portions of electron mediator which permit communication between the first and second sensing electrodes are not contained within inaccessible chambers. This is a problem for the devices such as are described in WO 2014/064443, as over time the electron mediator decays (specifically, the $Fe^{3+}$ decays to $Fe^{2+}$ which cannot easily be re-oxidised) and fresh mediator cannot be added. This is not a problem for the sensing system of the invention as the electron mediator is contained in droplets to which material can be repeatedly added, or which can be exchanged for droplets of fresh electron mediator.

Not only can electron mediator be added, but the electrical measurements obtained by the first and second sensing electrodes can be monitored to determine whether the electron mediator has deteriorated and whether fresh electron mediator is required. Thus, the electrodes and specifically the electron mediator enabling communication between the first and second sensing electrodes can be regenerated.

Accordingly, in a preferred aspect the invention provides a method of operating a sensing system, wherein the sensing system comprises:
  (i) an electrowetting device, which electrowetting device comprises:
    an array of actuation electrodes, and
    an insulator layer covering the actuation electrodes and having an outermost hydrophobic surface;
    a first sensing electrode; and
    a second sensing electrode;
  (ii) disposed on the hydrophobic surface:
    an apolar fluid medium,
    a first, second and optionally a third droplet comprising a polar liquid in the fluid medium;
    the first and/or the second droplet comprises a layer of amphipathic molecules at an interface between said first and/or second droplet and the fluid medium;
    the first droplet is in contact with the second droplet via a droplet interface, or the third and second droplets are each in contact with the first droplet via a droplet interface;
    the or each droplet interface comprises a layer of amphipathic molecules;

at least one of the droplet interfaces comprises a transmembrane pore;
the first droplet comprises an analyte;
one of the droplets, optionally the second droplet comprises an electron mediator;
the first or where present optionally the third droplet is in electrical contact with the first sensing electrode; and
the second droplet is in electrical contact with the second sensing electrode;
(iii) a control system configured to obtain an electrical measurement from the first and second sensing electrodes, and to apply an actuation signal to the array of actuation electrodes;
wherein the method comprises
a) obtaining an electrical measurement from the first and second electrodes, and repeating this step a plurality of times to obtain a plurality of electrical measurements;
b) comparing one or more of the electrical measurements with one or more of the other electrical measurements among the plurality of electrical measurements, determining an alteration in the electrical measurement detected over time that is attributable to a loss of electron mediator in the droplet, optionally in the second droplet, and selecting a droplet operation to increase the concentration of electron mediator in that droplet, optionally the second droplet; and
c) applying an actuation signal to an actuation electrode to effect the droplet operation.

In one embodiment, the droplet operation to increase the concentration of electron mediator in the second droplet is an operation whereby the second droplet is moved out of electrical contact with the second sensing electrode, and a new droplet comprising a higher concentration of mediator is moved into electrical contact with the second sensing electrode.

In another embodiment, the droplet operation comprises moving an actuated droplet of fluid medium upon the hydrophobic surface and fusing the actuated droplet with the droplet comprising the electron mediator, which is optionally the second droplet, wherein the actuated droplet also comprises an electron mediator. Typically, the actuated droplet comprises a high concentration of electron mediator. For example, the actuated droplet may comprise a higher concentration of electron mediator than is present in the droplet comprising the electron mediator, which is optionally the second droplet.

In one embodiment, the sensing system comprises a first droplet and a second droplet; the first droplet is in contact with the second droplet via a droplet interface, which droplet interface comprises a layer of amphipathic molecules and a transmembrane pore; and the first droplet is in electrical contact with the first sensing electrode; and the second droplet is in electrical contact with the second sensing electrode. In this embodiment, the droplet comprising the electron mediator may be the first or second droplet and the droplet operation may comprise moving an actuated droplet of fluid medium upon the hydrophobic surface and fusing the actuated droplet with the droplet comprising the electron mediator, wherein the actuated droplet also comprises an electron mediator. Typically, the actuated droplet comprises a high concentration of electron mediator. For example, the actuated droplet may comprise a higher concentration of electron mediator than is present in the droplet comprising the electron mediator, which is optionally the first or second droplet. Alternatively, the droplet operation to increase the concentration of electron mediator in the first or second droplet may be an operation whereby the first or second droplet is moved out of electrical contact with the first or second sensing electrode respectively, and a new droplet comprising fresh electron mediator (usually a higher concentration of the mediator than in the droplet being replaced) is moved into electrical contact with the first or second sensing electrode.

In another embodiment, the sensing system comprises a first droplet, a second droplet and a third droplet. The third and second droplets are each in contact with the first droplet via a droplet interface; each droplet interface comprises a layer of amphipathic molecules; the droplet interface between the first and second droplets comprises a first transmembrane pore; the droplet interface between the first and third droplets comprises a further transmembrane pore which is an ion channel; the third droplet is in electrical contact with the first sensing electrode; and the second droplet is in contact with the second sensing electrode. This embodiment with first, second and third droplets is one which is particularly advantageous for providing a reservoir of electron mediator which can be supplied from the third droplet to either the first or second droplet.

In this embodiment, the second droplet (droplet C in FIG. 18) and the third droplet (droplet A in FIG. 18), typically both comprise electron mediator. The first droplet usually comprises the analyte. The analyte may be DNA or RNA for sequencing, and in particular for sequencing at the interface of the first and second droplets via a nanopore. As discussed above the third droplet is in electrical contact with the first sensing electrode; and the second droplet is in contact with the second sensing electrode (and this may be for the purpose of detecting ionic current changes to sequence the DNA).

Typically, to enable passage of ionic current from the third droplet (droplet A in FIG. 18) to the first droplet (droplet B in FIG. 18), the interface between the third and first droplets usually contains a very high number of the further transmembrane pores which are ion channels. A high number of such further transmembrane pores in the interface between the third and first droplets reduces the electrical resistance at this point in the network, enabling current to flow between the electrodes to enable sensing at the interface between the first and second droplets (droplets B and C in FIG. 18). Typically, therefore, the number of further transmembrane pores at the interface between the first and third droplets is higher than the number of first transmembrane pores at the interface between the first and second droplets. For instance, said number of further transmembrane pores may be at least 10 times said number of first transmembrane pores. Said number of further transmembrane pores may be at least 100 times said number of first transmembrane pores, or for instance at least 1000 times, or at least 10,000 times said number of first transmembrane pores. The number of further transmembrane pores may for example be at least 100,000 times said number of first transmembrane pores.

The passage of the analyte with respect to the nanopore may be controlled such that the analyte does not fully pass from the first to the second droplet. This ensures that the analyte is retained in the first droplet. Alternatively the analyte may be allowed to translocate fully through the nanopore from the first droplet into the second droplet. Such control may be achieved by changing the polarity or amount of the potential difference between the electrodes.

The type and number of further transmembrane pores inserted into the interface between the third droplet (A in FIG. 18) and the first droplet (B in FIG. 18) can be used to control the resistance at this point in the circuit. For example, further transmembrane pores with large diameters (eg. >2 nm) can be used to allow large amounts of current to pass freely. Alternatively, small further transmembrane pores (eg. <2 nm in diameter) can be used to control ionic selectivity, for example to prevent unwanted ionic species passing the membrane. For instance, it is possible to prevent or restrict the flow of the electron mediator (e.g. ferro/icyanide species) from passing through the membrane (for example, where it is not desired to have the electron mediator directly contact one or more analyte species) by using further transmembrane pores that are too narrow to pass the large ions, or further transmembrane pores with negative charges in the central channel to create electrostatic barriers to passage. Often, therefore, the further transmembrane pores have an internal diameter of less than 2 nm. Additionally or alternatively, the further transmembrane pores may comprise a central channel which is charged, for instance negatively charged. The further transmembrane pores may be referred to as "frit" nanopores.

The mediator may be any suitable electron mediator. Typically, the mediator comprises an $Fe^{2+}/Fe^{3+}$ couple; for example, the electron mediator may comprise $Fe^{3+}$. For example, the electron mediator may comprise $[Fe(CN)_6]^{3-/4-}$.

It is possible to control which membranes the nanopores insert into in a multiple interface network, such as the embodiment presently being discussed with first, second and third droplets. This can be achieved, for instance, by controlling the order in which membrane interfaces are formed, by the application of large voltages across desired membrane interfaces, or by which droplets contain the nanopores. For example, it is possible to insert large numbers of the "frit" nanopores in the interface between the first and third droplets in this embodiment (droplets A and B in FIG. 18) by including the nanopores only in the third droplet (droplet A in FIG. 18). Likewise, if the first droplet (droplet B in FIG. 18) contains said first transmembrane pore (e.g. a sensing nanopore, suitable for DNA sequencing) it is possible to insert the first transmembrane pore with control into the interface between the first and second droplets (droplets B and C in FIG. 18). In this way a droplet operation may be performed, in accordance with the method of the invention, to insert said further transmembrane pores into the interface between the first and third droplets. Similarly, a droplet operation may be performed, in accordance with the method of the invention, to insert said first transmembrane pore into the interface between the first and second droplets. Thus, step (c), or at least one of a plurality of steps (c), in the method of the invention, may comprise inserting further transmembrane pores into the interface between the first and third droplets. Similarly, step (c), or at least one of a plurality of steps (c), in the method of the invention, may comprise inserting a first transmembrane pore into the interface between the first and second droplets.

It is possible to sense changes in the concentration of electron mediator across the network of droplets (e.g. the first, second and third droplets of the embodiment discussed above) by monitoring the change in voltage, arising from a change in chemical potential as the mediator is reacted from one species to the other. It is therefore possible to detect that the electron mediator has become depleted during long experiments. For instance, if electron mediator in the third droplet (droplet A in FIG. 18) has become depleted, it is possible to adjust the conditions in the third droplet to refresh the mediator. Thus, for instance, it is possible to connect and fuse a new droplet (a fourth droplet) containing fresh mediator into the third droplet, as shown schematically in FIG. 18 parts TI) and III). Alternatively, the third droplet can be moved away from the first droplet (droplet B in FIG. 18), to un-form the layer of amphipathic molecules at the droplet interface, and a new third droplet containing fresh mediator can be connected to the first droplet. The new third droplet may also contain further transmembrane pores to insert at the new interface between the third and first droplets to enable ionic flow between the third and first droplets.

Thus, the droplet comprising the electron mediator may be the third droplet and the droplet operation may comprise moving an actuated droplet (a fourth droplet) of fluid medium upon the hydrophobic surface and fusing the actuated droplet (fourth droplet) with the third droplet, wherein the actuated droplet also comprises an electron mediator. Typically, the actuated (fourth) droplet comprises a high concentration of electron mediator, e.g. a higher concentration of electron mediator than is present in the third droplet (in which the electron mediator may have depleted or be about to be depleted). Alternatively, the droplet operation to increase the concentration of electron mediator in the third droplet may be an operation whereby the third droplet is moved out of electrical contact with the first sensing electrode, and a new (replacement) third droplet comprising fresh electron mediator (e.g. a higher concentration of mediator than the third droplet) is moved into electrical contact with the first sensing electrode. The new third droplet may also contain further transmembrane pores to insert at the new interface between the third and first droplets to enable ionic flow between the third and first droplets.

Additionally or alternatively, in this embodiment with first, second and third droplets, the droplet comprising the electron mediator may be the second droplet (droplet C in FIG. 18) and the droplet operation may comprise moving an actuated droplet (a fourth droplet) of fluid medium upon the hydrophobic surface and fusing the actuated droplet (fourth droplet) with the second droplet, wherein the actuated droplet also comprises an electron mediator. Typically, the actuated (fourth) droplet comprises a high concentration of electron mediator, e.g. a higher concentration of electron mediator than is present in the second droplet (in which the electron mediator may have depleted or be about to be depleted). Alternatively, the droplet operation to increase the concentration of electron mediator in the second droplet may be an operation whereby the second droplet is moved out of electrical contact with the second sensing electrode, and a new (replacement) second droplet comprising fresh electron mediator (e.g. a higher concentration of mediator than the removed second droplet) is moved into electrical contact with the first sensing electrode. The new second droplet may also contain said first transmembrane pore to insert at the new interface between the second and first droplets.

In another embodiment the mediator might not be included in the second droplet (droplet C in FIG. 18), but rather separated into a fourth droplet (e.g. a droplet D), which is itself connected to the second droplet by a frit-like nanopore interface to create an network A-B-C-D, where the third and fourth droplets (droplets A and D) contain the mediator, the first droplet (droplet B in FIG. 18) contains the analyte, and the first transmembrane pore (which may be a nanopore sensor) is in the interface between the first and second droplets (B and C). In this embodiment, both the third and fourth mediator droplets can be removed and replaced in droplet operations of step (c), for example if sensing in step (a) detects that the mediator is depleted, without affecting the first and second "sensing" droplets (B and C).

Accordingly, in a preferred aspect the invention provides a method of operating a sensing system, wherein the sensing system comprises:
(i) an electrowetting device, which electrowetting device comprises:
an array of actuation electrodes, and
an insulator layer covering the actuation electrodes and having an outermost hydrophobic surface;
a first sensing electrode; and
a second sensing electrode;
(ii) disposed on the hydrophobic surface:
an apolar fluid medium,
first, second, third and fourth droplets each comprising a polar liquid in the fluid medium;
the first, second, third and/or fourth droplet comprises a layer of amphipathic molecules at an interface between said first, second, third and/or fourth droplet and the fluid medium;
the third droplet is in contact with the first droplet via a droplet interface, the first droplet is in contact with the second droplet via another droplet interface, and the second droplet is in contact with the fourth droplet via yet another droplet interface;
each droplet interface comprises a layer of amphipathic molecules;
the droplet interface between the first and second droplets comprises a first transmembrane pore;
the droplet interface between the first and third droplets comprises a plurality of further transmembrane pores which are ion channels;
the droplet interface between the second and fourth droplets also comprises a plurality of further transmembrane pores which are ion channels;
the first droplet comprises an analyte;
the third and fourth droplets comprise an electron mediator;
the third droplet is in electrical contact with the first sensing electrode; and
the fourth droplet is in electrical contact with the second sensing electrode;
(iii) a control system configured to obtain an electrical measurement from the first and second sensing electrodes, and to apply an actuation signal to the array of actuation electrodes;
wherein the method comprises
a) obtaining an electrical measurement from the first and second electrodes, and repeating this step a plurality of times to obtain a plurality of electrical measurements;
b) comparing one or more of the electrical measurements with one or more of the other electrical measurements among the plurality of electrical measurements, determining an alteration in the electrical measurement detected over time that is attributable to a loss of electron mediator in the third or fourth droplet and selecting a droplet operation to increase the concentration of electron mediator in that droplet; and
c) applying an actuation signal to an actuation electrode to effect the droplet operation.

The droplet operation may comprise moving an actuated droplet (a fifth droplet) of fluid medium upon the hydrophobic surface and fusing the actuated droplet (fifth droplet) with the third or fourth droplet, wherein the actuated droplet also comprises an electron mediator. Typically, the actuated (fifth) droplet comprises a high concentration of electron mediator, e.g. a higher concentration of electron mediator than is present in said third or fourth droplet (in which droplet the electron mediator may have depleted or be about to be depleted). Alternatively, the droplet operation to increase the concentration of electron mediator in the third or fourth droplet may be an operation whereby the third or fourth droplet is moved out of electrical contact with the first or second sensing electrode respectively, and a new (replacement) third or fourth droplet comprising fresh electron mediator (e.g. a higher concentration of mediator than the third or fourth droplet being replaced) is moved into electrical contact with the first or second sensing electrode respectively. The new third or fourth droplet may also contain said further transmembrane pores to insert at the new interface between the third and first droplets, or at the new interface between the second and fourth droplets, respectively to enable ionic flow between those droplets.

Exemplary Method 3: Improving Accuracy of Detection

A particular advantage of the present invention is that the sensing system permits a sample to be exposed to a plurality of pores. This can improve the accuracy with which an analyte can be determined, particularly in the case where the analyte is a polymeric analyte such as DNA. Moreover, the pores to which the analyte is exposed may be selected based on the electrical measurements obtained upon interaction of the analyte with a previous transmembrane pore. This provides for a dynamic sensing system capable of selecting and performing the most appropriate sensing operations to provide accurate identification of an analyte.

Thus, in a preferred embodiment the invention provides a method of operating a sensing system according to any preceding claim, wherein the sensing system comprises disposed on the hydrophobic surface of the electrowetting device:
an apolar fluid medium;
a first, second and third droplet comprising a polar liquid medium;
the first and/or the second and/or the third droplet comprise a layer of amphipathic molecules at an interface between said first and/or second and/or third droplet and the fluid medium;
the first droplet being in contact with the second droplet via a droplet interface, said droplet interface comprising a layer of amphipathic molecules and a first transmembrane pore;
the third droplet being in contact with the first or second droplet via another droplet interface, said another droplet interface comprising a layer of amphipathic molecules and a second transmembrane pore; and
the first droplet comprising an analyte.

In some embodiments, the first and second transmembrane pores are the same: this allows the analyte to be analysed twice using the same pore, which is of course useful in improving the accuracy of the measurement. However, in another embodiment the second transmembrane pore differs from the first transmembrane pore, in which embodiment the use of two different pores provides two different information sets concerning the analyte to aid identification.

Usually, in this embodiment, the electrical measurement of step (a) is an electrical measurement indicating an interaction of the analyte with the first and/or the second transmembrane pore. The relative configurations of the first and second sensing electrodes and the three droplets determines which interactions can be detected in the initial configuration.

Where the first and second sensing electrodes are each in contact with one of a pair of droplets that are directly in contact with one another via a droplet interface, the electrical measurement may comprise a measurement indicating that the analyte has interacted with a transmembrane pore present in that interface. For example, the first sensing electrode may be in electrical contact with the first droplet and the second sensing electrode in electrical contact with the second droplet, and the first and second droplets may be in contact via a droplet interface comprising the first transmembrane pore as shown in FIG. 8. In that case, the electrical measurement may be a measurement indicating the interaction with the first transmembrane pore. In another embodiment, the first sensing electrode may be in electrical contact with the first droplet and the second sensing electrode in electrical contact with the third droplet, and the first and third droplets may be in contact via a droplet interface comprising the second transmembrane pore. In that case, the electrical measurement may be a measurement indicating the interaction with the second transmembrane pore.

Thus, in one embodiment, step (b) comprises determining that the analyte has interacted with the first transmembrane pore. In another embodiment, step (b) comprises determining that the analyte has interacted with the second transmembrane pore.

Having determined by electrical measurement that the analyte has interacted with the first or second transmembrane pore in this way, step (b) may further comprise selecting a droplet operation which brings the droplet comprising an analyte into contact with a further droplet and a further interface comprising a further transmembrane pore. In this manner an analyte may be moved from one droplet, to a second droplet, to a further droplet and so on, passing through a transmembrane pore each time, providing a large data set form which the identity of the analyte may be determined.

The droplets and electrodes may alternatively be arranged as shown for instance in FIG. 9, where the first and second sensing electrodes are separated by two transmembrane pores. That is, the first sensing electrode is in electrical contact with the third droplet and the second sensing electrode is in electrical contact with the second droplet. The interface between the first and second droplets comprises the first transmembrane pore and the interface between the first and third droplets comprises the second transmembrane pore.

In this arrangement, the analyte present in the first droplet may interact with either the first or second transmembrane pore, or both. Alternatively, the analyte may be present initially in the second droplet and may move through the first transmembrane pore into the first droplet and then through the second transmembrane pore to the third droplet. Such movement of the analyte can be controlled by potentials applied to the first and second sensing electrodes, where the analyte is charged. Accordingly, in this configuration the electrical measurement taken in step (a) may be an electrical measurement indicating an interaction with either or both of the first and second transmembrane pores.

Thus, in one aspect step (b) may comprise determining that the analyte has interacted with the first and second transmembrane pores simultaneously.

Of course, a plurality of further droplets may be present, each contacting the first, second or third droplet via a droplet interface, which droplet interface contains a further transmembrane pore. The analyte may interact with each of these, simultaneously or in turn, which interactions may be detected by the first and second sensing electrodes or further sensing electrodes.

In a particular aspect of this embodiment, because the droplet volumes may be very small, where the analyte is a sufficiently long polymer chain, it may reach across the droplet's interior and interact with both the first and second pores simultaneously. The interaction of an analyte with two pores simultaneously provides even more detailed information on the structure of the analyte. Thus, in one aspect step (b) may comprise determining that a single strand of polymeric analyte has interacted with the first and second transmembrane pores simultaneously. In a preferred aspect of this embodiment, the analyte is a single strand of DNA. For instance, the first droplet may contains a single strand of DNA: the method is capable of interrogating a single analyte particle.

Once it has been determined that the analyte has interacted with the first and second transmembrane pores, it is typically desirable to reconfigure the droplet system in order to be able to take electrical measurements indicating the interaction of the analyte with one or more further transmembrane pores. For instance, further droplets may be brought into contact with the droplet system to provide further interfaces comprising a further transmembrane pore. This can be achieved by actuating the droplet containing the analyte (typically the first droplet) and/or other droplets within the sensing system. The reconfiguration by droplet operations is typically permitted once it is determined, from the electrical measurement(s) taken in step (a), that the analyte has fully interacted with (for instance passed through) all of the transmembrane pores of interest in the initial droplet system.

In one embodiment, the droplet operation selected in step (b) and performed in step (c) comprises moving one or more of the first droplet, the second droplet and the third droplet in order to separate the first droplet from the second droplet and/or the third droplet.

In one embodiment, the droplet operation selected in step (b) and performed in step (c) comprises bringing the first droplet into contact with a further droplet, such that the further droplet contacts the first droplet via a droplet interface comprising a layer of amphipathic molecules and a further transmembrane protein.

The accuracy that can be achieved by the exposure of a sample to a plurality of different pores as described above is very high.

Other Exemplary Methods

In some embodiments of the method of the invention, step (a) comprises contacting the first transmembrane pore with an analyte such that the analyte moves with respect to the pore, and obtaining one or more electrical measurements as the analyte moves with respect to the pore; and the method further comprises determining the presence, absence, or one or more characteristics of the analyte.

In a preferred aspect of this method, step (b) comprises determining the presence or absence of one or more characteristics of the analyte, and optionally wherein step (b) further comprises determining whether to keep or dispose of the first droplet based on the presence, or absence, or one or more characteristics of the analyte.

Typically, in such methods, the analyte is a polynucleotide. Also typically in such methods, the said characteristics may be one or more of (i) the length of the polynucleotide, (ii) the identity of the polynucleotide, (iii) the sequence of the polynucleotide, (iv) the secondary structure of the polynucleotide, and (v) whether or not the polynucleotide is modified.

In the following methods, the first droplet initially comprises an analyte, preferably a polynucleotide. Preferably the analyte is charged. The first and second droplets are in electrical contact with the first and second sensing electrodes respectively. Preferably, in these methods, the first and second droplets are droplets of aqueous polar medium immersed in an apolar oil medium, each with a layer of amphipathic molecules disposed at an interface between the aqueous medium and the oil medium. Where a further or new droplet is involved in the method, the further or new droplet is typically also a droplet of aqueous medium and comprises a layer of amphipathic molecules disposed at an interface between the aqueous medium and the oil medium.

In one embodiment, the method is a method of sequencing a polymeric analyte (for instance wherein the analyte comprises DNA or RNA) in real time.

In one embodiment, referred to hereafter as the analyte selection embodiment, the method may comprise:
 a) detecting an interaction between the analyte and the first transmembrane pore by obtaining an electrical measurement;
 b) determining the presence or absence or one or more characteristics of the analyte based on the electrical measurement obtained in (a), deciding to keep that analyte, and selecting a droplet operation to bring a further droplet of polar aqueous medium into contact with the second droplet according to one or more instructions stored in the control system; and
 translocating the analyte into the second droplet by applying a potential to the first and second sending electrodes; and
 c) applying an actuation signal to the array of actuation electrodes in order to bring the further droplet into contact with the second droplet. The further droplet may comprise a layer of amphipathic molecules disposed at an interface between the further droplet and the oil medium. Step (c) may further comprise forming a droplet interface comprising a membrane between the second droplet and the further droplet, optionally wherein that membrane comprises a second transmembrane pore.

In another embodiment, the method may comprise:
 ai) detecting an interaction between the analyte and the first transmembrane pore by obtaining an electrical measurement;
 aii) determining the presence or absence or one or more characteristics of the analyte based on the electrical measurement obtained in (a), deciding to reject the analyte, and applying a potential to the first and second sending electrodes to prevent that analyte translocating into the second droplet;
 aiii) optionally repeating steps (ai) and (aii) one or more times; and
 performing steps a-c of the analyte selection method above.

In another embodiment, the method may comprise sifting a target analyte from a first droplet, and then detecting the analyte in one or more further pores (for example to enable the sequence of the analyte to be detected where the analyte is a polynucleotide). In such embodiments, the method may comprise:
 a) obtaining an electrical measurement indicating that the target analyte is passing or has passed from the first to the second droplet via the first transmembrane pore;
 b) analysing the electrical measurement; optionally determining that the analyte is passing or has passed from the first to the second droplet; and selecting a droplet operation to separate the first and second droplets;
 c) applying an actuation signal to the array of actuation electrodes in order to move the first and/or second droplets such that the first and second droplets no longer contact one another.

In this embodiment, the droplet operation selected in step (b) and performed in step (c) may further comprise bringing the droplet into contact with a further droplet. The further droplet is typically in contact with, or is placed in contact with, a further sensing electrode. The interface thus formed between the second and further droplets typically comprises a membrane and a second transmembrane pore.

In this embodiment, steps (a) to (c) may then be repeated one or more times. For instance, the method may further comprise:
 a) obtaining an electrical measurement indicating that the target analyte is passing or has passed from the second to the further droplet via the second transmembrane pore;
 b) analysing the electrical measurement; optionally determining that the analyte is passing or has passed from the second to the further droplet; and selecting a droplet operation to separate the second and further droplets;
 c) applying an actuation signal to the array of actuation electrodes in order to move the second and/or further droplets such that the second and further droplets no longer contact one another.

The droplet operation selected in step (b) and performed in step (c) may further comprise bringing the droplet into contact with another further droplet. The another further droplet is typically in contact with, or is placed in contact with, another further sensing electrode. The interface thus formed between the further droplet and another further droplet typically comprises a membrane and a third transmembrane pore.

The method may be repeated one or more times.

In an aspect of this method, step (b) comprises selecting a second droplet operation, in order to bring a new droplet into contact with the first droplet. For example, step (b) may in addition comprise selecting a droplet operation in order to bring a new droplet into contact with the first droplet. When this droplet operation is performed in step (c), the interface between the new droplet and the first droplet may comprise a new transmembrane pore. This can be achieved for instance by providing a transmembrane pore suitable for insertion in either the first droplet or the new droplet. The new transmembrane pore may allow a different target analyte to pass into the new droplet. Thus, step (a) may be repeated a plurality of times wherein, in each iteration, an electrical measurement is taken which indicates the passing of a new target analyte into the new droplet. That is, the method may additionally comprise:
 a) obtaining an electrical measurement indicating that the new target analyte is passing or has passed from the first to the new droplet via the new transmembrane pore;
 b) analysing the electrical measurement; optionally determining that the new target analyte is passing or has passed from the first to the new droplet; and selecting a droplet operation to separate the first and new droplets;
 c) applying an actuation signal to the array of actuation electrodes in order to move the first and/or new droplets such that the first and new droplets no longer contact one another.

This method may be repeated a plurality of times to collect different target analytes in different droplets.

By this method, it is easily possible to create complex networks with many different droplet configurations to control where target analytes go. It is also possible in any of the new droplets to employ different conditions (eg. different droplets can have different pH, salts, buffers, co-factors, enzymes, temperature, etc) or differences at the interfaces (eg. different types of pores, numbers of pores, orientation of pores, direction of analyte translocation, different applied voltage, etc). In this way it is possible to perform multiple different actions on the same target analyte. For example, the target analyte may be sequenced under different conditions. In other embodiments, the target analyte may be moved to be subjected to common nucleic preparations such as polymerase amplification, reverse transcription, restriction enzyme cuts, ligation of components, nuclease degradation, cas9 binding or cutting, etc.

By this method, it is also possible to sift a desired target analyte from an analyte which contains a mixture of species. In one embodiment, the method comprises sifting one or more desired DNA sequences from a mixture of DNA sequences.

In some preferred embodiments, the droplet operation selected in step (b) and performed in step (c) may comprise fusing two droplets together. In such cases, the droplets may fuse upon contact or may require the application of a voltage in order to disrupt any membrane between the two droplets. Thus, in some embodiments, the first sensing electrode is in electrical contact with the first droplet (or where present optionally the third droplet) and the second droplet is in electrical contact with the second sensing electrode, and the method of the invention comprises:
  a) obtaining an electrical measurement between the first and second sensing electrodes;
  b) analysing the electrical measurement and selecting a droplet operation according to one or more instructions stored in the control system, wherein the droplet operation comprises fusing a further droplet with the second droplet;
  c) applying an actuation signal to the actuation electrodes in order to move the further droplet into contact with the second droplet and a further sensing electrode; and applying a potential across the second sensing electrode and the further sensing electrode in order to fuse the second and further droplets.

This may be used to adjust the conditions in the second droplet. For instance, the further droplet may comprise material which can be used to adjust the pH, ion concentration or other properties of the droplet. Alternatively, the further droplet may comprise material allowing an analyte present in the second droplet to be processed, such as the appropriate enzymes and co-factor reagents necessary to amplify a polynucleotide analyte such as DNA by PCR.

Thus, in some embodiments, the process comprises:
  a) obtaining an electrical measurement between the first and second sensing electrodes indicating that the a desired polynucleotide sequence (eg. a gene of interest) has translocated from the first droplet to the second droplet;
  b) analysing the electrical measurement and optionally determining that the translocation of the desired polynucleotide sequence from the first to the second droplet has occurred, and selecting a droplet operation according to one or more instructions stored in the control system, wherein the droplet operation comprises fusing a further droplet with the second droplet;
  c) applying an actuation signal to the actuation electrodes in order to move the further droplet into contact with the second droplet and a further sensing electrode; and applying a potential across the second sensing electrode and the further sensing electrode in order to fuse the second and further droplets, wherein the further droplet contains raw materials for a PCR procedure (such as enzymes and co-factor reagents).

A frequently desirable result of a droplet operation which places one droplet in contact with another is to transfer material between the droplets. This can be achieved by osmosis, where two droplets of different osmotic potential. When droplets containing different osmotic potentials (eg. droplets having different concentrations of salts or other suitable solutes) are connected to form a droplet interface comprising a membrane (for example a bilayer of amphipathic molecules), water will flow across the membrane between the two droplets to balance the osmotic potential: water will flow from a low salt concentration droplet to a droplet with a higher concentration salt solution, until either the osmotic potential is balanced or the droplets are disconnected. By connecting the appropriate osmotic potential droplet to a target droplet, it is possible to either increase the water content in a target droplet (eg. by connecting a droplet having a lower ion concentration than the target droplet—that is, a less salty droplet) or decrease the water content in a target droplet (eg. by connecting a droplet having a higher ion concentration than the target droplet—that is, more salty solution droplet). In this way it is possible to dilute or concentrate the contents in the target droplet.

The "target droplet" is the droplet into which a further droplet is brought into contact here.

Accordingly, in some embodiments of the method:
  step (b) optionally comprises determining the ion concentration or osmotic potential of one or more of the first, second and where present third droplets (target droplet), and selecting a droplet operation to bring a further droplet having a different ion concentration or osmotic potential into contact with the said the first, second or third droplet (target droplet); and
  step (c) comprising applying an actuation signal to the actuation electrode array to bring said further droplet into contact with said first, second or third droplet (target droplet), to form a droplet interface between the further droplet and the said first, second or third droplet (target droplet); and
  the method further comprises allowing water to pass across the droplet interface between the first, second or third droplet (target droplet) and the further droplet.

In some embodiments, the further droplet is selected from among a plurality of droplets each having different osmotic potentials or ion concentrations.

Control of the salt content of a droplet may be desirable for instance where it is intended to inhibit an enzymatic reaction, such as ligation of an adapter to target DNA molecules, through the use of high salt concentration, then initiate the enzymatic reaction when desired by dilution of the salt. In some embodiments, therefore, it may be useful to dilute a droplet. In other embodiments, however, it may be desired to concentrate the contents of a droplet by removing water. For instance, concentrating a sample can be useful in increasing the sensitivity of detection of the target molecules, either by sensing an analyte by its interaction with a nanopore, or for fluorescence measurements of an analyte.

Thus, in some embodiments of this method, the further droplet has a higher osmotic potential or ion concentration than the target droplet, which enables concentration of the target droplet. In other embodiments, of this method, the further droplet has a lower osmotic potential or ion concentration than the target droplet, which enables dilution of the target droplet.

In some embodiments, the further droplet may be selected from a plurality of droplets each having a different osmotic potential or ion concentration.

Accordingly, in a particularly preferred example, the method comprises:

passing an analyte from the first droplet to the second droplet as described herein;

a) obtaining an electrical measurement from the first and second sensing electrodes (which are in electrical contact with the first and second droplets respectively);

b) analysing the electrical measurement to determine the osmotic potential or ion concentration present in the second droplet, and selecting according to one or more instructions stored in the control system a droplet operation whereby a further droplet having a different osmotic potential or ion concentration to the second droplet may be brought into contact with the second droplet; and applying an actuation signal to the actuation electrodes to bring the further droplet into contact with the second droplet, preferably by moving the further droplet. The further droplet and the second droplet are thus connected by a droplet interface comprising a layer of amphipathic molecules.

The method may further comprise allowing water to flow in or out of the second droplet.

Additional Process Steps

The method of the invention is typically repeated one or more times. That is, once step (c) has been performed and a newly-arranged system of droplets prepared, steps (a) to (c) may be repeated. The measurement taken in step (a), the droplet operation selected in step (b) and performed in step (c) may differ upon each iteration of the method.

Moreover, the method of the invention may comprise one or more further process steps to be performed before, between or after steps (a), (b) and (c).

One such additional step is the initial preparation of a sample. It is particularly desirable to provide a "raw" sample to the sensing system, without requiring any preparation of the sample on the part of the user. By a "raw" sample is meant a sample as it is initially collected: for instance a blood sample as collected from the body or a sample of seawater as directly collected from the sea. Preferably, the sensing system itself performs the initial process steps needed to prepare the sample to be subjected to the method of the invention. Such initial preparation steps may include washing of the sample, purification, cell lysis, dilution, concentration, modification by binding additional groups and so on.

Thus, in some embodiments the process comprises an initial step of providing a raw sample to the sensing system. Preferably, the initial step further comprises preparing the sample within the sensing system. By "preparing" is meant performing any operations on the sample needed to place it in a form suitable for use in the method of the invention.

As explained above, the method of the invention permits the recovery of one or more droplets comprising analyte. In a preferred, aspect, the method of the invention further comprises recovering the analyte itself. That is, some or preferably all of the droplet(s) comprising the analyte may be collected together and removed from the sensing system. The droplets may then be processed to remove contaminants and return the analyte.

Another advantage of the invention is that it may be performed simultaneously on a plurality of droplet systems within the same sensing system. A droplet system comprises the first and second droplets as defined herein, and optionally a third and further droplets. Thus, in a preferred aspect of the method, the sensing system comprises:

disposed on the hydrophobic surface, the fluid medium and a first droplet system comprising the first droplet and the second droplet as defined herein; and also disposed on the hydrophobic surface, a second droplet system comprising another first droplet and another second droplet as defined herein;

and the method comprises performing steps (a), (b) and (c) simultaneously on the first droplet system and on the second droplet system. In theory, the method may be performed simultaneously on a large number of droplet systems, for example on at least ten or at least a hundred droplet systems simultaneously. In each iteration of the method, the steps (a), (b) and (c) may be the same or different. For example, one or more of steps (a), (b) and (c) performed on the first droplet system may differ from one or more of steps (a), (b) and (c) performed on the second droplet system. Alternatively, steps (a), (b) and (c) performed on the first and second droplet systems may be the same. However, where the first and second droplet systems are present in the same device, the droplet operation performed in step (c) cannot comprise moving a droplet to exactly the same location unless those droplets are intended to fuse together.

Apparatus of the Invention

The invention provides a sensing system as described herein, capable of performing the method of the invention. The invention therefore provides a sensing system comprising:

an electrowetting device, which electrowetting device comprises:

an array of actuation electrodes;

an insulator layer covering the actuation electrodes and having an outermost hydrophobic surface;

a first sensing electrode; and a second sensing electrode;

and a control system configured to:

obtain an electrical measurement from the first and second sensing electrodes;

analyse the electrical measurement and then select a droplet operation based on the electrical measurement according to one or more instructions stored in the control system; and apply an actuation signal to an actuation electrode to effect the droplet operation.

The features of the sensing system are as defined herein.

In a preferred embodiment, the sensing system comprises:

a first substrate supporting the array of activation electrodes; and a second substrate facing the hydrophobic surface of the insulator layer and supporting the first and second sensing electrodes.

In the sensing system of the invention, the control system is typically configured to perform the method according to any embodiment described herein.

The sensing system need not comprise a fluid medium or any droplets of liquid medium. Rather, the sensing system may be configured to receive a fluid medium and a first droplet and a second droplet each comprising liquid in the fluid medium, one of the liquid and the fluid medium being polar, and the other of the liquid and the fluid medium being apolar. However, when the sensing system is in use, the sensing system will comprise such of liquid and fluid media. Accordingly, in one aspect the invention provides a sensing system as described above, comprising, disposed on the hydrophobic surface, a fluid medium and a first droplet and a second droplet each comprising liquid in the fluid medium, one of the liquid and the fluid medium being polar, and the other of the liquid and the fluid medium being apolar;

the first and/or the second droplet comprising a layer of amphipathic molecules at an interface between said first and/or second droplet and the fluid medium;

the first droplet being in contact with the second droplet via a droplet interface; and the droplet interface comprising a layer of amphipathic molecules and a first transmembrane pore.

The first droplet, the second droplet and if present the third droplet are as defined herein.

The invention further provides the use of a sensing system as described above to perform a method according to any embodiment described herein.

Second Aspect of the Invention

In another aspect, the invention provides method of operating a sensing system, wherein the sensing system comprises:
(i) an electrowetting device, which electrowetting device comprises:
an array of actuation electrodes;
an insulator layer covering the actuation electrodes and having an outermost hydrophobic surface;
a first sensing electrode; and
a second sensing electrode, all as described herein;
(ii) disposed on the hydrophobic surface,
a fluid medium, and a first droplet, a second droplet and a third droplet each comprising liquid medium in the fluid medium, one of the liquid and the fluid medium being polar, and the other of the liquid and the fluid medium being apolar;
wherein the first droplet is in contact with the second droplet via a droplet interface, and the first droplet is in contact with the third droplet via a droplet interface;
wherein each droplet interface comprises a layer of amphipathic molecules and a transmembrane pore;
wherein optionally, one or more of the first, second and third droplets comprises a layer of amphipathic molecules at an interface between the droplet itself and the fluid medium; and
(iii) a control system configured to obtain an electrical measurement from the first and second sensing electrodes, and optionally to apply an actuation signal to the array of actuation electrodes;
wherein the method comprises
a) obtaining an electrical measurement from the first and second sensing electrodes; and
b) analysing the electrical measurement obtained in (a) and selecting an operation to perform in relation to the interface between the first and the third droplets.

The electrical measurement obtained in (ai) relates to the transmembrane pore present at the interface between the first and second droplets. The electrical measurement obtained in (ai) is generally an electrical measurement and usually relates to the detection of an interaction between a species such as an analyte present in the first or second droplet, and said transmembrane pore.

The operation selected in (aii) may be for example an electrical measurement to be taken in relation to the transmembrane pore present in the interface between the first and third droplets. That electrical measurement may be as described herein. Alternatively, the operation selected in (aii) may be a decision to translocate a species such as an analyte into contact with a transmembrane pore present in the interface between the first and third droplets.

This method may further comprise subsequently performing a method as described elsewhere herein, comprising steps (a), (b) and (c).

Droplet Constructs of the Invention

The sensing system of the invention may be used to prepare and optionally to manipulate a variety of novel droplet constructs, which are also a part of the invention. These droplet constructs are described below. By a "droplet construct" is meant a collection of droplets of liquid medium disposed in a fluid medium, wherein one of the liquid medium and the fluid medium is polar and the other is apolar. Preferably the liquid medium is polar. The liquid medium and the fluid medium are as described herein. The liquid medium present in each droplet may be the same or different.

A first novel droplet construct according to the invention comprises a first, second and third droplets each comprising liquid medium, wherein:
the first droplet comprises an analyte;
the second and third droplets each comprise an electron mediator; and
the first droplet contacts each of the second and third droplets via a droplet interface, wherein each droplet interface comprises a layer of amphipathic molecules.

In the first novel droplet construct, the droplet interface between the first droplet and the second droplet, and/or the droplet interface between the first droplet and the third droplet may comprise a plurality of ion channels. Preferably, droplet interface between the first droplet and the third droplet comprises a plurality of ion channels, for example at least ten ion channels. Usually, the number of ion channels present in the droplet interface between the first droplet is at least 10 times, or at least 100 times, or at least 1000 times or at least 10,000 times, or at least 100,000 times larger than the number of transmembrane pores present in the droplet interface between the first and the second droplets. The first, second and third droplet may each independently comprise a layer of amphipathic molecules disposed at an interface between the said droplet and a fluid medium.

A second novel droplet construct according to the invention comprises a first, second and third droplets each comprising liquid medium, wherein:
the first droplet contacts the second droplet via a droplet interface, which droplet interface comprises a layer of amphipathic molecules;
the first droplet contacts the third droplet via a droplet interface, which droplet interface comprises a layer of amphipathic molecules; and
the droplet interface between the first droplet and the second droplet, and/or the droplet interface between the first droplet and the third droplet comprises a plurality of ion channels.

In the second novel droplet construct, the first droplet typically comprises an analyte.

In the second novel droplet construct, the second droplet and/or the third droplet typically comprise an electron mediator.

In the first and second novel droplet constructs, the droplet interface between the first droplet and the second droplet typically comprises a first transmembrane pore. Further, the droplet interface between the first droplet and the third droplet may comprise a second transmembrane pore, optionally wherein the second transmembrane pore differs from the first transmembrane pore.

A third novel droplet construct according to the invention comprises a first, second and third droplets each comprising liquid medium, wherein:

the first droplet contacts the second droplet via a droplet interface, which droplet interface comprises a layer of amphipathic molecules and a first transmembrane pore;

the first droplet contacts the third droplet via a droplet interface, which droplet interface comprises a layer of amphipathic molecules and a second transmembrane pore; and the first transmembrane pore and the second transmembrane pore are different.

In the third novel droplet construct, the droplet interface between the first droplet and the second droplet, and/or the droplet interface between the first droplet and the third droplet may comprise a plurality of ion channels. Usually, the droplet interface comprising a plurality of ion channels comprises a high number (e.g. at least 10 or at least 100) ion channels. The droplet interface comprising a plurality of ion channels often contains a high number of ion channels compared to the number of transmembrane pores present in the other droplet interface, for example the number of ion channels may be at least 10 times, or at least 100 times, or at least 1000 times or at least 10,000 times, or at least 100,000 times larger than the number of transmembrane pores present in the other droplet interface.

The third novel droplet construct may optionally further comprise a DNA strand. In this embodiment, the DNA strand may contact the first transmembrane pore and the second transmembrane pore. For instance, the DNA strand may be at least partially within both the first and second transmembrane pores.

In the first, second or third novel droplet constructs of the invention, the second and third droplet may or may not contact one another; preferably, the second and third droplet are not in contact with one another.

In the first, second or third novel droplet constructs of the invention, preferably the liquid medium is a polar medium, preferably an aqueous medium.

In one embodiment, the first, second or third novel droplet construct of the invention is disposed in an apolar fluid medium.

The above droplet constructs in combination with an EWOD device as defined herein are further part of the invention.

Also part of the invention are the above droplet constructs in combination with a sensing system as defined herein, comprising an EWOD device as defined herein and a control system as defined herein.

The invention therefore provides a first, second or third novel droplet construct as defined above where the first or third droplet is in electrical contact with a first electrode, preferably wherein the said novel droplet construct is disposed on a hydrophobic surface of an EWOD device as described herein.

The invention also provides a first, second or third novel droplet construct as defined above wherein the second droplet is in electrical contact with a second electrode, preferably wherein the said novel droplet construct is disposed on a hydrophobic surface of an EWOD device as described herein.

The above-described novel droplet constructs may of course comprise one or more further droplets of liquid medium. Thus, the invention provides a first, second or third novel droplet construct as defined above comprising a further droplet, wherein the first droplet contacts the further droplet via a further droplet interface, which droplet interface comprises a layer of amphipathic molecules. In a preferred aspect of this embodiment, the further droplet interface comprises a further transmembrane pore.

In the above novel droplet constructs, the or each droplet interface may comprise a bilayer of amphipathic molecules.

EXAMPLES

Methods of using the apparatus of the invention are described hereafter.

Example 1: Re-Reading a Sequence

Figure 14:
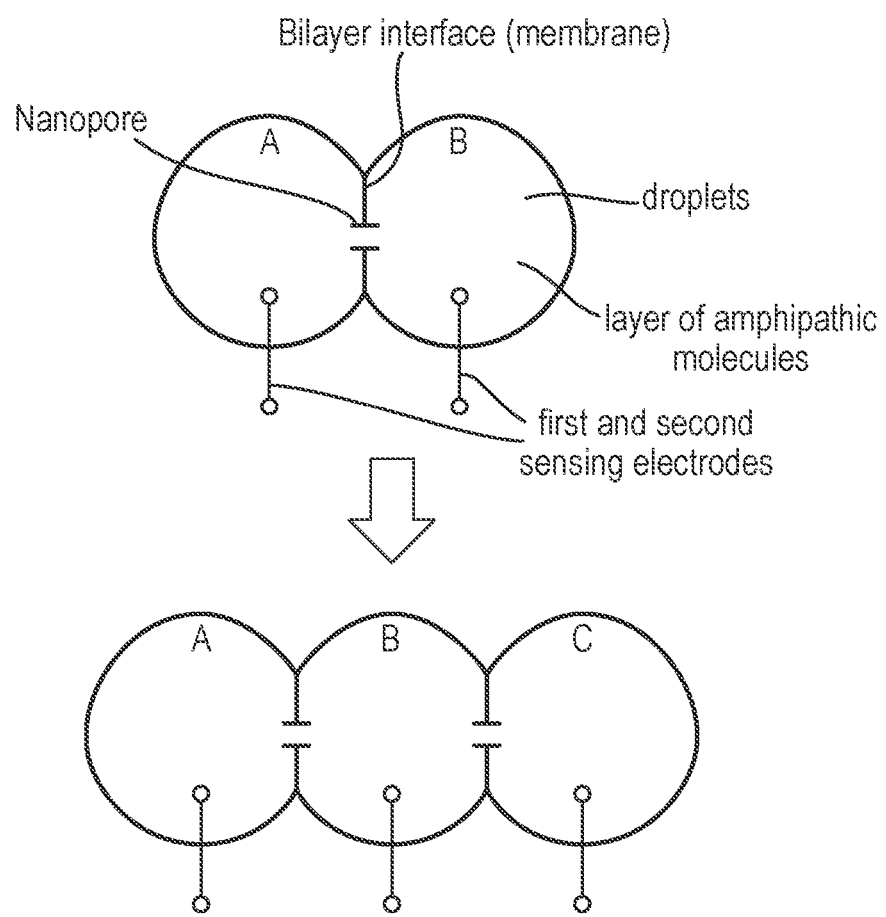
FIG. 14 is a diagram of a typical initial droplet arrangement comprising a first and second droplets, each in contact with a sensing electrode and separated by a droplet interface comprising a layer of amphipathic molecules and a transmembrane pore.

In one example, a first droplet and a second droplet of aqueous polar medium immersed in an apolar oil medium, each with a coating of amphiphilic molecules, are connected so that a droplet interface comprising a layer of amphipathic molecules forms between the two. This arrangement is shown in FIG. 14: the first and second are labelled as "A" and "B" respectively. A transmembrane protein (for example a nanopore) is inserted into the bilayer between the droplets. In one exemplary aspect, the droplet interface comprises a bilayer of amphipathic molecules; in other aspects of this example, the membrane that forms at the comprises a layer of block copolymers. Initially, an analyte is provided in the first droplet (droplet A in FIG. 14).

The first and second droplets (droplets A and B) are brought into electrical contact with a first and second sensing electrodes. The electrical contact between the first and second sensing electrodes shown in Figure is indicated by the projection of the first and second sensing electrodes into the droplet. However, direct contact between the first and second sensing electrodes and the droplets is not required: in practice the electrodes may be separated from the electrodes by an insulating layer. The sensing electrode in electrical contact with each of the first and second electrodes enables the sensing of ionic current changes across the droplet interface. In this way analytes added to droplet A can be sensed by a transmembrane protein (also referred to as a nanopore) in the membrane at the droplet interface connecting droplets A and B. For example, the analyte can be DNA, which is sequenced as it translocates from droplet A to droplet B through a nanopore under the force of an applied voltage potential set by the connected sensing electrodes.

In the following examples, analytes, such as DNA or RNA polynucleotides, can be monitored in real-time as they are sensed by a nanopore in a membrane droplet interface as follows.

In a first example 1A, an interaction between the analyte present in the first droplet (droplet A) and a transmembrane pore present in the droplet interface between the first and second droplets (A and B) is detected in step (a). Step (b) comprises accepting that analyte, and hence selecting a droplet operation which allows the analyte to be placed in contact with a further pore. Thus, the analyte is allowed to pass from the first droplet (A) to the second droplet (B). As is illustrated in FIG. 14, the droplet operation performed in step (c) is the step of bringing a third droplet of polar medium (droplet C) into contact with the existing A & B droplet pair, to form a new droplet interface between droplet B and droplet C. Droplet C may or may not comprise a layer of amphipathic molecules at an interface between droplet C and the surrounding apolar fluid medium. A nanopore is inserted into this new droplet interface, which can be achieved by having soluble nanopores in either droplet B or droplet C (depending on the desired final orientation of the nanopore in the membrane at the droplet interface). The transmembrane pore is caused to insert into the membrane with the application of high voltage (for example as described in WO 2018/096348, the entire contents of which is incorporated herein by reference).

The method of the invention is then repeated at the next droplet interface. Droplet C is located in contact with a further sensing electrode to enable the following. The accepted analyte (eg. a specific gene sequence) that were initially detected at the interface between the first and second droplets (and which have now translocated into droplet B) interact with the nanopore present at the interface between the second and third droplets. Step (a) is therefore repeated: an interaction between the analyte and the nanopore at this new interface is detected by the application of the appropriate voltage potential across the interface between the second and third droplets. The nanopore present at the interface between the second and third droplets is the same or different to that between the first and second droplets. In some cases, a different voltage is used at the second droplet interface (between the second and third droplets) compared to the first droplet interface (between the first and second droplets). In this method, therefore, a desired gene sequence is isolated initially into the second droplet, B, which is then read at a different interface.

In another example 1B, an interaction between the analyte present in the first droplet (droplet A) and a transmembrane pore present in the droplet interface between the first and second droplets (A and B) is detected in step (a). The electrical measurement is analysed by the control system and is rejected. Accordingly, step (a) is repeated until the analysis of the electrical measurement indicates that a desired analyte is present. A voltage is applied to the sensing electrodes to ensure that the analyte does not pass from droplet A to droplet B but is retained in droplet A (typically, to enable this, the analyte is charged). Step (a) is then repeated until the electrical measurement indicates that the analyte is a desired analyte; then, steps (b) and (c) as described in Example 1A are performed.

Example 2—Collection and Processing of Target Analyte

As explained above, in step (c) of the method it is possibly to form or unform droplet interfaces comprising a membrane. This may be done in response to the detection of a target analyte, as will be described below in relation to FIG. 15.

Figure 15:
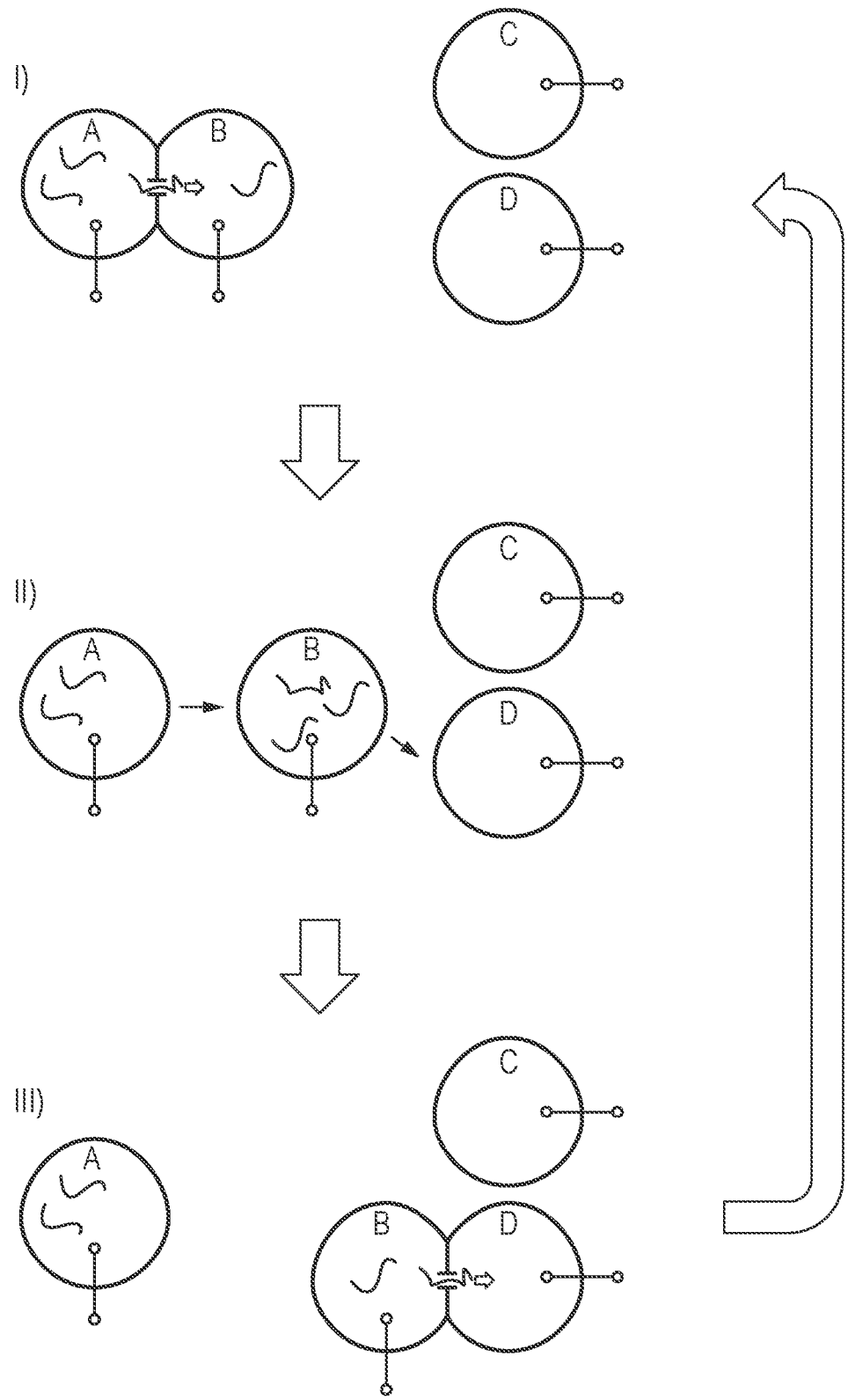
FIG. 15 is a diagram of a method of the invention wherein, in response to an electrical measurement, the second droplet is separated from the first droplet and moved into contact with a new droplet, forming a new droplet interface.

In a first example, illustrated in FIG. 15, an initial droplet setup is shown in 15(I). The first droplet (comprising an analyte) is in contact with a second droplet, and the first and second droplets are in electrical contact with a first and second sensing electrodes respectively (electrodes shown as lines ending in circles). The analyte present in the first droplet passes from the first to the second droplet via the first transmembrane pore, present at the interface between the first and second electrodes. The sensing system comprises at least two further droplets (shown as C and D), each in contact with a sensing electrode.

In the example, in step (a) an electrical measurement is performed and it is thus determined in step (b) that the target analyte has passed into droplet B (the second droplet). A droplet operation is selected to bring the second droplet, B, into a suitable further droplet: D. In step (c), this droplet operation is effected by the actuation electrodes (not shown), as illustrated by the arrows in image 15(II). As a result, the setup shown in 15(III) is formed, where an interface is formed between the second droplet B and further droplet D, the interface comprising a droplet interface through which the target analyte can pass.

In this example, the target analyte is a DNA sequence. In this example, the membrane between each of droplets A and B, and B and D, is a bilayer.

This process of detection followed by forming and unforming of bilayers can be repeated as required, controlling which droplets are connected to each other, and controlling the direction of strands using realtime read-until software that manages the applied voltage across droplet membranes to control which strands pass into a given droplet, and which ones remain in a previous droplet.

In a particular example of this method, example 2A, the method is a method in which target gene panels are filtered and collected from a complex genome or a mixture of genomes. In Example 2A, Droplet A contains a mixture of sequences, from which it is desired to collect N different panels, each panel containing X different target sequence regions (eg. genes). Using real-time sequencing of the molecules as they translocate from droplet A to droplet B, as shown in FIG. 15(I), the desired targets are passed to the second droplet, B, while unwanted strands are rejected. The passing or rejection of individual strands is achieved by repeating step (a) several times: each time a desired target sequence is detected, a voltage is applied to the first and second sensing electrodes to translocate the sequence into the second droplet (B). However, each time an undesired sequence is detected, a voltage is applied to the first and second sensing electrodes to prevent passage of the sequence into the second droplet. In this way, by repetition of step (a), the first desired target panel is collected in droplet B, the second droplet. The droplet interface between the first and second droplets, A and B, is then unformed by a droplet operation and droplet B is moved to another location for further processing.

In addition, a new droplet is connected to droplet A by a droplet operation (not shown) to form a new droplet interface comprising a membrane and a new transmembrane pore. This new transmembrane pore is used to collect a different target analyte, as described in relation to the collection of the first target analyte—the new target analyte is the next panel in the set.

Connection of a new droplet to droplet A, providing a new transmembrane pore to sift out a target analyte, followed by unforming the droplet interface to move the sifted target analyte away from droplet (a) is therefore used to create a multitude of output droplets each with different desired panels. In some embodiments of the method, the first droplet (a) contains a genomic mixture and the method recovers only the segments of interest for further processing.

Example 3—Fusion of Droplets

Figure 16:
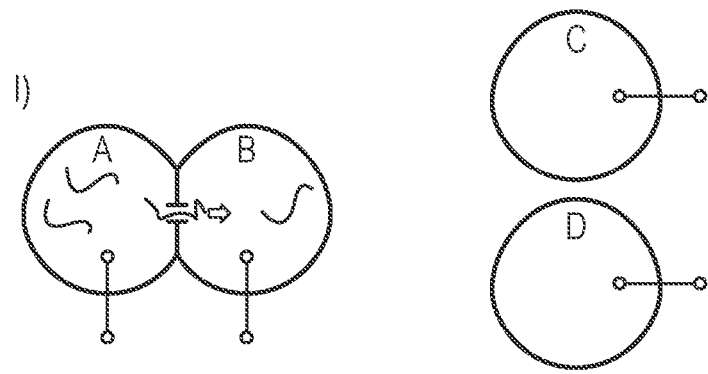
FIG. 16 is a diagram of a method of the invention whereby a droplet is fused with the second droplet.
Figure 16:
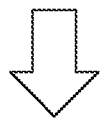
Figure 16:
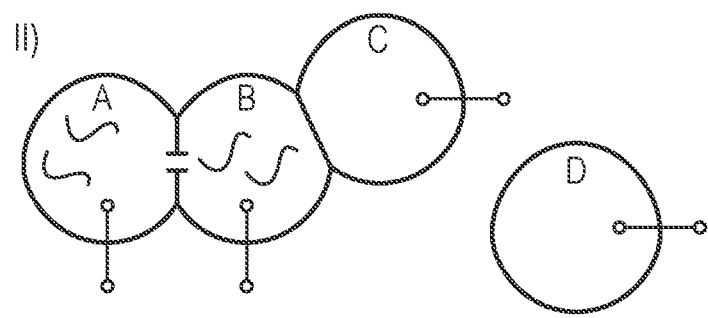
Figure 16:
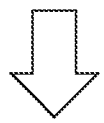
Figure 16:
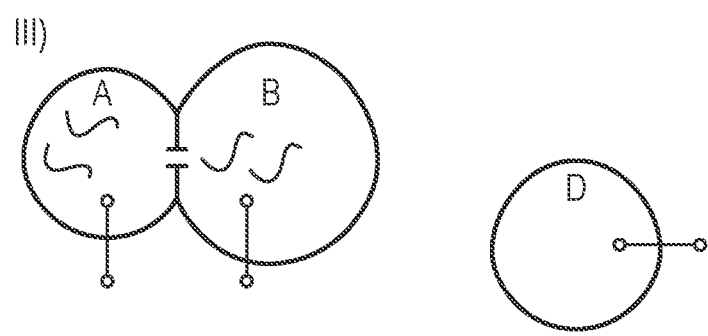

As explained above, one possible droplet operation involves the fusion of droplets. This is illustrated in FIG. 16.

An initial droplet setup is shown in FIG. 16(I). The first droplet A (comprising an analyte) is in contact with a second droplet B, and the first and second droplets are in electrical contact with a first and second sensing electrodes respectively (electrodes shown as lines ending in circles). The analyte present in the first droplet passes from the first to the second droplet via the first transmembrane pore, present at the interface between the first and second electrodes. The sensing system comprises at least two further droplets (shown as C and D), each in contact with a sensing electrode.

In this Example, step (a) comprises obtaining an electrical measurement indicating that the desired polynucleotide sequences (eg. genes of interest) have translocated from droplet A into droplet B. Step (b) comprises analysing that electrical measurement and determining that the translocation of the desired polynucleotide sequences have passed from droplet A to B, and further comprises selecting a droplet operation whereby droplet C can then be fused to droplet B. In step (c), this droplet operation is performed. An actuation signal is applied to droplet C in order to move it into contact with droplet B, and into contact with a further sensing electrode (indicated by the line ending in circles contacting droplet C). This arrangement is shown in FIG. 16(II). A brief pulse of high applied voltage across the B & C interface is then provided, typically using the second and/or further sensing electrodes, which fuses droplets B and C together; as can be seen in FIG. 16(III), the membrane separating droplets B and C is lost. The fusion delivers the entire contents of droplet C into droplet B. Droplet C contains the appropriate enzymes and co-factor reagents necessary to amplify the target molecules by PCR, and so these are delivered to the analyte in droplet (b) by the fusion step. Once the desired targets of interest in droplet B are amplified, they are processed or sequenced as desired by moving droplet B and connecting to further droplets as required. This is a useful means of amplifying specific DNA targets.

Example 4—Osmosis

As explained above, in some embodiments where the droplet operation involves connecting two droplets of different osmotic potential, it is possible to dilute or concentrate the contents in one of the droplets.

Figure 17:
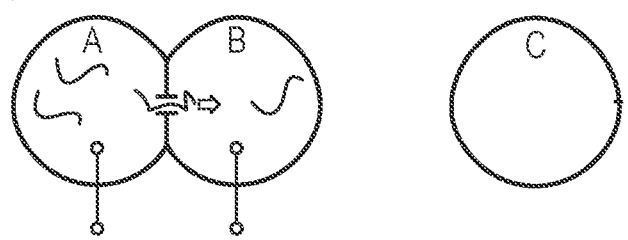
FIG. 17 is a diagram of a method of the invention wherein droplets of different osmotic potentials are brought into contact.
Figure 17:
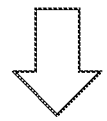
Figure 17:
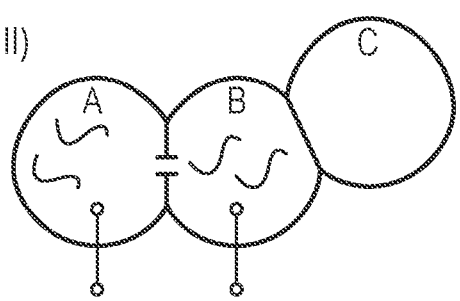
Figure 17:
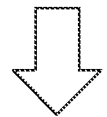
Figure 17:
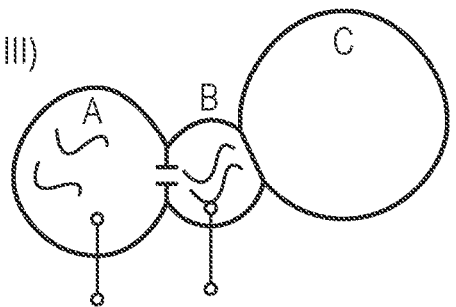

An example of such a method is illustrated in FIG. 17. The initial droplet setup is shown in FIG. 17(I). The first droplet A (comprising an analyte) is in contact with a second droplet B, and the first and second droplets are in electrical contact with a first and second sensing electrodes respectively (electrodes shown as lines ending in circles). The analyte present in the first droplet passes from the first to the second droplet via the first transmembrane pore, present at the interface between the first and second electrodes. The sensing system comprises a further droplet (shown as C).

In a first example, 4A, the analyte is a DNA sample. The desired strands among the DNA sample, referred to as the desired polynucleotides, are passed from A to B by real-time monitoring of the DNA sequences as they interact with the first transmembrane pore. As described above, step (a) comprises obtaining an electrical measurement across the first and second electrodes indicating translocation of the desired polynucleotide from the first to the second droplet. The electrical measurement is analysed to determine whether the detected species is a desired polynucleotide: if it is, the strand is passed into droplet A and if not it is returned to droplet B. This can be achieved by application of a suitable voltage across the interface between A and B. In this example, the analyte contains a large genomic background, or RNA in a DNA background. After step (a) has been repeated one or more times, step (b) is performed. In this step, it is determined by analysis of an electrical measurement taken in step (a) that the desired polynucleotides are collected in droplet B and a droplet operation is selected whereby a third droplet (droplet C) can be connected to droplet B. In one aspect of method 4A, step (b) also comprises selecting a droplet operation whereby droplet B and droplet A are separated, but this aspect is not shown in FIG. 17. The droplet operation selected moves droplet C into contact with droplet B and forms a new droplet interface comprising a bilayer of amphipathic molecules between droplets B and C, shown in FIG. 17(II). The sensing system comprises a pool of different droplets having different osmotic potentials (not shown). However, droplet C is selected as it has the appropriate osmotic potential relative to droplet B to alter the conditions in droplet B by osmosis. In this example, B has a lower salt concentration (lower osmotic potential) than C and so once B and C are connected as shown in FIG. 17(III), droplet B shrinks by losing water to droplet C. In this way species present in droplet B, including the desired polynucleotide, are concentrated. The method further comprises, once it is detected that B is sufficiently concentrated, selecting and performing a droplet operation to bring droplet B into contact with another droplet. In one aspect of this example, the droplet interface formed between B and the another droplet comprises a transmembrane pore and the interaction of the desired polynucleotide is detected for sensing purposes.

Another example is performed, 4B. 4B differs from 4A in that droplet B has a higher ion concentration (a higher osmotic potential) than droplet C, and hence when they are brought in to contact droplet C dilutes the contents of droplet B.

Example 5—Topping Up Mediator

In many nanopore sensing applications it is advantageous to separate the electrochemistry mediator (eg. potassium ferrocyanide, potassium ferricyanide couple) from the analytes, for example for nanopore sequencing of DNA or RNA. The electrochemistry mediators can have unwanted reactions with the sequencing chemistry, such as reacting with enzyme motors.

Figure 18:
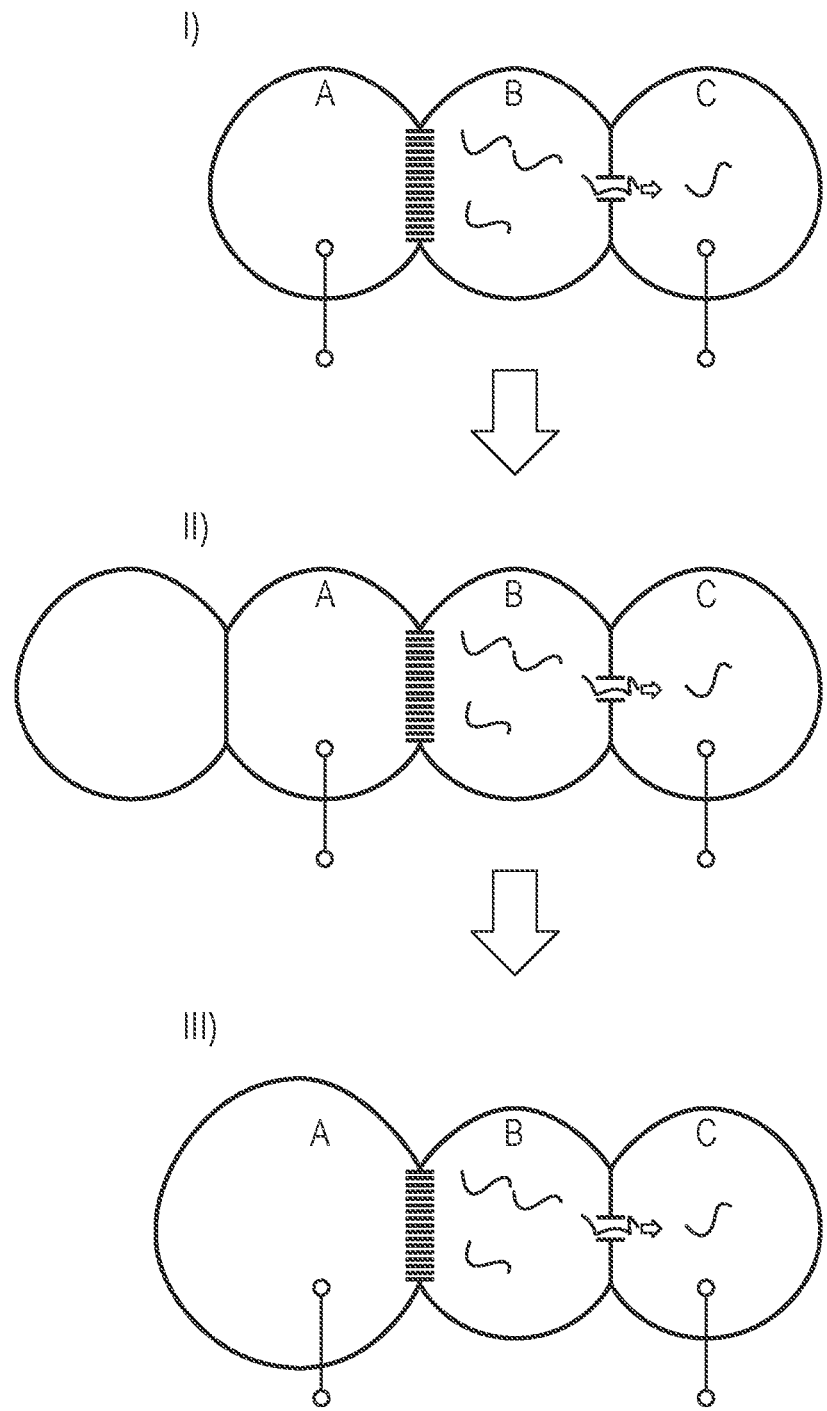
FIG. 18 is a diagram of a method of the invention wherein an electron mediator species is added to a droplet.

FIG. 18 illustrates a method of separating the electrochemistry mediator by use of separate droplets connected by droplet interface bilayers. In FIG. 18, droplet A and droplet C both contain electrochemistry mediator. Droplet B contains the DNA or RNA for sequencing, which is sequenced at the interface of droplet B and droplet C via a nanopore. Droplets A and C are connected to electrodes (eg. platinum) for the purposes of detecting ionic current changes to sequence the DNA. To enable passage of the ionic current from droplet A to droplet B, the interface between droplet A and B contains a very high number of nanopores. A high number of nanopores in the interface between droplet A and droplet B reduces the electrical resistance at this point in the network, enabling current to flow between the electrodes to enable sensing at the interface between droplet B and droplet C.

The type and number of nanopores inserted into the interface between droplet A and droplet B is used to control the resistance at this point in the circuit. Nanopores with large diameters (eg. >2 nm) are used to allow large amounts of current to pass freely.

Alternatively, small nanopores (eg. <2 nm in diameter) are used to control ionic selectivity, for example to prevent unwanted ionic species passing the membrane. In particular, the flow of the damaging ferrocyanide/ferricyanide species from passing through the membrane by using nanopores that are too narrow to pass the large ions, or nanopores with negative charges in the central channel to create electrostatic barriers to passage.

Controlling which membranes the nanopores insert into, in a multiple interface network, is achieved by either controlling the order in which membrane interfaces are formed, the application of large voltages across desired membrane interfaces, or by controlling which droplets contain the nanopores. Thus, the large numbers of the "frit" nanopores are inserted in the interface of droplet A and droplet B by including the nanopores only in droplet A. Likewise, the sensing nanopore is inserted into the interface between droplet B and droplet C by ensuring that droplet B contains the sensing nanopore (eg. for DNA sequencing).

Changes in mediator concentration across the network are sensed by monitoring the change in voltage, arising from a change in chemical potential as the mediator is reacted from one species to the other. In this way it is possible to detect that the mediator has become depleted during long experiments. When the mediator is depleted the conditions in droplet A are adjusted to refresh the mediator. A new droplet containing fresh mediator is connected and fused into droplet A (FIGS. 5 B and C). Alternatively, droplet A is moved away from droplet B, un-forming the droplet interface bilayer, and a new droplet A containing fresh mediator is connected to droplet A (also containing fresh nanopores to insert at the interface to enable ionic flow).

Alternatively, the mediator is not included in droplet C, but rather separated into a fourth droplet, D, connected by a frit-like nanopore interface to create an network A-B-C-D, where A and D contain the mediator, B contains the analyte, and the nanopore sensor is in the interface between droplet B and droplet C. In this network, the A mediator droplet is removed and replaced if and when sensing detects that the mediator is depleted, without affecting the sensing droplets B and C. Similarly, the D mediator droplet is removed and replaced if and when sensing detects that the mediator is depleted, without affecting the sensing droplets B and C.

Further Information

Unless defined otherwise, all technical and scientific terms used herein have the same meanings as commonly understood by one of skill in the art to which the disclosed invention belongs. Publications cited herein and the materials for which they are cited are specifically incorporated by reference.

The present invention is described with respect to particular embodiments and with reference to certain drawings but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the above detailed description when read in conjunction with the accompanying drawings. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

In addition, as used in this specification and the appended claims, the singular forms "a", "an", and "the" include plural referents unless the content clearly dictates otherwise. Thus, for example, reference to "a polynucleotide" includes two or more polynucleotides, reference to "a polynucleotide binding protein" includes two or more such proteins, reference to "a helicase" includes two or more helicases, reference to "a monomer" refers to two or more monomers, reference to "a pore" includes two or more pores and the like.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of operating a sensing system, wherein the sensing system comprises:
    (i) an electrowetting device, which electrowetting device comprises:
        an array of actuation electrodes;
        an insulator layer covering the actuation electrodes and having an outermost hydrophobic surface;
        a first sensing electrode; and
        a second sensing electrode;
    (ii) disposed on the hydrophobic surface,
        (a) a fluid medium; and
        (b) a first droplet and a second droplet each comprising liquid medium, wherein the first and second droplet are formed in the fluid medium,
        wherein the liquid medium is polar and the fluid medium is apolar or the liquid medium is apolar and the fluid media is polar;
        the first and/or the second droplet comprise a layer of amphipathic molecules at an interface between said first and/or second droplet and the fluid medium;
        the first droplet being in contact with the second droplet via a droplet interface;
        the droplet interface comprising a layer of amphipathic molecules and a first transmembrane pore; and
    (iii) a control system configured to obtain an electrical measurement from the first and second sensing electrodes, and to apply an actuation signal to the array of actuation electrodes;
wherein the method comprises
    a) obtaining an electrical measurement from the first and second sensing electrodes;
    b) analysing the electrical measurement and then selecting a droplet operation based on the electrical measurement according to one or more instructions stored in the control system; and
    c) applying an actuation signal to an actuation electrode to effect the droplet operation.

2. A method according to claim 1 wherein the first and the second droplet each comprise a layer of amphipathic molecules at an interface between the liquid medium and the fluid medium.

3. A method according to claim 1, wherein the first droplet is also in contact with one or more further droplets of liquid medium via a further droplet interface, and the further droplet interface comprises a layer of amphipathic molecules.

4. A method according to claim 1, wherein each droplet interface comprises a bilayer of amphipathic molecules.

5. A method according to claim 1, wherein one or more of the droplet interfaces comprises a plurality of ion channels; optionally wherein the droplet interface comprising a plurality of ion channels contacts the first droplet.

6. A method according to claim 1, wherein the first droplet comprises an analyte.

7. A method according to claim 1, wherein the second droplet comprises an electron mediator, and/or wherein the first droplet comprises an electron mediator.

8. A method according to claim 1, wherein the system comprises a third droplet of liquid medium and the third droplet comprises an electron mediator.

9. A method according to claim 1, wherein the first droplet (or where present optionally the third droplet) is in electrical contact with the first sensing electrode, and the second droplet is in electrical contact with the second sensing electrode.

10. A method according to claim 1, wherein the electrowetting device comprises:
    a first substrate supporting the array of activation electrodes; and
    a second substrate facing the hydrophobic surface of the insulator layer and supporting the first and second sensing electrodes.

11. A method according to claim 1, wherein step (a) comprises detecting the interaction of an analyte with the first transmembrane pore, and step (b) comprises identifying the analyte in whole or in part; optionally wherein the analyte comprises a polynucleotide, and step (b) comprises determining the identity of two or more nucleotides present in the polynucleotide sequence.

12. A method according to claim 1, wherein step (b) comprises comparing the electrical measurement to a value stored by the control system, and selecting a droplet operation based on the comparison between the electrical measurement and the stored value, according to one or more instructions stored in the control system.

13. A method according to claim 1, wherein step (a) is repeated one or more times to obtain a plurality of electrical measurements, and step (b) comprises comparing one or more electrical measurements among the plurality of electrical measurements with one or more other electrical measurements among the plurality of electrical measurements; optionally wherein:
    step (a) is repeated a plurality of times to obtain a plurality of electrical measurements; and
    step (b) comprises:
        comparing one or more of the electrical measurements with one or more of the other electrical measurements among the plurality of electrical measurements;
        determining an alteration in the electrical measurement detected over time; and
        selecting a droplet operation to reverse the alteration in the electrical measurement.

14. A method according to claim 1, wherein step (b) comprises determining a physical or chemical property of the first droplet and/or the second droplet and/or, where present, the third droplet, and selecting a droplet operation in order to modify or maintain said physical or chemical property of the first droplet and/or the second droplet and/or, where present, the third droplet.

15. A method according to claim 1, wherein step (b) comprises determining the ion concentration of the first droplet and/or the second droplet and/or, where present, the third droplet;
    optionally wherein step (b) further comprises selecting a droplet operation in order to increase or decrease the ion concentration of the first droplet and/or the second droplet and/or, where present, the third droplet; and
    optionally wherein the ion concentration is the concentration of an electron mediator species.

16. A method according to claim 1 wherein step (b) comprises establishing whether an analyte is present, or determining the concentration of an analyte, in the first droplet.

17. A method according to claim 1, wherein step (b) comprises selecting an experimental procedure to perform on the first droplet; and selecting a droplet operation to bring the first droplet into contact with one or more droplets to enable that experiment to be performed.

18. A method according to claim 1, wherein step (c) comprises moving an actuated droplet of liquid medium upon the hydrophobic surface; optionally wherein the actuated droplet is the first or the second or where present the third droplet.

19. A method according to claim 18, wherein step (c) comprises separating the actuated droplet at a droplet interface from a further droplet of liquid medium, which further droplet may be the first, second or where present the third droplet, and said droplet interface comprises a layer of amphipathic molecules; optionally wherein step (c) comprises separating the actuated droplet at a plurality of droplet interfaces from a plurality of further droplets of liquid medium, which further droplets may include the first, second or where present the third droplet, and each of said droplet interfaces comprises a layer of amphipathic molecules.

20. A method according to claim 18, wherein said one or more droplet interfaces each comprise a bilayer of amphipathic molecules, and step (c) comprises separating the said bilayer.

21. A method according to claim 18, wherein step (c) comprises placing the actuated droplet in contact with a further droplet of liquid medium to form a droplet interface, which further droplet may be the first, second or where present the third droplet; optionally wherein step (c) comprises placing the actuated droplet in contact with a plurality of further droplets of liquid medium to form a plurality of droplet interfaces, which further droplets may include the first, second or where present the third droplet.

22. A method according to claim 21, wherein said one or more droplet interfaces each comprise a layer of amphipathic molecules; optionally wherein said one or more droplet interfaces each comprise a bilayer of amphipathic molecules, and step (c) comprises forming the said bilayer.

23. A method according to claim 18, wherein step (c) comprises fusing the actuated droplet with a further droplet of liquid medium, which further droplet may be the first, second or where present the third droplet; optionally wherein the actuated droplet does not comprise an external layer of amphipathic molecules.

24. A method according to claim 23, wherein the actuated droplet comprises one or more of: an electron mediator, an analyte, and an experimental substrate.

25. A method according to claim 1, wherein step (c) comprises splitting the first droplet or the second droplet or where present the third droplet into two or more parts.

26. A method of operating a sensing system, wherein the sensing system comprises:
- (i) an electrowetting device, which electrowetting device comprises:
  - an array of actuation electrodes,
  - an insulator layer covering the actuation electrodes and having an outermost hydrophobic surface;
  - a first sensing electrode; and
  - a second sensing electrode;
- (ii) disposed on the hydrophobic surface,
  - an apolar fluid medium,
  - a first, second and third droplet comprising a polar liquid medium,
  - the first and/or the second and/or the third droplet comprises a layer of amphipathic molecules at an interface between said first and/or second and/or third droplet and the apolar fluid medium;
  - the first droplet is in contact with the second droplet via a droplet interface and with the third droplet via a droplet interface;
  - each droplet interface comprises a layer of amphipathic molecules;
  - at least the interface between the first droplet and the second droplet comprises a transmembrane pore;
  - the first droplet comprises an analyte;
  - each of the second and the third droplets comprises an electron mediator; and
  - the second and third droplets are in electrical contact with the second sensing electrode and the first sensing electrode respectively;
- (iii) a control system configured to obtain an electrical measurement from the first and second sensing electrodes, and to apply an actuation signal to the array of actuation electrodes;

wherein the method comprises
- a) obtaining an electrical measurement from the first and second sensing electrodes;
- b) analysing the electrical measurement and then selecting a droplet operation based on the electrical measurement according to one or more instructions stored in the control system; and
- c) applying an actuation signal to an actuation electrode to effect the droplet operation;
  - wherein the droplet operation comprises moving the first droplet to separate the first droplet from the second and/or third droplets, or moving the second and/or third droplets to separate the second and/or third droplets from the first droplet.

27. A method according to claim 26, wherein the method further comprises moving a further droplet comprising an analyte into contact with the second and third droplets to form a droplet interface between each of the second and third droplets and the further droplet, wherein each droplet interface comprises a layer of amphipathic molecules.

28. A method according to claim 26, wherein the droplet operation further comprises moving the second and/or third droplets into contact with a further droplet comprising analyte to form a droplet interface between the second and/or third droplet and the further droplet, wherein the interface(s) comprise a layer of amphipathic molecules.

29. A method according to claim 28, wherein the method further comprises moving a fourth and optionally also a fifth droplet into contact with the first droplet to form a droplet interface between the fourth and where present the fifth droplet and the first droplet, wherein the droplet interface or droplet interfaces comprise a layer of amphipathic molecules; optionally wherein the fourth and where present optionally also the fifth droplets comprise an electron mediator.

30. A method according to claim 26, wherein:
- step (a) comprises contacting the first transmembrane pore with an analyte such that the analyte moves with respect to the pore, and obtaining one or more electrical measurements as the analyte moves with respect to the pore; and
- step (b) comprises determining the presence or absence of one or more characteristics of the analyte, and determining whether to keep or dispose of the first droplet based on the presence, or absence, or one or more characteristics of the analyte.

31. A method according to claim 30, wherein the analyte is a polynucleotide, and wherein said characteristics are one or more of (i) the length of the polynucleotide, (ii) the identity of the polynucleotide, (iii) the sequence of the polynucleotide, (iv) the secondary structure of the polynucleotide, and (v) whether or not the polynucleotide is modified.

32. A method of operating a sensing system, wherein the sensing system comprises:
- (i) an electrowetting device, which electrowetting device comprises:
  - an array of actuation electrodes, and
  - an insulator layer covering the actuation electrodes and having an outermost hydrophobic surface;
  - a first sensing electrode; and
  - a second sensing electrode;
- (ii) disposed on the hydrophobic surface:
  - an apolar fluid medium,
  - a first, second and optionally a third droplet comprising a polar liquid in the apolar fluid medium;
  - the first and/or the second droplet comprises a layer of amphipathic molecules at an interface between said first and/or second droplet and the apolar fluid medium;
  - the first droplet is in contact with the second droplet via a droplet interface, or the third and second droplets are each in contact with the first droplet via a droplet interface;
  - each droplet interface comprises a layer of amphipathic molecules;
  - at least one of the droplet interfaces comprises a transmembrane pore;
  - the first droplet comprises an analyte;
  - one of the first and the second droplets comprises an electron mediator;
  - the first or where present optionally the third droplet is in electrical contact with the first sensing electrode; and
  - the second droplet is in electrical contact with the second sensing electrode;
- (iii) a control system configured to obtain an electrical measurement from the first and second sensing electrodes, and to apply an actuation signal to the array of actuation electrodes;

and wherein the method comprises
- a) obtaining an electrical measurement from the first and second electrodes, and repeating this step a plurality of times to obtain a plurality of electrical measurements;
- b) comparing one or more of the electrical measurements with one or more of the other electrical measurements among the plurality of electrical measurements, determining an alteration in the electrical measurement detected over time that is attributable to a loss of electron mediator in the droplet, optionally in the second droplet, and selecting a droplet operation to increase the concentration of electron mediator in that droplet, optionally in the second droplet; and c) applying an actuation signal to an actuation electrode to effect the droplet operation.

33. A method according to claim 32, wherein the droplet operation comprises moving an actuated droplet of fluid medium upon the hydrophobic surface and fusing the actuated droplet with the droplet comprising the electron mediator, which is optionally the second droplet, wherein the actuated droplet comprises an electron mediator; or (b) moving the droplet comprising the electron mediator out of contact with the first or second sensing electrode and moving a new droplet comprising fresh electron mediator into electrical contact with the first or second sensing electrode.

34. A method of operating a sensing system wherein the sensing system comprises
  (i) an electrowetting device, which electrowetting device comprises:
    an array of actuation electrodes;
    an insulator layer covering the actuation electrodes and having an outermost hydrophobic surface;
    a first sensing electrode; and
    a second sensing electrode;
  (ii) disposed on the hydrophobic surface of the electrowetting device:
    an apolar fluid medium;
    a first, second and third droplet comprising a polar liquid medium;
    the first and/or the second and/or the third droplet comprise a layer of amphipathic molecules at an interface between said first and/or second and/or third droplet and the apolar fluid medium;
    the first droplet being in contact with the second droplet via a droplet interface, said droplet interface comprising a layer of amphipathic molecules and a first transmembrane pore;
    the third droplet being in contact with the first or second droplet via another droplet interface, said another droplet interface comprising a layer of amphipathic molecules and a second transmembrane pore; and
    the first droplet comprising an analyte;
  (iii) a control system configured to obtain an electrical measurement from the first and second sensing electrodes, and to apply an actuation signal to the array of actuation electrodes;
wherein the method comprises
  a) obtaining an electrical measurement from the first and second sensing electrodes;
  b) analysing the electrical measurement and then selecting a droplet operation based on the electrical measurement according to one or more instructions stored in the control system; and
  c) applying an actuation signal to an actuation electrode to effect the droplet operation.

35. A method according to claim 34, wherein step (b) comprises determining that the analyte has interacted with (i) the first transmembrane pore, or (ii) the second transmembrane pore, or (iii) the first and second transmembrane pores simultaneously.

36. A method according to claim 34, wherein the droplet operation selected in step (b) and performed in step (c) comprises moving one or more of the first droplet, the second droplet and the third droplet in order to separate the first droplet from the second droplet and/or the third droplet.

37. A method according to claim 34, wherein the method further comprises bringing the first droplet into contact with a further droplet, such that the further droplet contacts the first droplet via a droplet interface comprising a layer of amphipathic molecules and a further transmembrane protein.

38. A method of operating a sensing system, wherein the sensing system comprises:
  (i) an electrowetting device, which electrowetting device comprises:
    an array of actuation electrodes, and
    an insulator layer covering the actuation electrodes and having an outermost hydrophobic surface;
    a first sensing electrode; and
    a second sensing electrode;
  (ii) disposed on the hydrophobic surface:
    an apolar fluid medium,
    first, second, third and fourth droplets each comprising a polar liquid in the apolar fluid medium;
    the first, second, third and/or fourth droplet comprises a layer of amphipathic molecules at an interface between said first, second, third and/or fourth droplet and the apolar fluid medium;
    the third droplet is in contact with the first droplet via a droplet interface, the first droplet is in contact with the second droplet via another droplet interface, and the second droplet is in contact with the fourth droplet via yet another droplet interface;
    each droplet interface comprises a layer of amphipathic molecules;
    the droplet interface between the first and second droplets comprises a first transmembrane pore;
    the droplet interface between the first and third droplets comprises a plurality of further transmembrane pores which are ion channels;
    the droplet interface between the second and fourth droplets also comprises a plurality of further transmembrane pores which are ion channels;
    the first droplet comprises an analyte;
    the third and fourth droplets comprise an electron mediator;
    the third droplet is in electrical contact with the first sensing electrode; and
    the fourth droplet is in electrical contact with the second sensing electrode;
  (iii) a control system configured to obtain an electrical measurement from the first and second sensing electrodes, and to apply an actuation signal to the array of actuation electrodes;
wherein the method comprises
  a) obtaining an electrical measurement from the first and second electrodes, and repeating this step a plurality of times to obtain a plurality of electrical measurements;
  b) comparing one or more of the electrical measurements with one or more of the other electrical measurements among the plurality of electrical measurements, determining an alteration in the electrical measurement detected over time that is attributable to a loss of electron mediator in the third or fourth droplet and selecting a droplet operation to increase the concentration of electron mediator in that droplet; and
  c) applying an actuation signal to an actuation electrode to effect the droplet operation.

* * * * *